(12) United States Patent
Müller et al.

(10) Patent No.: US 6,525,211 B1
(45) Date of Patent: Feb. 25, 2003

(54) HERBICIDAL SULPHONYLAMINO(THIO)CARBONYL COMPOUNDS

(75) Inventors: Klaus-Helmut Müller, Düsseldorf (DE); Rolf Kirsten, Monheim (DE); Ernst Rudolf F. Gesing, Erkrath (DE); Joachim Kluth, Langenfeld (DE); Mark Wilhelm Drewes, Langenfeld (DE); Kurt Findeisen, Leverkusen (DE); Johannes Rudolf Jansen, Monheim (DE); Klaus König, Odenthal (DE); Hans-Jochem Riebel, Wuppertal (DE); Otto Schallner, Monheim (DE); Markus Dollinger, Leverkusen (DE); Hans-Joachim Santel, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/838,812

(22) Filed: Apr. 20, 2001

Related U.S. Application Data

(60) Division of application No. 09/223,246, filed on Dec. 30, 1998, now Pat. No. 6,251,831, which is a continuation of application No. 09/006,686, filed on Jan. 8, 1998, now abandoned, which is a continuation-in-part of application No. PCT/EP96/02826, filed on Jun. 28, 1996.

(30) Foreign Application Priority Data

Jul. 11, 1995 (DE) .......................... 195 25 162

(51) Int. Cl.$^7$ ..................... C07C 309/41; C07C 311/29
(52) U.S. Cl. ..................... 558/413; 562/833; 562/870; 564/89
(58) Field of Search .......................... 558/413; 562/833, 562/870; 564/89

(56) References Cited

U.S. PATENT DOCUMENTS

| | | | |
|---|---|---|---|
| 4,419,121 A | 12/1983 | Meyer et al. | 71/92 |
| 4,425,154 A | 1/1984 | Meyer et al. | 71/92 |
| 4,443,245 A | 4/1984 | Meyer et al. | 71/93 |
| 4,479,821 A | 10/1984 | Meyer et al. | 71/93 |
| 5,057,144 A | 10/1991 | Daum et al. | 71/92 |
| 5,085,684 A | 2/1992 | Müller et al. | 71/92 |
| 5,238,910 A | 8/1993 | Müller et al. | 514/258 |
| 5,252,540 A | 10/1993 | Heistracher et al. | 504/280 |
| 5,300,480 A | 4/1994 | Haas et al. | 504/273 |
| 5,488,028 A | 1/1996 | Haas et al. | 504/193 |
| 5,534,486 A | 7/1996 | Müller et al. | 504/273 |
| 5,552,369 A | 9/1996 | Findeisen et al. | 504/273 |
| 5,670,691 A | 9/1997 | Spangler et al. | 558/56 |
| 5,693,590 A | 12/1997 | Fisher et al. | 504/105 |
| 5,858,924 A | 1/1999 | Johnson et al. | 504/241 |

FOREIGN PATENT DOCUMENTS

| | | |
|---|---|---|
| DE | 43 34 791 A1 | 4/1994 |
| DE | 195 25 162 | 1/1997 |
| DE | 197 31 437 A1 | 1/1998 |
| EP | 0 023 422 A2 | 2/1981 |
| EP | 0 044 807 A2 | 1/1982 |

(List continued on next page.)

OTHER PUBLICATIONS

Jaeggi, Chemical Abstracts, vol. 108:5696, 1988.*
Gyul'akhmedov et al., Chemical Abstracts, vol. 98:160326, 1983.*
Okubo et al., Chemical Abstracts, vol. 90:152610, 1979.*
Kuliev et al., Chemical Abstracts, vol. 86:189383, 1977.*

* cited by examiner

Primary Examiner—Richard L. Raymond
(74) Attorney, Agent, or Firm—Norris McLaughlin & Marcus

(57) ABSTRACT

The invention relates to novel sulphonylamino(thio)carbonyl compounds of the formula (I),

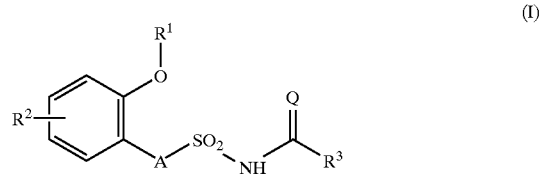

in which A represents a single bond, oxygen, sulphur or the group N—R, in which R represents hydrogen, alkyl, alkenyl, alkinyl or cycloalkyl, Q represents oxygen or sulphur, $R^1$ represents hydrogen or formyl or represents in each case optionally substituted alkyl, alkenyl, alkinyl, alkylcarbonyl, alkoxycarbonyl, alkylsulphonyl, cycloalkyl, cycloalkylcarbonyl or cycloalkylsulphonyl, $R^2$ represents cyano or halogen or represents in each case optionally substituted alky, alkenyl, alkinyl, alkoxy, alkenyloxy or alkinyloxy, and $R^3$ represents in each case optionally substituted heterocyclyl having 5 ring members of which at least one is oxygen, sulphur or nitrogen and from one to three further ring members can be nitrogen, and salts of compounds of the formula (I), the previously known compounds 4,5-dimethoxy-2-(2,5-dimethoxy-phenylsulphonylaminocarbonyl)-2,4-dihydro-3H-1,2,4-triazol-3-one, 4,5-diethoxy-2-(2,5-dimethoxy-phenylsulphonylaminocarbonyl)-2,4-dihydro-3H-1,2,4-triazol-3-one and N-(2,5-dimethoxy-phenylsulphonyl)-1,5-dimethyl-1H-pyrazole-3-carboxamide being excluded by disclaimer;

and also to processes and novel intermediates for the preparation of the novel substances and to their use as herbicides.

2 Claims, No Drawings

FOREIGN PATENT DOCUMENTS

| | | |
|---|---|---|
| EP | 0 084 020 A2 | 7/1983 |
| EP | 0 425 948 A2 | 5/1991 |
| EP | 0 482 349 A2 | 4/1992 |
| EP | 0 511 826 A2 | 11/1992 |
| EP | 0 534 266 A1 | 3/1993 |
| EP | 0 708 087 A1 | 4/1996 |
| EP | 0 511 826 B1 | 7/1997 |
| WO | WO 92/09608 | 6/1992 |
| WO | WO 93/16998 | 9/1993 |
| WO | WO 95/27703 | 4/1994 |
| WO | WO 96/11188 | 4/1996 |
| WO | WO 96/22982 | 8/1996 |
| WO | WO 96/27590 | 9/1996 |
| WO | WO 96/27591 | 9/1996 |
| WO | WO 96/35680 | 11/1996 |

HERBICIDAL SULPHONYLAMINO(THIO)CARBONYL COMPOUNDS

This application is a division of application Ser. No. 09/223,246, filed Dec. 30, 1998, now U.S. Pat. No. 6,251,831, which is a continuation of application Ser. No. 09/006,686, filed Jan. 8, 1998, now abandoned, which is a continuation-in-part of PCT/EP96/02826, filed Jun. 28, 1996.

The invention relates to novel sulphonylamino(thio) carbonyl compounds, to a number of processes and to novel intermediates for their preparation, and to their use as herbicides.

It is already known that certain sulphonylaminocarbonyl compounds, such as, for example, the compounds 4,5-dimethoxy-2-(2-methoxy-phenylsulphonylaminocarbonyl)-2,4-dihydro-3H-1,2,4-triazol-3-one, 4,5-dimethoxy-2-(2,5-dimethoxy-phenylsulphonylaminocarbonyl)-2,4-dihydro-3H-1,2,4-triazol-3-one, 4,5-diethoxy-2-(2,5-dimethoxy-phenylsulphonylaminocarbonyl)-2,4-dihydro-3H-1,2,4-triazol-3-one and N-(2,5-dimethoxy-phenylsulphonyl)-1,5-dimethyl-1H-pyrazole-3-carbox-amide possess herbicidal properties (cf. EP 341489, EP 422469, EP 425948, EP 431291, EP 507171, EP 534266, DE 4029753). The action of these compounds, however, is not in every respect satisfactory.

The novel sulphonylamino(thio)carbonyl compounds have now been found of the general formula (I),

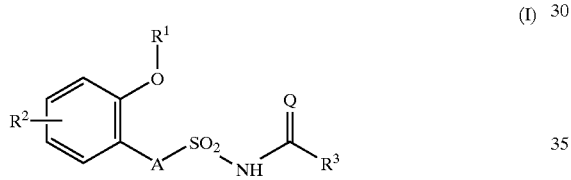

in which
- A represents a single bond, oxygen, sulphur or the group N—R, in which R represents hydrogen, alkyl, alkenyl, alkinyl or cycloalkyl,
- Q represents oxygen or sulphur,
- $R^1$ represents hydrogen or formyl or represents in each case optionally substituted alkyl, alkenyl, alkinyl, alkylcarbonyl, alkoxycarbonyl, alkylsulphonyl, cycloalkyl, cycloalkylcarbonyl or cycloalkylsulphonyl,
- $R^2$ represents cyano or halogen or represents in each case optionally substituted alkyl, alkenyl, alkinyl, alkoxy, alkenyloxy or alkinyloxy, and
- $R^3$ represents in each case optionally substituted heterocyclyl having 5 ring members of which at least one is oxygen, sulphur or nitrogen and from one to three further ring members can be nitrogen, and salts of compounds of the formula (I),
the previously known compounds 4,5-dimethoxy-2-(2,5-dimethoxy-phenylsulphonylaminocarbonyl)-2,4-dihydro-3H-1,2,4-triazol-3-one, 4,5-diethoxy-2-(2,5-dimethoxy-phenylsulphonylaminocarbonyl)-2,4-dihydro-3H-1,2,4-triazol-3-one and N-(2,5-dimethoxy-phenylsulphonyl)-1,5-dimethyl-1H-pyrazole-3-carboxamiide being excluded by disclaimer.

The novel sulphonylamino(thio)carbonyl compounds of the general formula (I) are obtained if (a) aminosulphonyl compounds of the general formula (II)

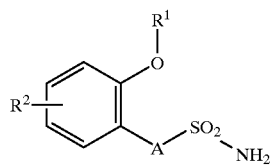

in which
A, $R^1$ and $R^2$ have the meanings given above
are reacted with (thio)carboxylic acid derivatives of the general formula (III)

in which
Q and $R^3$ have the meanings given above and
z represents halogen, alkoxy, aryloxy or arylalkoxy,
optionally in the presence of an acid acceptor and
optionally in the presence of a diluent,
or if (b) sulphonyl iso(thio)cyanates of the general formula (I)

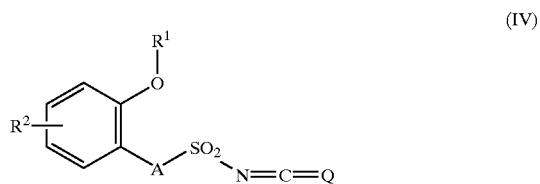

in which
A, Q, $R^1$ and $R^2$ have the meanings given above
are reacted with heterocycles of the general formula (V)

in which
$R^3$ has the meaning given above,
optionally in the presence of a reaction auxiliary and
optionally in the presence of a diluent,
or if (c) chlorosulphonyl compounds of the general formula (VI)

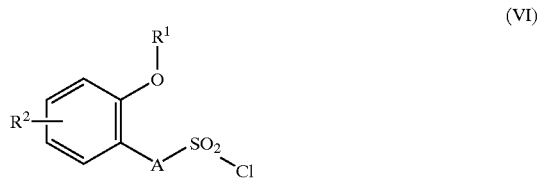

in which
A, $R^1$ and $R^2$ have the meanings given above
are reacted with heterocycles of the general formula (V)

in which
$R^3$ has the meaning given above and metal (thio)cyanates of the general formula (VII)

MQCN   (VII)

in which
Q has the meaning given above, and
M represents an alkali metal or alkaline earth metal equivalent,
optionally in the presence of a reaction auxiliary and optionally in the presence of a diluent,
or if
(d) chlorosulphonyl compounds of the general formula (VI)

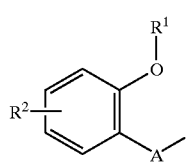   (VI)

in which
A, $R^1$ and $R^2$ have the meanings given above
are reacted with (thio)carboxamides of the general formula (VIII)

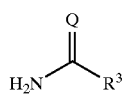   (VIII)

in which
Q and $R^3$ have the meanings given above,
optionally in the presence of an acid acceptor and optionally in the presence of a diluent,
or if
(e) sulphonylamino(thio)carbonyl compounds of the general formula (IX)

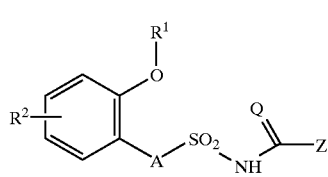   (IX)

in which
A, Q, $R^1$ and $R^2$ have the meanings given above, and
Z represents halogen, alkoxy, aryloxy or arylalkoxy,
are reacted with heterocycles of the general formula (V)

H—$R^3$   (V)

in which
$R^3$ has the meaning given above,
optionally in the presence of an acid acceptor and optionally in the presence of a diluent,
or if
(f) heterocycles of the general formula (V)

H—$R^3$   (V)

in which $R^3$ has the meaning given above,
are reacted with chlorosulphonyl iso(thio)cyanate, optionally in the presence of a diluent, and the adducts formed in this reaction are reacted in situ with benzene derivatives of the general formula (X)

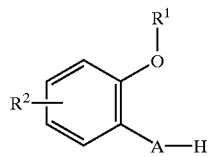   (X)

in which
A, $R^1$ and $R^2$ have the meanings given above,
optionally in the presence of an acid acceptor and optionally in the presence of a diluent,
and, if desired, the compounds of the formula (I) obtained by processes (a), (b), (c), (d), (e) or (f) are converted into salts by customary methods.

The novel sulphonylamino(thio)carbonyl compounds of the general formula (I) are distinguished by a strong herbicidal activity.

The invention relates preferably to compounds of the formula (I) in which

A represents a single bond, oxygen, sulphur or the group N—R, in which R represents hydrogen, $C_1$–$C_6$-alkyl, $C_2$–$C_6$-alkenyl, $C_2$–$C_6$-alkinyl or $C_3$–$C_6$-cycloalkyl, Q represents oxygen or sulphur, $R^1$ represents hydrogen or formyl or represents in each case optionally cyano-, fluoro-, chloro-, bromo-, phenyl- or $C_1$–$C_4$-alkoxy-substituted alkyl, alkenyl, alkinyl, alkylcarbonyl, alkoxycarbonyl or alkylsulphonyl having in each case up to 6 carbon atoms, or represents in each case optionally cyano-, fluoro-, chloro-, bromo- or $C_1$–$C_4$-alkyl-substituted $C_3$–$C_6$-cycloalkyl, $C_3$–$C_6$-cycloalkyl-carbonyl or $C_3$–$C_6$-cycloalkyl-sulphonyl, $R^2$ represents cyano, fluoro, chloro or bromo or represents in each case optionally cyano-, fluoro-, chloro-, bromo- or $C_1$–$C_4$-alkoxy-substituted alkyl, alkenyl, alkinyl, alkoxy, alkenyloxy or alkinyloxy having in each case up to 6 carbon atoms, and $R^3$ represents in each case optionally substituted heterocyclyl of the formulae below,

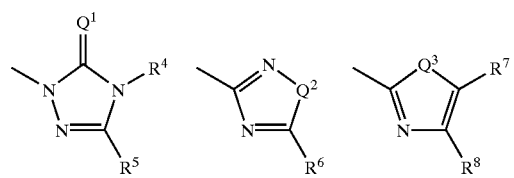

in which
$Q^1$, $Q^2$ and $Q^3$ each represent oxygen or sulphur, and
$R^4$ represents hydrogen, hydroxyl, amino or cyano, or represents $C_2$–$C_{10}$-alkylideneamino, or represents optionally fluoro-, chloro-, bromo-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or represents in each case optionally fluoro-, chloro- and/or bromo-substituted $C_2$–$C_6$-alkenyl or $C_2$–$C_6$-alkinyl, or represents in each case optionally fluoro-, chloro-, bromo-, cyano-, $C_1$–$C_4$-alkoxy- or $C_1$–$C_4$-alkoxycarbonyl-substituted $C_1$–$C_6$-alkoxy, $C_1$–$C_6$-alkylamino or $C_1$–$C_6$-alkyl-carbonylamino, or represents $C_3$–$C_6$-alkenyloxy, or represents di-($C_1$–$C_4$-alkyl)-amino, or represents in each case optionally fluoro-, chloro-, bromo-, cyano- and/or $C_1$–$C_4$-alkyl-substituted $C_3$–$C_6$-cycloalkyl, $C_3$–$C_6$-cycloalkylamino or $C_3$–$C_6$-cycloalkyl-$C_1$–$C_4$-alkyl, or represents in each case optionally fluoro-, chloro-, bromo-, cyano-, nitro-, $C_1$–$C_4$-alkyl-, trifluoromethyl- and/or $C_1$–$C_4$-alkoxy-substituted phenyl, phenylamino or phenyl-$C_1$–$C_4$-alkyl, $R^5$ represents hydrogen, hydroxyl, mercapto, amino, cyano, fluoro, chloro, bromo or iodo, or represents optionally fluoro-, chloro-, bromo-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or represents in each case optionally fluoro-, chloro- and/or bromo-substituted $C_2$–$C_6$-alkenyl or $C_2$–$C_6$-alkinyl, or represents in each case optionally fluoro-, chloro-, cyano-, $C_1$–$C_4$-alkoxy- or $C_1$–$C_4$-alkoxy-carbonyl-substituted $C_1$–$C_6$-alkoxy, $C_1$–$C_6$-alkylthio, $C_1$–$C_6$alkylamino or $C_1$–$C_6$-alkyl-carbonylamino, or represents $C_3$–$C_6$-alkenyloxy, $C_3$–$C_6$-alkinyloxy, $C_3$–$C_6$-alkenylthio, $C_3$–$C_6$-alkinylthio, $C_3$–$C_6$-alkenylamino or $C_3$–$C_6$-alkinylamino, or represents di-($C_1$–$C_4$-alkyl)-amino, or represents in each case optionally methyl- and/or ethyl-substituted aziridino, pyrrolidino, piperidino or morpholino, or represents in each case optionally fluoro-, chloro-, bromo-, cyano- and/or $C_1$–$C_4$-alkyl-substituted $C_3$–$C_6$-cycloalkyl, $C_5$–$C_6$-cycloalkenyl, $C_3$–$C_6$-cycloalkyloxy, $C_3$–$C_6$-cycloalkylthio, $C_3$–$C_6$-cycloalkylamino $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio or $C_3$–$C_6$-cycloalkyl-$C_1$–$C_4$-alkylamino, or represents in each case optionally fluoro-, chloro-, bromo-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, or $R^4$ and $R^5$ together represent optionally branched alkanediyl having 3 to 11 carbon atoms, and also $R^6$, $R^7$ and $R^8$ are identical or different and represent hydrogen, cyano, fluoro, chloro or bromo, or represent in each case optionally fluoro-, chloro-, bromo- or $C_1$–$C_4$-alkoxy-substituted alkyl, alkenyl, alkinyl, alkoxy, alkenyloxy, alkinyloxy, alkylthio, alkenylthio, alkinylthio, alkylsulphinyl and alkylsulphonyl having in each case up to 6 carbon atoms, or represents in each case optionally cyano-, fluoro-, chloro-, bromo- or $C_1$–$C_4$-alkyl-substituted cycloalkyl having 3 to 6 carbon atoms, the previously known compounds 4,5-dimethoxy-2-(2,5-dimethoxy-phenylsulphonylaminocarbonyl)-2,4-dihydro-3H-1,2,4-triazol-3-one, 4,5-diethoxy-2-(2,5-dimethoxy-phenylsulphonylaminocarbonyl)-2,4-dihydro-3H-1,2,4-triazol-3-one and N-(2,5-dimethoxy-phenylsulphonyl)-1,5-dimethyl-1H-pyrazole-3-carboxamide being excluded by disclaimer.

The invention also relates preferably to sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which A, Q, $R^1$, $R^2$ and $R^3$ have the meanings indicated above as preferred.

The invention relates in particular to compounds of the formula (I) in which

A represents a single bond, oxygen or the group N—R, in which R represents hydrogen, methyl, ethyl, n- or i-propyl, n-, i- or s-butyl, propenyl, butenyl, propinyl, butinyl, cyclopropyl, cyclobutyl, cyclopentyl or cyclohexyl, Q represents oxygen or sulphur, $R^1$ represents hydrogen or formyl, or represents in each case optionally fluoro-, chloro-, bromo-, methoxy- or ethoxy-substituted methyl, ethyl, n- or i-propyl, n-, i- or s-butyl, propenyl, butenyl, propinyl, butinyl, acetyl, propionyl, butyroyl, methoxycarbonyl, ethoxycarbonyl, n- or i-propoxycarbonyl, methylsulphonyl, ethylsulphonyl, n- or i-propylsulphonyl, n-, i-, s- or t-butylsulphonyl, or represents in each case optionally fluoro-, chloro- or methyl-substituted cyclopropyl, cyclopropylcarbonyl or cyclopropylsulphonyl, $R^2$ represents cyano, fluoro, chloro or bromo, or represents in each case optionally fluoro-, chloro-, methoxy- or ethoxy-substituted methyl, ethyl, n- or i-propyl, n-, i- or s-butyl, propenyl, butenyl, propinyl, butinyl, methoxy, ethoxy, n- or i-propoxy, n-, i- or s-butoxy, propenyloxy, butenyloxy, propinyloxy or butinyloxy and $R^3$ represents in each case optionally substituted heterocyclyl of the formulae below,

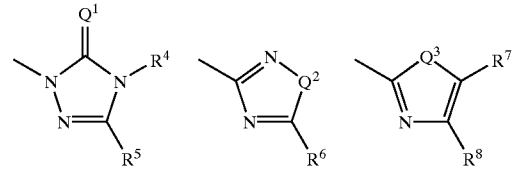

in which $Q^1$, $Q^2$ and $Q^3$ each represent oxygen or sulphur, and $R^4$ represents hydrogen, hydroxyl or amino, or represents $C_3$–$C_8$-alkylideneamino, or represents in each case optionally fluoro-, chloro-, cyano-, methoxy- or ethoxy-substituted methyl, ethyl, n- or i-propyl, n-, i-, s- or t-butyl, or represents in each case optionally fluoro-, chloro- or bromo-substituted propenyl, butenyl, propinyl or butinyl, or represents in each case optionally fluoro-, chloro-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, or represents propenyloxy or butenyloxy, or represents dimethylamino or diethylamino, or represents in each case optionally fluoro-, chloro-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents in each case optionally fluoro-, chloro-, methyl-, trifluoromethyl- and/or methoxy-substituted phenyl or benzyl, $R^5$ represents hydrogen, hydroxyl, mercapto, amino, fluoro, chloro or bromo, or represents in each case optionally fluoro-, chloro-, cyano-, methoxy- or ethoxy-substituted methyl, ethyl, n- or i-propyl, n-, i-, s- or t-butyl, or represents in each case optionally fluoro-, chloro- or bromo-substituted ethenyl, propenyl, butenyl, propinyl or butinyl, or represents in each case optionally fluoro-, chloro-, cyano-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, or represents propenyloxy, butenyloxy, propinyloxy, butinyloxy, propenylthio, propadienylthio, butenylthio, propinylthio, butinylthio, propenylamino, butenylamino, propinylamino or butinylamino, or represents dimethylamino, diethylamino or dipropylamino, or represents in each case optionally fluoro-, chloro-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluoro-, chloro-, methyl-, trifluoromethyl-, methoxy- and/or methoxy-carbonyl substituted phenyl, benzyl, phenoxy, benzyloxy, phenylthio, benzylthio, phenylamino or benzylamino, or $R^4$ and $R^5$ together represent optionally branched alkanediyl having 3 to 11 carbon atoms, and also $R^6$, $R^7$ and $R^8$ are identical or different and represent hydrogen, cyano, fluoro, chloro or bromo, or represent in each case optionally fluoro-, chloro-, methoxy- or ethoxy-substituted methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenytoxy, butenyloxy, propinyloxy, butinyloxy, methylthio, ethylthio, n- or i-propylthio, n-, i-, s- or t-butylthio, propenylthio, butenylthio, propinylthio, butinylthio, methylsulphinyl, ethylsulphinyl, methylsulphonyl or ethylsulphonyl, or represent cyclopropyl, the previously known compounds 4,5-dimethoxy-2-(2,5-dimethoxy-phenylsulphonylaminocarbonyl)-2,4-dihydro-3H-1,2,4-triazol-3-one, 4,5-diethoxy-2-(2,5-dimethoxy-phenylsulphonylaminocarbonyl)-2,4-dihydro-3H-1,2,4-triazol-3-one and N-(2,5-dimethoxy-phenylsulphonyl)-1,5-dimethyl-1H-pyrazole-3-carboxamide being excluded by disclaimer.

A very particularly preferred group of compounds according to the invention are the compounds of the formula (I), in which A represents a single bond, Q represents oxygen or sulphur, $R^1$ represents methyl, ethyl, n- or i-propyl, $R^2$ represents chloro or methyl- in each case in position 5 or 6- and $R^3$ represents optionally substituted triazolinyl of the formula below

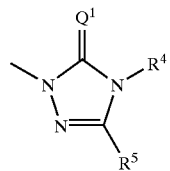

in which $Q^1$ represents oxygen or sulphur, and $R^4$ represents in each case optionally fluoro-, chloro-, cyano-, methoxy- or ethoxy-substituted methyl, ethyl, n- or i-propyl, or represents propenyl or a propinyl, or represents methoxy, ethoxy, n- or i-propoxy, or represents cyclopropyl, and $R^5$ represents hydrogen, chloro or bromo, or represents in each case optionally fluoro-, chloro-, cyano-, methoxy- or ethoxy-substituted methyl, ethyl, n- or i-propyl, or represents in each case optionally fluoro and/or chloro-substituted propenyl or propinyl, or represents in each case optionally fluoro-, chloro-, cyano-, methoxy- or ethoxy-substituted methoxy, ethoxy, n- or i-propoxy, methylthio, ethylthio, n- or i-propylthio, or represents propenyloxy or cyclopropyl.

The radical definitions listed above, whether general or listed in ranges of preference, apply not only to the end products of the formula (I) but also, correspondingly, to the starting materials and/or intermediates required in each case of the preparation. These radical definitions can be combined as desired with one another, thus including combinations between the preferred ranges indicated.

Using, for example, 2-fluoro-6-methoxy-benzenesulphonamide and 5-ethoxy-4-methyl-2-phenoxycarbonyl-2,4-dihydro-3H-1,2,4-triazole-3-thione as starting materials, the course of reaction in the process (a) according to the invention can be illustrated by the following equation:

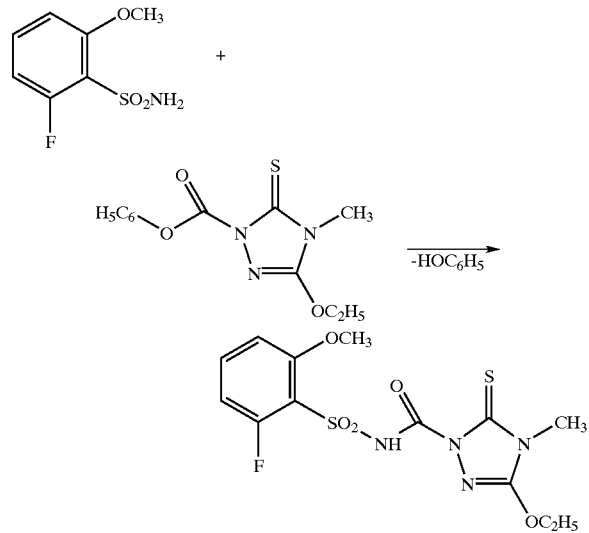

Using, for example, 2-ethoxy-6-methyl-phenylsulphonyl-isothiocyanate and 5-ethyl-4-methoxy-2,4-dihydro-3H-1,2,4-triazol-3-one as starting materials, the course of reaction in the process (b) according to the invention can be illustrated by the following equation:

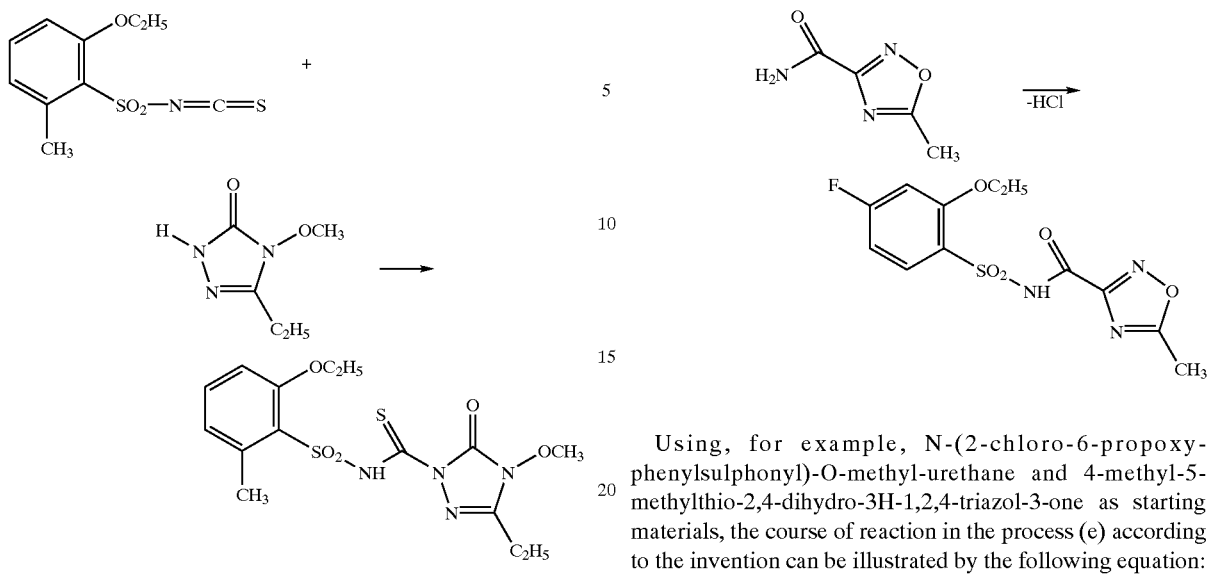

Using, for example, 2-methoxy-3-methyl-benzenesulphochloride, 5-ethylthio-4-methoxy-2,4-dihydro-3H-1,2,4-triazol-3-one and potassium cyanate as starting materials, the course of reaction in the process (c) according to the invention can be illustrated by the following equation:

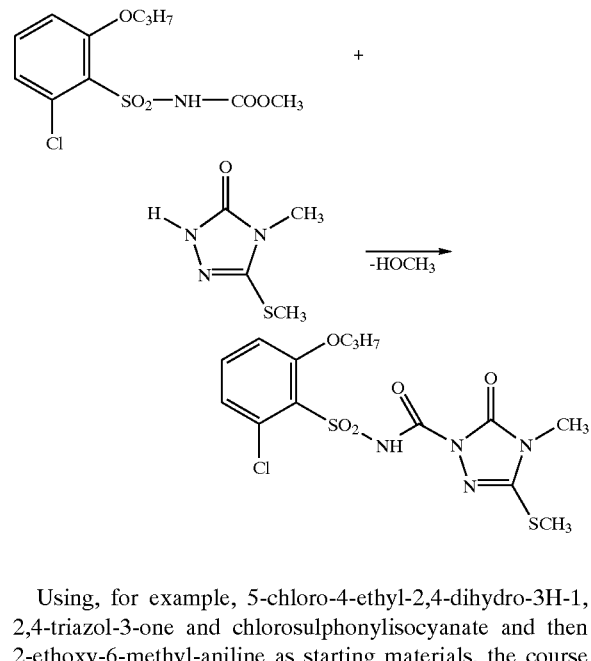

Using, for example, 2-ethoxy-4-fluoro-benzenesulphochloride and 5-methyl-1,2,4-oxadiazole-3-carboxamide as starting materials, the course of reaction in the process (d) according to the invention can be illustrated by the following equation:

Using, for example, N-(2-chloro-6-propoxy-phenylsulphonyl)-O-methyl-urethane and 4-methyl-5-methylthio-2,4-dihydro-3H-1,2,4-triazol-3-one as starting materials, the course of reaction in the process (e) according to the invention can be illustrated by the following equation:

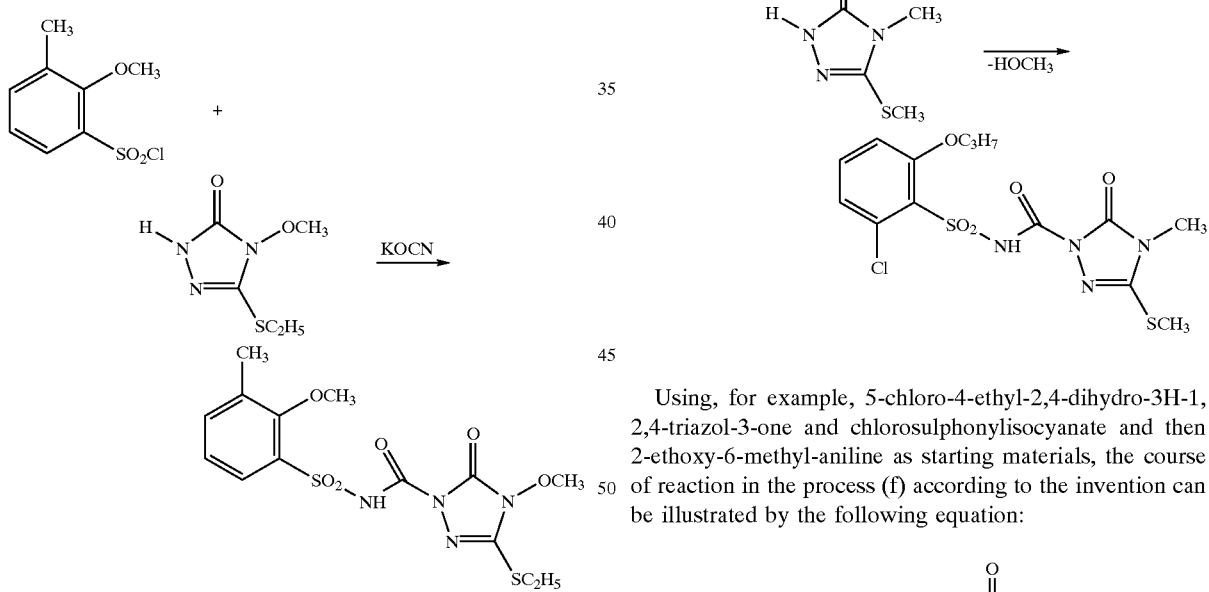

Using, for example, 5-chloro-4-ethyl-2,4-dihydro-3H-1,2,4-triazol-3-one and chlorosulphonylisocyanate and then 2-ethoxy-6-methyl-aniline as starting materials, the course of reaction in the process (f) according to the invention can be illustrated by the following equation:

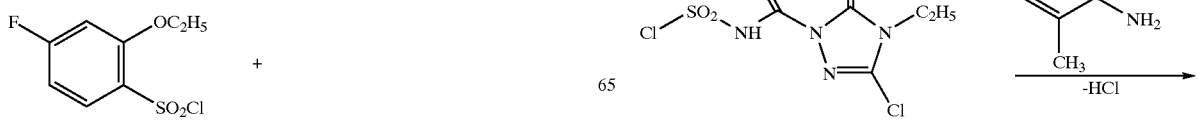

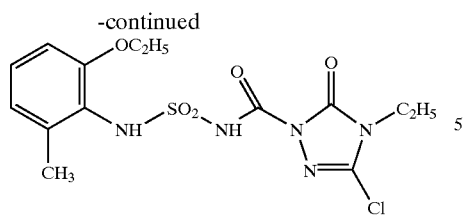

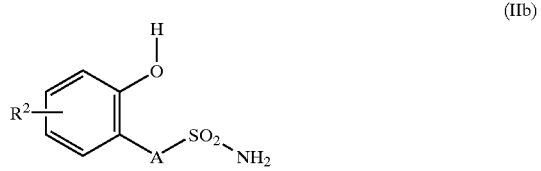

A general definition of the aminosulphonyl compounds to be used as starting materials in the process (a) according to the invention for the preparation of compounds of the formula (I) is given by the formula (II). In the formula (II) A, $R^1$ and $R^2$ preferably or in particular have that meaning which has already been indicated above, in connection with the description of the compounds of the formula (I) to be prepared in accordance with the invention, as being preferable or, respectively, particularly preferable for A, $R^1$ and $R^2$.

The starting materials of the formula (II) are known and/or can be prepared by methods known per se (cf. EP 216504, DE 3208189, EP 44807, EP 23422).

Compounds not yet known from the literature, and which as novel substances are likewise a subject of the present application, are the sulphonamides of the general formula (IIa),

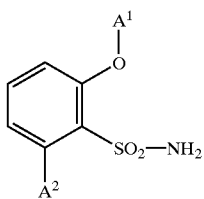

in which $A^1$ represents ethyl, n- or i-propyl, n-, i-, s- or t-butyl, trifluoromethyl, fluoroethyl, chloroethyl, difluoroethyl, trifluoroethyl, chlorotrifluoroethyl, methoxyethyl, ethoxyethyl, allyl, propargyl or benzyl, and $A^2$ represents methyl, ethyl, n- or i-propyl, n-, i-, s- or t-butyl.

The novel sulphonamides of the formula (IIa) are obtained if sulphonyl chlorides of the formula (VIa)

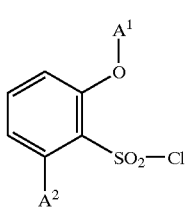

in which $A^1$ and $A^2$ have the meanings given above are reacted with ammonia, optionally in the presence of a diluent, for example water, at temperatures between 0° C. and 50° C. (cf. the Preparation Examples).

The starting materials of the formula (II) can in general be obtained also by reacting phenol derivatives of the formula (IIb)

in which

A and $R^2$ have the meanings given above with alkylating agents of the formula (XI)

$$X—R^1 \qquad (XI)$$

in which $R^1$ has the meaning given above, and

X represents halogen or the group $R^1$—O—$SO_2$—O—, optionally in the presence of an acid acceptor, for example potassium carbonate, and optionally in the presence of a diluent for example toluene, at temperatures between 10° C. and 150° C. (cf. the Preparation Examples).

The phenol derivatives of the formula (IIb) required as precursors are known and/or can be prepared by methods known per se (cf EP 44807, Metalloberfläche [Metal surface]—Angew. Elektrochernie 27 (1973), 217–227— cited in Chemn. Abstracts 79:86733; Preparation Examples).

The alkylating agents of the formula (XI) which are also required as precursors are known synthesis chemicals.

A general definition of the (thio)carboxylic acid derivatives also to be used as starting materials in the process (a) according to the invention for the preparation of the compounds of the formula (I) is given by the formula (III). In the formula (III), Q and $R^3$ preferably or in particular have that meaning which has already been indicated above, in connection with the description of the compounds of the formula (I) to be prepared in accordance with the invention, as being preferable or, respectively, particularly preferable for Q and $R^3$; Z preferably represents fluorine, chlorine, bromine, $C_1$–$C_4$-alkoxy, phenoxy or benzyloxy, and in particular represents chlorine, methoxy, ethoxy or phenoxy.

The starting materials of the formula (III) are known and/or can be prepared by methods known per se (cf. EP 459244, EP 341489, EP 422469, EP 425948, EP 431291, EP 507171, EP 534266).

A general definition of the sulphonyl iso(thio)cyanate to be used as starting materials in the process (b) according to the invention for the preparation of the compounds of the formula (I) is given with the formula (IV). In the formula (IV), A, Q, $R^1$ and $R^2$ preferably or in particular have that meaning which has already been indicated above, in connection with the description of the compounds of the formula (I) to be prepared in accordance with the invention, as being preferable or particularly preferable for A, Q, $R^1$ and $R^2$.

The starting materials of the formula (IV) are known and/or can be prepared by methods known per se (cf. EP 23422, EP 216504).

Compounds not yet known from the literature, and which as novel substances are likewise a subject of the present application, are the sulphonyl iso(thio)cyanates of the general formula (IVa)

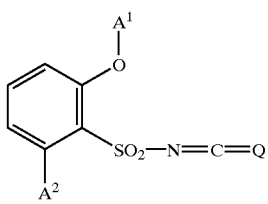

(IVa)

in which

Q represents oxygen or sulphur, $A^1$ represents ethyl, n- or i-propyl, n-, i-, s- or t-butyl, trifluoromethyl, fluoroethyl, chloroethyl, difluoroethyl, trifluoroethyl, chlorotrifluoroethyl, methoxyethyl, ethoxyethyl, allyl, propargyl or benzyl, and $A^2$ represents methyl, ethyl, n- or i-propyl, n-, i-, s- or t-butyl.

The novel sulphonyl iso(thio)cyanates of the formula (IVa) are obtained if sulphonamides of the formula (IIa)—above—are reacted with phosgene or, respectively, thiophosgene, optionally in the presence of an alkyl isocyanate, for example butyl isocyanate, optionally in the presence of a reaction auxiliary, for example diazabicyclo [2.2.2]octane, and in the presence of a diluent, for example toluene, xylene or chlorobenzene, at temperatures between 80° C. and 150° C., and, after the end of the reaction, the volatile components are distilled off under reduced pressure.

A general definition of the heterocycles also to be used as starting materials in the processes (b), (c), (e) and (f) according to the invention for the preparation of the compounds of the formula (I) is given by the formula (V). In the formula (V), $R^3$ preferably or in particular has that meaning which has already been indicated above, in connection with the description of the compounds of the formula (I) to be prepared in accordance with the invention, as being preferable or particularly preferable for $R^3$.

The starting materials of the formula (V) are known and/or can be prepared by methods known per se (cf EP 341489, EP 422469, EP 425948, EP 431291, EP 507171, EP 534266).

A general definition of the chlorosulphonyl compounds to be used as starting materials in the processes (c) and (d) according to the invention for the preparation of compounds of the formula (I) is given by the formula (VI). In the formula (VI), A, $R^1$ and $R^2$ preferably or in particular have that meaning which has already been indicated above, in connection with the description of the compounds of the formula (I) to be prepared in accordance with the invention, as being preferable or particularly preferable for A, $R^1$ and $R^2$.

The starting materials of the formula (VI) are known and/or can be prepared by methods known per se (cf. EP 511826, DE 3208189, EP23422).

Compounds not yet known from the literature, which as novel substances are likewise a subject of the present application, are the sulphonyl chlorides of the formula (VIa)

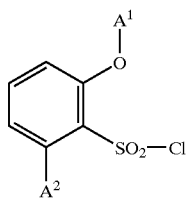

(VIa)

in which $A^1$ represents ethyl, n- or i-propyl, n-, i-, s- or t-butyl, trifluoromethyl, fluoroethyl, chloroethyl, difluoroethyl, trifluoroethyl, chlorotrifluoroethyl, methoxyethyl, ethoxyethyl, allyl, propargyl or benzyl, and $A^2$ represents methyl, ethyl, n- or i-propyl, n-, i-, s- or t-butyl.

The novel sulphonyl chlorides of the formula (VIa) are obtained if aniline derivatives of the formula (XII)

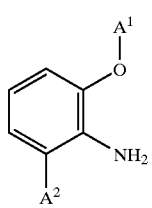

(XII)

in which $A^1$ and $A^2$ have the meanings given above are reacted with an alkali metal nitrite, for example sodium nitrite, in the presence if hydrochloric acid at temperatures between −10° C. and +10° C., and the diazonium salt solution thus obtained is reacted with sulphur dioxide in the presence of a diluent, for example dichloromethane or 1,2-dichloro-ethane, and in the presence of a catalyst, for example copper(I) chloride, optionally in the presence of a further catalyst, for example dodecyltrimethylammonium bromide, at temperatures between −10° C. and +50° C. (cf. the Preparation Examples).

The aniline derivatives of the formula (XII) required as precursors are known and/or can be prepared by methods known per se (cf. EP 511826, U.S. Pat. No. 4,992,091, EP 185128, DE 2405479, Preparation Examples).

The abovementioned novel benzenesulphonic acid derivatives of the formulae (IIa), (IVa) and (VIa) can be defined comprehensively by the following formula (XIII):

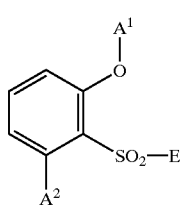

(XIII)

in which

E represents —NH$_2$, —N=C=Q or —Cl, where

Q represents O or S, and also $A^1$ represents ethyl, n- or i-propyl, n-, i-, s- or t-butyl, trifluoromethyl, fluoroethyl, chloroethyl, difluoroethyl, trifluoroethy, chlorotrifluoroethyl, methoxyethyl, ethoxyethyl, allyl, propargyl or benzyl, and $A^2$ represents methyl, ethyl, n- or i-propyl, n-, i-, s- or t-butyl.

A general definition of the (thio)carboxamides to be used as starting materials in the process (d) according to the invention for the preparation of the compounds of the formula (I) is given by the formula (VIII). In the formula (VIII), Q and $R^3$ preferably or in particular have that meaning which has already been indicated above, in connection with a description of the compounds of the formula (I) to be prepared in accordance with the invention, as being preferable or particularly preferable for Q and $R^3$.

The starting materials of the formula (VIII) are known and/or can be prepared by methods known per se (cf. EP 459244).

A general definition of the sulphonylamino(thio)carbonyl compounds to be used as starting materials in the process (e) according to the invention for the preparation of the compounds of the formula (I) is given by the formula (IX). In the formula (IX), A, Q, $R^1$ and $R^2$ preferably or in particular have that meaning which has already been indicated above, in connection with the description of the compounds of the formula (I) to be prepared in accordance with the invention, as being preferable or particularly preferable for A, Q, $R^1$ and $R^2$; Z preferably represents fluoro, chloro, bromo, $C_1$–$C_4$-alkoxy, phenoxy or benzyloxy, and in particular represents chlorine, methoxy, ethoxy or phenoxy.

A general definition of the benzene derivatives to be used as starting materials in the process (f) according to the invention for the preparation of the compounds of the formula (I) is given by the formula (X). In the formula (X), A, $R^1$ and $R^2$ preferably or in particular have that meaning which has already been indicated above, in connection with the description of the compounds of the formula (I) to be prepared in accordance with the invention, as being preferable or particularly preferable for A, $R^1$ and $R^2$.

Starting materials of the formula (X) are known and/or can be prepared by methods known per se (cf. EP 511826, U.S. Pat. No. 4,992,091, EP 185128, DE 2405479, Preparation Examples).

The processes (a), (b), (c), (d), (e) and (f) according to the invention for the preparation of the novel compounds of the formula (I) are preferably carried out using diluents. Suitable diluents in this context are virtually all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene; ethers such as diethyl ether and dibutyl ether, glycol dimethyl ether and diglycol dimethyl ether, tetrahydrofuran and dioxanes; ketones such as acetone, methyl ethyl ketone, methyl isopropyl ketone and methyl isobutyl ketone; esters such as methyl acetate and ethyl acetate; nitrites, for example acetonitrile and propionitrile; amides, for example dimethylformamide, dimethylacetamide and N-methylpyrrolidone, and also dimethyl sulphoxide, tetramethylene sulphone and hexamethylphosphoric triamide.

As reaction auxiliaries and/or as acid acceptors in the processes (a), (b), (c), (d), (e) and (f) according to the invention it is possible to employ all acid-binding agents which can customarily be used for such reactions. Preferred among suitable examples are alkali metal hydroxides, for example sodium hydroxide and potassium hydroxide, alkaline earth metal hydroxides, for example calcium hydroxide, alkali metal carbonates and alcoholates, such as sodium carbonate and potassium carbonate, sodium tert-butylate and potassium tert-butylate, and also basic nitrogen compounds; such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo [5.4.0]-undec-7-ene (DBU) and 1,4-diazabicyclo-[2.2.2]-octane (DABCO).

The reaction temperatures in the processes (a), (b), (c), (d), (e) and (f) according to the invention can be varied within a relatively wide range. They are in general carried out at temperatures of between −20° C. and +150° C., preferably at temperatures between 0° C. and +100° C.

The processes (a), (b), (c), (d), (e) and (f) according to the invention are generally carried out under atmospheric pressure. However it is also possible to operate under increased or reduced pressure.

For carrying out processes (a), (b), (c), (d), (e) and (f) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Working up in the case of the processes (a), (b), (c), (d), (e) and (f) according to the invention is in each case by customary methods (cf the Preparation Examples).

Salts of the compounds of the general formula (I) according to the invention can be prepared if desired. Such salts are obtained in a simple manner by customary methods of forming salts, for example by dissolving or dispersing a compound of the formula (I) in an appropriate solvent, for example methylene chloride, acetone, tert-butyl methyl ether or toluene, and adding an appropriate base. The salts can then—if desired after prolonged stirring—be isolated by concentration or filtration with suction.

The active compounds according to the invention can be used as defoliants, desiccants, agents for destroying broad-leaved plants and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are preferably suitable for combating monoctyledon and dicotyledon broad-leaved weeds, both pre-emergence and post-emergence. They exhibit strong herbicidal activity and a broad spectrum action when used on the soil and on above-ground parts of the plants.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:
for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methyl cellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example anilides, for example diflufenican and propanil; arylcarboxylic acids, for example dichloropicolinic acid, dicamba and picloram; aryloxyalkanoic acids, for example 2,4-D, 2,4-DB, 2,4-DP, fluroxypyr, MCPA, MCPP and triclopyr; aryloxy-phenoxy-alkanoic esters, for example diclofop-methyl, fenoxaprop-ethyl, fluazifop-butyl, haloxyfop-methyl and quizalofop-ethyl; azinones, for example chloridazon and norflurazon; carbamates, for example chlorpropham, desmedipham, phenmedipham and propham; chloroacetanilides, for example alachlor, acetochlor, butachlor, metazachlor, metolachlor, pretilachlor and propachlor; dinitroanilines, for example oryzalin, pendimethalin and trifluralin; diphenyl ethers, for example acifluorfen, bifenox, fluoroglycofen, fomesafen, halosafen, lactofen and oxyfluorfen; ureas, for example chlorotoluron, diuron, fluometuron, isoproturon, linuron and methabenz-thiazuron; hydroxylamines, for example alloxydim, clethodim, cycloxydim, sethoxydim and tralkoxydim; imidazolinones, for example imazethapyr, imazamethabenz, imazapyr and imazaquin; nitriles, for example bromoxynil, dichlobenil and ioxynil; oxyacetamides, for example mefen-acet; sulphonyl-ureas, for example amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, for example butylate, cycloate, diallate, EPTC, esprocarb, molinate, prosulfocarb, thiobencarb and triallate; triazines, for example atrazine, cyanazine, simazine, simetryne, terbutryne and terbutylazine; triazinones, for example hexazinone, metamitron and metribuzin; others, for example aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 and 10 kg of active compound per hectare of soil surface, preferably between 5 g and 5 kg per ha.

The preparation and use of the active compounds according to the invention can be seen from the following examples.

PREPARATION EXAMPLES

Example 1

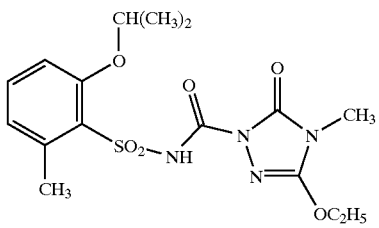

(Process (a))

A mixture of 2.5 g (10 mmol) of 5-ethoxy-4-methyl-2-phenoxycarbonyl-2,4-dihydro-3H-1,2,4-triazol-3-one, 2.3 g (10 mmol) of 2-isopropoxy-6-methyl-benzenesulphonamide, 1.5 g (10 mmol) of diazabicyclo[5.4.0]undec-7-ene (DBU) and 50 ml of acetonitrile is stirred at 20° C. for 5 hours. It is then concentrated under a water pump vacuum and the residue is stirred with 50 ml of 1N hydrochloric acid, the mixture is filtered with suction, the filter product is stirred with diethyl ether and the mixture is again filtered with suction.

2.4 g (60% of theory) of 5-ethoxy-4-methyl-2-(2-isopropoxy-6-methyl-phenylsulphonyl-aminocarbonyl)-2,4-dihydro-3H-1,2,4-triazol-3-one are obtained of melting point 155° C.

Example 2

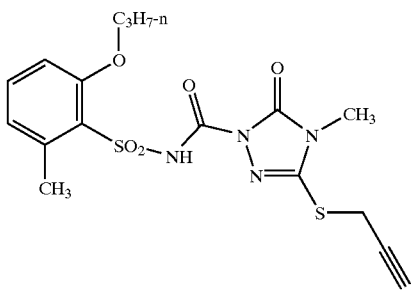

(Process (c))

A mixture of 1.7 g (10 mmol) of 4-methyl-5-propargylthio-2,4-dihydro-3H-1,2,4-triazol-3-one, 1.3 g (20 mmol) of sodium cyanate, 2.5 g (10 mmol) of 2-methyl-6-n-propoxy-benzenesulphochloride and 50 ml of acetonitrile is heated under reflux for 3 hours. It is then concentrated under a water pump vacuum, the residue is stirred with 1N hydrochloric acid and the mixture is subjected three times to extraction with 50 ml of methylene chloride each time. The combined organic extraction solutions are concentrated, the residue is digested with isopropanol and the crystalline product is isolated by filtration with suction.

2.2 g (52% of theory) of 4-methyl-5-propargylthio-2-(2-methyl-6-n-propoxy-phenylsulphonyl-aminocarbonyl)-2,4-dihydro-3H-1,2,4-triazol-3-one are obtained of melting point 151° C.

Example 3

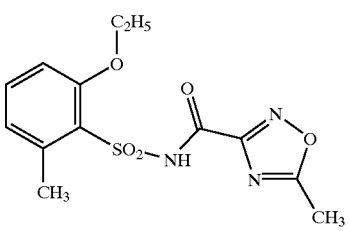

(Process (d))

A mixture of 3.2 g (25 mmol) of 5-methyl-1,2,4-oxadiazole-3-carboxamide, 4.2g (75 mmol) of potassium hydroxide (powder) and 200 ml of dioxane is stirred at 60° C. for 30 minutes. It is then concentrated to about half its volume under a water pump vacuum, and a solution of 7 g (30 mmol) of 2-ethoxy-6-methyl-benzenesulphochloride in 10 ml of dioxane is added dropwise at about 20° C. The reaction mixture is then stirred at 20° C. for about 15 hours more. It is then concentrated under a water pump vacuum, the residue is stirred with 50 ml of 1N hydrochloric acid and the crystalline product is isolated by filtration with suction. 4.0 g (49% of theory) of N-(2-ethoxy-6-methyl-phenylsulphonyl)-5-methyl-1,2,4-oxadiazole-3-carboxamide are obtained of melting point 168° C.

Example 4

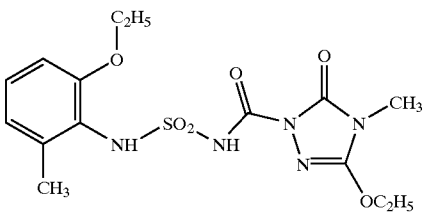

(Process (f))

1.7 g (12 mmol) of chlorosulphonyl isocyanate are added to a solution, cooled to 5° C., of 1.4 g (10 mmol) of 5-ethoxy-4-methyl-2,4-dihydro-3H-1,2,4-triazol-3-one in 50 ml of methylene chloride, and then a solution of 1.5 g (10 mmol) of 2-ethoxy-6-methyl-aniline and 1.0 g (10 mmol) of triethylamine in 10 ml of methylene chloride is added dropwise, likewise at 5° C. The reaction mixture is then stirred at about 20° C. for 15 hours. Subsequently, 100 ml of 1N hydrochloric acid are added. After a thorough stirring, the organic phase is separated off, dried over sodium sulphate and filtered. The filtrate is concentrated under a water pump vacuum, the residue is digested with isopropanol and the crystalline product is isolated by filtration with suction.

1.8 g (45% of theory) of 5-ethoxy-4-methyl-2-(2-ethoxy-6-methyl-phenyl-aminosulphonyl-aminocarbonyl)-2,4-dihydro-3H-1,2,4-triazol-3-one are obtained of melting point 147° C.

In analogy to Example 1 to 4 and in accordance with the general description of the preparation processes according to the invention, it is also possible, for example, to prepare the compounds of the formula (I) listed in Table 1 below (showing Examples Nos. 5–965), as well as the compounds of the formula (IA) listed in Table IA thereafter (showing Examples Nos. 966–1637):

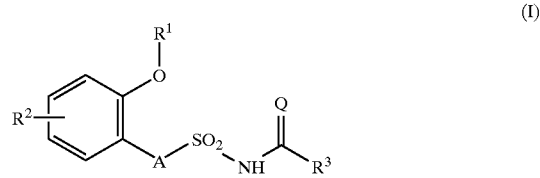

TABLE 1

Examples of the compounds of the formula (I)

| Ex. No. | A | Q | $R^1$ | (position-) $R^2$ | $R^3$ | Melting point (° C.) |
|---|---|---|---|---|---|---|
| 5 | — | O | $n$-$C_3H_7$ | (6-) $CH_3$ | 3-methyl-1,2,4-oxadiazol-5-yl (5-$CH_3$) | 117 |
| 6 | — | O | $C_2H_5$ | (6-) Cl | 3-methyl-1,2,4-oxadiazol-5-yl (5-$CH_3$) | 156 |
| 7 | — | O | $C_2H_5$ | (6-) $CH_3$ | 2,4-dimethyl-5-ethyl-3-oxo-2,4-dihydro-1,2,4-triazol-yl | 110 |
| 8 | — | O | $C_2H_5$ | (6-) $CH_3$ | 2,4-dimethyl-5-methylthio-3-oxo-2,4-dihydro-1,2,4-triazol-yl | 141 |
| 9 | — | O | $C_2H_5$ | (6-) $CH_3$ | 2,4-dimethyl-5-ethoxy-3-oxo-2,4-dihydro-1,2,4-triazol-yl | 162 |
| 10 | — | O | $n$-$C_3H_7$ | (6-) $CH_3$ | 2,4-dimethyl-5-ethyl-3-oxo-2,4-dihydro-1,2,4-triazol-yl | 126 |

TABLE 1-continued

Examples of the compounds of the formula (I)

| Ex. No. | A | Q | R¹ | (position-) R² | R³ | Melting point (° C.) |
|---|---|---|---|---|---|---|
| 11 | — | O | n-C₃H₇ | (6-) CH₃ | 1,4-dimethyl-5-(methylthio)-1,2,4-triazol-3(2H)-one | 150 |
| 12 | — | O | n-C₃H₇ | (6-) CH₃ | 5-ethoxy-1,4-dimethyl-1,2,4-triazol-3(2H)-one | 129 |
| 13 | — | O | CH₃ | (6-) CH₃ | 5-ethyl-1,4-dimethyl-1,2,4-triazol-3(2H)-one | 153 |
| 14 | — | O | CH₃ | (6-) CH₃ | 1,4-dimethyl-5-(methylthio)-1,2,4-triazol-3(2H)-one | 167 |
| 15 | — | O | CH₃ | (6-) CH₃ | 5-ethoxy-1,4-dimethyl-1,2,4-triazol-3(2H)-one | 167 |
| 16 | — | O | i-C₃H₇ | (6-) CH₃ | 5-ethyl-1,4-dimethyl-1,2,4-triazol-3(2H)-one | 125 |
| 17 | — | O | i-C₃H₇ | (6-) CH₃ | 1,4-dimethyl-5-(methylthio)-1,2,4-triazol-3(2H)-one | 131 |
| 18 | — | O | C₂H₅ | (5-) CH₃ | 1,4-dimethyl-5-(methylthio)-1,2,4-triazol-3(2H)-one | 222 |

TABLE 1-continued

Examples of the compounds of the formula (I)

| Ex. No. | A | Q | R¹ | (position-) R² | R³ | Melting point (° C.) |
|---|---|---|---|---|---|---|
| 19 | — | O | $C_2H_5$ | (5-) $CH_3$ | 1,4-dimethyl-5-ethoxy-1,2,4-triazol-3(2H)-one-2-yl | 139 |
| 20 | — | O | $C_2H_5$ | (4-) $CH_3$ | 1,4-dimethyl-5-methylthio-1,2,4-triazol-3(2H)-one-2-yl | 189 |
| 21 | — | O | $C_2H_5$ | (5-) $CH_3$ | 1,4-dimethyl-5-ethyl-1,2,4-triazol-3(2H)-one-2-yl | 131 |
| 22 | — | O | $-C_2H_4-OC_2H_5$ | (6-) $CH_3$ | 1,4-dimethyl-5-ethyl-1,2,4-triazol-3(2H)-one-2-yl | 118 |
| 23 | — | O | $-CH_2CH_2Cl$ | (6-) $CH_3$ | 1,4-dimethyl-5-ethyl-1,2,4-triazol-3(2H)-one-2-yl | 137 |
| 24 | — | O | $-CH_2CH_2Cl$ | (6-) $CH_3$ | 1,4-dimethyl-5-ethoxy-1,2,4-triazol-3(2H)-one-2-yl | 149 |
| 25 | — | O | $i-C_3H_7$ | (5-) $CH_3$ | 1,4-dimethyl-5-ethoxy-1,2,4-triazol-3(2H)-one-2-yl | 125 |
| 26 | — | O | $i-C_3H_7$ | (5-) $CH_3$ | 1,4-dimethyl-5-methylthio-1,2,4-triazol-3(2H)-one-2-yl | 140 |

TABLE 1-continued

Examples of the compounds of the formula (I)

| Ex. No. | A | Q | R¹ | (position-) R² | R³ | Melting point (° C.) |
|---|---|---|---|---|---|---|
| 27 | — | O | n-C₃H₇ | (5-) CH₃ | triazolinone with N-CH₃, N-CH₃, C₂H₅ | 119 |
| 28 | — | O | n-C₃H₇ | (5-) CH₃ | triazolinone with N-CH₃, N-CH₃, OC₂H₅ | 134 |
| 29 | — | O | n-C₃H₇ | (5-) CH₃ | triazolinone with N-CH₃, N-CH₃, SCH₃ | 110 |
| 30 | — | O | C₂H₅ | (6-) CH₃ | triazolinone with N-CH₃, N-CH₃, CH₃ | 108 |
| 31 | — | O | C₂H₅ | (6-) CH₃ | triazolinone with N-CH₃, N-CH₃, OCH₃ | 173 |
| 32 | — | O | C₂H₅ | (6-) CH₃ | triazolinone with N-CH₃, N-CH₃, CH₂OCH₃ | 119 |
| 33 | — | O | C₂H₅ | (6-) CH₃ | triazolinone with N-CH₃, N-CH₃, OC₃H₇ | 121 |
| 34 | — | O | C₂H₅ | (6-) CH₃ | triazolinone with N-CH₃, N-CH₃, CH(CH₃)₂ | 109 |

TABLE 1-continued

Examples of the compounds of the formula (I)

| Ex. No. | A | Q | R¹ | (position-) R² | R³ | Melting point (° C.) |
|---|---|---|---|---|---|---|
| 35 | — | O | $C_2H_5$ | (6-) $CH_3$ | 1,2,4-triazol-3(2H)-one, 2-methyl-4-methyl-5-SC₂H₅ | 111 |
| 36 | — | O | n-$C_3H_7$ | (6-) $CH_3$ | 1,2,4-triazol-3(2H)-one, 2-methyl-4-methyl-5-OC₃H₇ | 91 |
| 37 | — | O | n-$C_3H_7$ | (6-) $CH_3$ | 1,2,4-triazol-3(2H)-one, 2-methyl-4-methyl-5-CH(CH₃)₂ | 130 |
| 38 | — | O | n-$C_3H_7$ | (6-) $CH_3$ | 1,2,4-triazol-3(2H)-one, 2-methyl-4-methyl-5-CH₂CH₂CH₃ | 126 |
| 39 | — | O | n-$C_3H_7$ | (6-) $CH_3$ | 1,2,4-triazol-3(2H)-one, 2-methyl-4-methyl-5-CH₂OCH₃ | 101 |
| 40 | — | O | n-$C_3H_7$ | (6-) $CH_3$ | 1,2,4-triazol-3(2H)-one, 2-methyl-4-methyl-5-OCH₃ | 152 |
| 41 | — | O | n-$C_3H_7$ | (6-) $CH_3$ | 1,2,4-triazol-3(2H)-one, 2-methyl-4-methyl-5-CH₃ | 100 |
| 42 | — | O | n-$C_3H_7$ | (6-) $CH_3$ | 1,2,4-triazol-3(2H)-one, 2-methyl-4-methyl-5-SC₂H₅ | 120 |

TABLE 1-continued

Examples of the compounds of the formula (I)

| Ex. No. | A | Q | R¹ | (position-) R² | R³ | Melting point (° C.) |
|---|---|---|---|---|---|---|
| 43 | — | O | n-C₃H₇ | (6-) CH₃ | (1-methyl-4-ethyl-5-methoxy-1,2,4-triazol-3(4H)-one) | 117 |
| 44 | — | O | n-C₃H₇ | (6-) CH₃ | (1-methyl-4-ethoxy-5-ethyl-1,2,4-triazol-3(4H)-one) | 126 |
| 45 | — | O | n-C₃H₇ | (6-) CH₃ | (1-methyl-4-ethyl-5-ethoxy-1,2,4-triazol-3(4H)-one) | 113 |
| 46 | — | O | i-C₃H₇ | (6-) CH₃ | (1-methyl-4-methyl-5-methoxymethyl-1,2,4-triazol-3(4H)-one) | 130 |
| 47 | — | O | i-C₃H₇ | (6-) CH₃ | (1-methyl-4-methyl-5-methoxy-1,2,4-triazol-3(4H)-one) | 139 |
| 48 | — | O | i-C₃H₇ | (6-) CH₃ | (1,4,5-trimethyl-1,2,4-triazol-3(4H)-one) | 121 |
| 49 | — | O | i-C₃H₇ | (6-) CH₃ | (1,4-dimethyl-5-propoxy-1,2,4-triazol-3(4H)-one) | 119 |
| 50 | — | O | i-C₃H₇ | (6-) CH₃ | (1,4-dimethyl-5-isopropyl-1,2,4-triazol-3(4H)-one) | 128 |

TABLE 1-continued

Examples of the compounds of the formula (I)

| Ex. No. | A | Q | R¹ | (position-) R² | R³ | Melting point (° C.) |
|---|---|---|---|---|---|---|
| 51 | — | O | i-$C_3H_7$ | (6-) $CH_3$ | 1-methyl-4-methyl-5-propyl-1,2,4-triazol-3(4H)-one | 134 |
| 52 | — | O | i-$C_3H_7$ | (6-) $CH_3$ | 1-methyl-4-methyl-5-(ethylthio)-1,2,4-triazol-3(4H)-one | 130 |
| 53 | — | O | i-$C_3H_7$ | (6-) $CH_3$ | 1-methyl-4-methyl-5-propyl-1,2,4-triazol-3(4H)-one | 117 |
| 54 | — | O | i-$C_3H_7$ | (6-) $CH_3$ | 1-methyl-4-ethyl-5-ethoxy-1,2,4-triazol-3(4H)-one | 134 |
| 55 | — | O | i-$C_3H_7$ | (6-) $CH_3$ | 1-methyl-4-methyl-5-methoxy-1,2,4-triazol-3(4H)-one | 141 |
| 56 | — | O | i-$C_3H_7$ | (6-) $CH_3$ | 1-methyl-4-ethoxy-5-ethyl-1,2,4-triazol-3(4H)-one | 132 |
| 57 | — | O | i-$C_3H_7$ | (6-) $CH_3$ | 1-methyl-4-methyl-5-isopropoxy-1,2,4-triazol-3(4H)-one | 166 |
| 58 | — | O | i-$C_3H_7$ | (6-) $CH_3$ | 1-methyl-4-cyclopropyl-5-(methoxymethyl)-1,2,4-triazol-3(4H)-one | 118 |

TABLE 1-continued

Examples of the compounds of the formula (I)

| Ex. No. | A | Q | R¹ | (position-) R² | R³ | Melting point (° C.) |
|---|---|---|---|---|---|---|
| 59 | — | O | i-C₃H₇ | (6-) CH₃ | 4-methyl-2-methyl-5-(prop-2-yn-1-ylthio)-2,4-dihydro-3H-1,2,4-triazol-3-one | 150 |
| 60 | — | O | i-C₃H₇ | (6-) CH₃ | 4-cyclopropyl-5-ethoxy-2-methyl-2,4-dihydro-3H-1,2,4-triazol-3-one | 144 |
| 61 | — | O | i-C₃H₇ | (6-) CH₃ | 5-bromo-4-cyclopropyl-2-methyl-2,4-dihydro-3H-1,2,4-triazol-3-one | 170 |
| 62 | — | O | i-C₃H₇ | (6-) CH₃ | 2,4-dimethyl-5-(2,2,2-trifluoroethoxy)-2,4-dihydro-3H-1,2,4-triazol-3-one | 120 |
| 63 | — | O | n-C₃H₇ | (6-) CH₃ | 5-isopropoxy-2,4-dimethyl-2,4-dihydro-3H-1,2,4-triazol-3-one | 124 |
| 64 | — | O | n-C₃H₇ | (6-) CH₃ | 4-cyclopropyl-5-(methoxymethyl)-2-methyl-2,4-dihydro-3H-1,2,4-triazol-3-one | 125 |
| 65 | — | O | n-C₃H₇ | (6-) CH₃ | 4-cyclopropyl-5-ethoxy-2-methyl-2,4-dihydro-3H-1,2,4-triazol-3-one | 116 |
| 66 | — | O | n-C₃H₇ | (6-) CH₃ | 5-bromo-4-cyclopropyl-2-methyl-2,4-dihydro-3H-1,2,4-triazol-3-one | 152 |

TABLE 1-continued
Examples of the compounds of the formula (I)
| Ex. No. | A | Q | R¹ | (position-) R² | R³ | Melting point (° C.) |
|---|---|---|---|---|---|---|
| 67 | — | O | n-C₃H₇ | (6-) CH₃ | 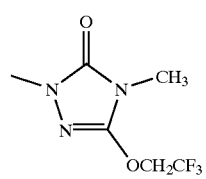 | 143 |
| 68 | — | O | C₂H₅ | (6-) CH₃ | 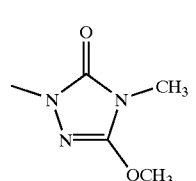 | 160 |
| 69 | — | O | C₂H₅ | (6-) CH₃ | 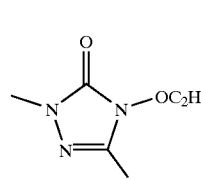 | 133 |
| 70 | — | O | C₂H₅ | (6-) CH₃ | 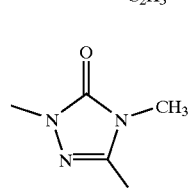 | 97 |
| 71 | — | O | C₂H₅ | (6-) CH₃ | 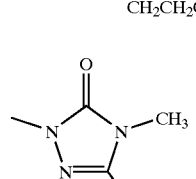 | 96 |
| 72 | — | O | C₂H₅ | (6-) CH₃ | 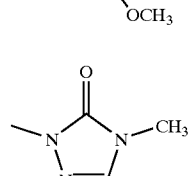 | 156 |
| 73 | — | O | C₂H₅ | (6-) CH₃ | 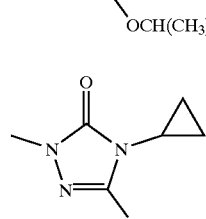 | 145 |
| 74 | — | O | C₂H₅ | (6-) CH₃ | 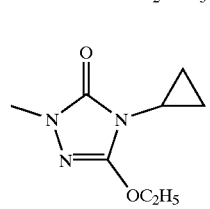 | 120 |

TABLE 1-continued
Examples of the compounds of the formula (I)
| Ex. No. | A | Q | R¹ | (position-) R² | R³ | Melting point (° C.) |
|---|---|---|---|---|---|---|
| 75 | — | O | C₂H₅ | (6-) CH₃ | 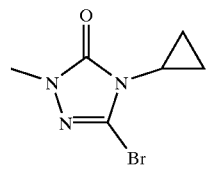 | 125 |
| 76 | — | O | C₂H₅ | (6-) CH₃ | 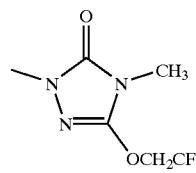 | 140 |
| 77 | — | O | H | (6-) CH₃ | 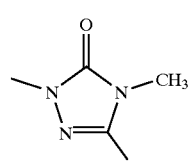 | 88 |
| 78 | — | O | C₂H₅ | (5-) CH₃ | 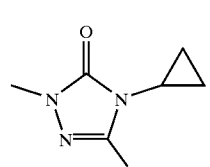 | 130 |
| 79 | — | O | n-C₃H₇ | (6-) CH₃ | 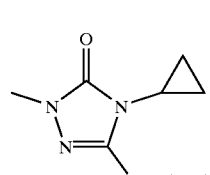 | 141 |
| 80 | — | O | n-C₃H₇ | (6-) CH₃ | 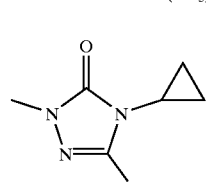 | 98 |
| 81 | — | O | n-C₃H₇ | (6-) CH₃ | 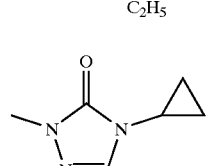 | 141 |
| 82 | — | O | n-C₃H₇ | (6-) CH₃ | 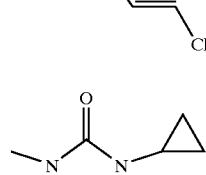 | 101 |

TABLE 1-continued

Examples of the compounds of the formula (I)

| Ex. No. | A | Q | R¹ | (position-) R² | R³ | Melting point (° C.) |
|---|---|---|---|---|---|---|
| 83 | — | O | n-C₃H₇ | (6-) CH₃ | ![structure: 1,2,4-triazol-3(2H)-one with N-CH₃, N-CH₃, and OCH₂CF₂CHF₂] | 136 |
| 84 | — | O | n-C₃H₇ | (6-) CH₃ | ![structure: triazolone with N-CH₃, N-C₂H₅, OCH(CH₃)₂] | 96 |
| 85 | — | O | n-C₃H₇ | (6-) CH₃ | ![structure: triazolone with N-CH₃, N-CH₃, O-CH(CH₃)(C₂H₅)] | 90 |
| 86 | — | O | n-C₃H₇ | (6-) CH₃ | ![structure: triazolone with N-CH₃, N-CH₃, O-CH₂C₆H₅] | 136 |
| 87 | — | O | C₂H₅ | (6-) CH₃ | ![structure: triazolone with N-CH₃, N-CH₃, S-CH₂C≡CH] | 122 |
| 88 | — | O | C₂H₅ | (6-) CH₃ | ![structure: triazolone with N-CH₃, N-cyclopropyl, OCH(CH₃)₂] | 154 |
| 89 | — | O | i-C₃H₇ | (6-) CH₃ | ![structure: triazolone with N-CH₃, N-cyclopropyl, OCH(CH₃)₂] | 139 |

TABLE 1-continued

Examples of the compounds of the formula (I)

| Ex. No. | A | Q | $R^1$ | (position-) $R^2$ | $R^3$ | Melting point (° C.) |
|---|---|---|---|---|---|---|
| 90 | — | O | $C_2H_5$ | (6-) $CH_3$ | 1-methyl-4-cyclopropyl-5-ethyl-1,2,4-triazol-3(4H)-one-2-yl | 142 |
| 91 | — | O | $C_2H_5$ | (6-) $CH_3$ | 1-methyl-4-cyclopropyl-5-(1-propenyl)-1,2,4-triazol-3(4H)-one-2-yl | 153 |
| 92 | — | O | $C_2H_5$ | (6-) $CH_3$ | 1,4-dimethyl-5-($OC_2H_4OCH_3$)-1,2,4-triazol-3(4H)-one-2-yl | 145 |
| 93 | — | O | $C_2H_5$ | (6-) $CH_3$ | 1,4-dimethyl-5-($OCH_2CF_2CHF_2$)-1,2,4-triazol-3(4H)-one-2-yl | 132 |
| 94 | — | O | $C_2H_5$ | (6-) $CH_3$ | 1-methyl-4-allyl-5-($OCH_2CF_3$)-1,2,4-triazol-3(4H)-one-2-yl | 141 |
| 95 | — | O | $C_2H_5$ | (6-) $CH_3$ | 1-methyl-4-ethyl-5-($OCH(CH_3)_2$)-1,2,4-triazol-3(4H)-one-2-yl | 130 |
| 96 | — | O | $CH_3$ | (5-) $CH_3$ | 1,4-dimethyl-5-($OC_3H_7$)-1,2,4-triazol-3(4H)-one-2-yl | 156 |
| 97 | — | O | $CH_3$ | (5-) $CH_3$ | 1,4-dimethyl-5-ethyl-1,2,4-triazol-3(4H)-one-2-yl | 177 |

TABLE 1-continued

Examples of the compounds of the formula (I)

| Ex. No. | A | Q | R¹ | (position-) R² | R³ | Melting point (° C.) |
|---|---|---|---|---|---|---|
| 98 | — | O | CH₃ | (4-) CH₃ | triazolinone with N-CH₃, C₂H₅ | 115 |
| 99 | — | O | CH₃ | (4-) CH₃ | triazolinone with N-CH₃, SC₂H₅ | 166 |
| 100 | — | O | CH₃ | (3-) CH₃ | triazolinone with N-CH₃, OC₃H₇ | 162 |
| 101 | — | O | CH₃ | (3-) CH₃ | triazolinone with N-CH₃, OC₃H₇ | 143 |
| 102 | — | O | CH₃ | (3-) CH₃ | triazolinone with N-CH₃, OCH₃ | 165 |
| 103 | — | O | CHF₂ | (5-) CH₃ | triazolinone with N-CH₃, OCH₃ | 176 |
| 104 | — | O | CHF₂ | (5-) CH₃ | triazolinone with N-CH₃, OC₃H₇-n | 119 |
| 105 | — | O | CHF₂ | (5-) CH₃ | triazolinone with N-CH₃, OC₂H₅ | 126 |

TABLE 1-continued

Examples of the compounds of the formula (I)

| Ex. No. | A | Q | R¹ | (position-) R² | R³ | Melting point (° C.) |
|---|---|---|---|---|---|---|
| 106 | — | O | $CHF_2$ | (5-) $CH_3$ | triazolinone with $N$-$CH_3$, $N$-$CH_3$, $SC_2H_5$ | 151 |
| 107 | — | O | $CHF_2$ | (5-) $CH_3$ | triazolinone with $N$-$CH_3$, $N$-$CH_3$, $SCH_3$ | 188 |
| 108 | — | O | $CHF_2$ | (5-) $CH_3$ | triazolinone with $N$-$CH_3$, $N$-$CH_3$, $C_2H_5$ | 137 |
| 109 | — | O | $CHF_2$ | (5-) $CH_3$ | triazolinone with $N$-$CH_3$, $N$-$CH_3$, $CH_2CH_2CH_3$ | 117 |
| 110 | — | O | $CHF_2$ | (5-) $CH_3$ | triazolinone with $N$-$CH_3$, $N$-cyclopropyl, $SC_2H_5$ | 155 |
| 111 | — | O | $CHF_2$ | (4-) $CH_3$ | triazolinone with $N$-$CH_3$, $N$-$CH_3$, $OC_2H_5$ | 152 |
| 112 | — | O | $CHF_2$ | (4-) $CH_3$ | triazolinone with $N$-$CH_3$, $N$-$CH_3$, $SCH_3$ | 176 |
| 113 | — | O | $CHF_2$ | (4-) $CH_3$ | triazolinone with $N$-$CH_3$, $N$-$CH_3$, $C_2H_5$ | 108 |

TABLE 1-continued

Examples of the compounds of the formula (I)

| Ex. No. | A | Q | R¹ | (position-) R² | R³ | Melting point (° C.) |
|---|---|---|---|---|---|---|
| 114 | — | O | CHF$_2$ | (6-) CH$_3$ | *N-methyl-4-methyl-5-methoxy-1,2,4-triazol-3(2H)-one* | 163 |
| 115 | — | O | CHF$_2$ | (6-) CH$_3$ | *N-methyl-4-methyl-5-(n-propoxy)-1,2,4-triazol-3(2H)-one* | 136 |
| 116 | — | O | CHF$_2$ | (6-) CH$_3$ | *N-methyl-4-methyl-5-ethoxy-1,2,4-triazol-3(2H)-one* | 118 |
| 117 | — | O | CHF$_2$ | (6-) CH$_3$ | *N-methyl-4-cyclopropyl-5-(n-propoxy)-1,2,4-triazol-3(2H)-one* | 104 |
| 118 | — | O | CHF$_2$ | (5-) CH$_3$ | *N-methyl-4-cyclopropyl-5-(n-propoxy)-1,2,4-triazol-3(2H)-one* | 98 |
| 119 | — | O | CHF$_2$ | (6-) CH$_3$ | *N-methyl-4-cyclopropyl-5-(ethylthio)-1,2,4-triazol-3(2H)-one* | 128 |
| 120 | — | O | CHF$_2$ | (6-) CH$_3$ | *N-methyl-4-methyl-5-(methylthio)-1,2,4-triazol-3(2H)-one* | 165 |
| 121 | — | O | CHF$_2$ | (6-) CH$_3$ | *N-methyl-4-cyclopropyl-5-(ethylthio)-1,2,4-triazol-3(2H)-one* | 155 |

TABLE 1-continued
Examples of the compounds of the formula (I)
| Ex. No. | A | Q | R¹ | (position-) R² | R³ | Melting point (° C.) |
|---|---|---|---|---|---|---|
| 122 | — | O | CHF₂ | (6-) CH₃ | 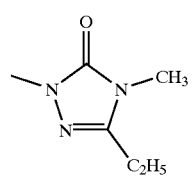 | 105 |
| 123 | — | O | CHF₂ | (6-) CH₃ | 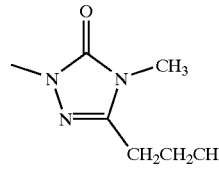 | 81 |
| 124 | — | O | CHF₂ | (6-) CH₃ | 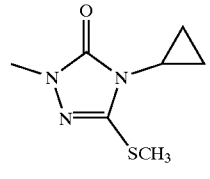 | 174 |
| 125 | — | O | CHF₂ | (5-) CH₃ | 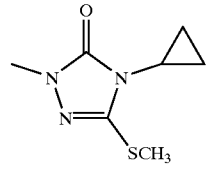 | 150 |
| 126 | — | O | CHF₂ | (6-) CH₃ | 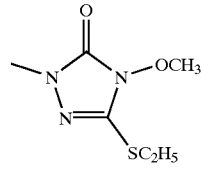 | 124 |
| 127 | — | O | CHF₂ | (6-) CH₃ | 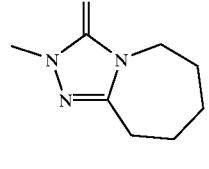 | 200 |
| 128 | — | S | n-C₃H₇ | (6-) CH₃ | 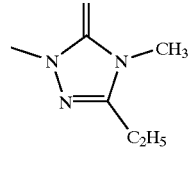 | 160 |
| 129 | — | S | n-C₃H₇ | (6-) CH₃ | 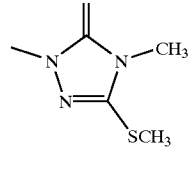 | 148 |

TABLE 1-continued

Examples of the compounds of the formula (I)

| Ex. No. | A | Q | R¹ | (position-) R² | R³ | Melting point (° C.) |
|---|---|---|---|---|---|---|
| 130 | — | S | $C_2H_5$ | (6-) $CH_3$ | 1,4-dimethyl-5-ethoxy-1,2,4-triazol-3(2H)-one-2-yl | 141 |
| 131 | — | S | $C_2H_5$ | (6-) $CH_3$ | 1,4,5-trimethyl-1,2,4-triazol-3(2H)-one-2-yl | 125 |
| 132 | — | S | $C_2H_5$ | (6-) $CH_3$ | 1,4-dimethyl-5-methoxy-1,2,4-triazol-3(2H)-one-2-yl | 158 |
| 133 | — | S | $i\text{-}C_3H_7$ | (6-) $CH_3$ | 1,4-dimethyl-5-methoxy-1,2,4-triazol-3(2H)-one-2-yl | 155 |
| 134 | — | S | $n\text{-}C_3H_7$ | (6-) $CH_3$ | 1,4-dimethyl-5-methoxy-1,2,4-triazol-3(2H)-one-2-yl | 153 |
| 135 | — | S | $n\text{-}C_3H_7$ | (6-) $CH_3$ | 1,4-dimethyl-5-ethoxy-1,2,4-triazol-3(2H)-one-2-yl | 131 |
| 136 | — | S | $n\text{-}C_3H_7$ | (6-) $CH_3$ | 1,4,5-trimethyl-1,2,4-triazol-3(2H)-one-2-yl | 120 |
| 137 | — | O | $C_2H_5$ | (6-) Cl | 1,4-dimethyl-5-methylthio-1,2,4-triazol-3(2H)-one-2-yl | 149 |

TABLE 1-continued
Examples of the compounds of the formula (I)
| Ex. No. | A | Q | R¹ | (position-) R² | R³ | Melting point (° C.) |
|---|---|---|---|---|---|---|
| 138 | — | O | $C_2H_5$ | (6-) Cl | 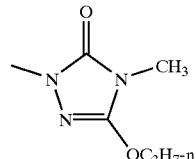 | 99 |
| 139 | — | O | $CH_3$ | (6-) Cl | 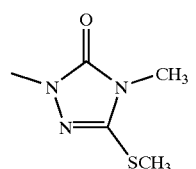 | 176 |
| 140 | — | O | $CH_3$ | (6-) Cl | 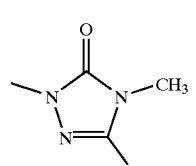 | 192 |
| 141 | — | O | $C_2H_5$ | (6-) Cl | 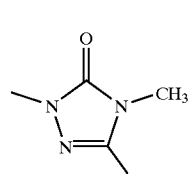 | 144 |
| 142 | — | O | $CH_3$ | (6-) Cl | 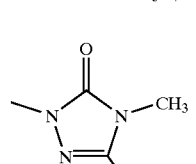 | 114 |
| 143 | — | O | $C_2H_5$ | (6-) Cl | 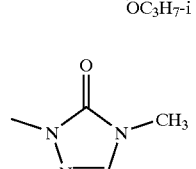 | 144 |
| 144 | — | O | $CH_3$ | (6-) Cl | 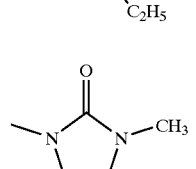 | 157 |
| 145 | — | O | $C_2H_5$ | (6-) Cl | 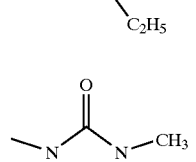 | 142 |

TABLE 1-continued

Examples of the compounds of the formula (I)

| Ex. No. | A | Q | R¹ | (position-) R² | R³ | Melting point (° C.) |
|---|---|---|---|---|---|---|
| 146 | — | O | CH₃ | (6-) Cl | 1,4-dimethyl-5-ethoxy-1,2,4-triazol-3(2H)-one | 191 |
| 147 | — | O | C₂H₅ | (6-) Cl | 1,4-dimethyl-5-(2,2,2-trifluoroethoxy)-1,2,4-triazol-3(2H)-one | 116 |
| 148 | — | O | CH₃ | (6-) Cl | 1,4-dimethyl-5-(2,2,2-trifluoroethoxy)-1,2,4-triazol-3(2H)-one | 205 |
| 149 | — | O | CH₃ | (6-) Cl | 1,4-dimethyl-5-isopropyl-1,2,4-triazol-3(2H)-one | 147 |
| 150 | — | O | C₂H₅ | (6-) Cl | 1-methyl-4-cyclopropyl-5-bromo-1,2,4-triazol-3(2H)-one | 117 |
| 151 | — | O | CH₃ | (6-) Cl | 1-methyl-4-cyclopropyl-5-bromo-1,2,4-triazol-3(2H)-one | 149 |
| 152 | — | O | CH₃ | (6-) Cl | 1,4-dimethyl-5-methoxymethyl-1,2,4-triazol-3(2H)-one | 176 |
| 153 | — | O | CH₃ | (6-) Cl | 1,4-dimethyl-5-ethylthio-1,2,4-triazol-3(2H)-one | 150 |

TABLE 1-continued

Examples of the compounds of the formula (I)

| Ex. No. | A | Q | R¹ | (position-) R² | R³ | Melting point (° C.) |
|---|---|---|---|---|---|---|
| 154 | — | O | CH₃ | (6-) Cl | [1,2,4-triazol-3(2H)-one, 2,4-dimethyl-5-propyl] | 146 |
| 155 | — | O | CH₃ | (6-) Cl | [1,2,4-triazol-3(2H)-one, 2,4-dimethyl-5-methyl] | 191 |
| 156 | — | O | CH₃ | (6-) Cl | [1,2,4-triazol-3(2H)-one, 2-methyl-4-cyclopropyl-5-CH₂OCH₃] | 127 |
| 157 | — | O | CH₃ | (6-) Cl | [1,2,4-triazol-3(2H)-one, 2-methyl-4-C₂H₅-5-OCH₃] | 174 |
| 158 | — | O | n-C₃H₇ | (6-) Cl | [1,2,4-triazol-3(2H)-one, 2,4-dimethyl-5-C₂H₅] | 117 |
| 159 | — | O | n-C₃H₇ | (6-) Cl | [1,2,4-triazol-3(2H)-one, 2,4-dimethyl-5-OC₂H₅] | 134 |
| 160 | — | O | n-C₃H₇ | (6-) Cl | [1,2,4-triazol-3(2H)-one, 2,4-dimethyl-5-SCH₃] | 115 |
| 161 | — | O | n-C₃H₇ | (6-) Cl | [1,2,4-triazol-3(2H)-one, 2-methyl-4-cyclopropyl-5-OC₂H₅] | 137 |

TABLE 1-continued

Examples of the compounds of the formula (I)

| Ex. No. | A | Q | R¹ | (position-) R² | R³ | Melting point (° C.) |
|---|---|---|---|---|---|---|
| 162 | — | O | n-C₃H₇ | (6-) Cl | (1,2,4-triazol-3(2H)-one, 2-methyl-4-methyl-5-OCH₂CF₃) | 125 |
| 163 | — | O | n-C₃H₇ | (6-) Cl | (1,2,4-triazol-3(2H)-one, 2-methyl-4-methyl-5-S-CH₂C≡CH) | 119 |
| 164 | — | O | H | (6-) Cl | (1,2,4-triazol-3(2H)-one, 2-methyl-4-methyl-5-OC₂H₅) | 147 |
| 165 | — | O | n-C₃H₇ | (6-) Cl | (1,2,4-triazol-3(2H)-one, 2-methyl-4-cyclopropyl-5-OC₃H₇-i) | 148 |
| 166 | — | O | i-C₃H₇ | (6-) Cl | (1,2,4-triazol-3(2H)-one, 2-methyl-4-cyclopropyl-5-OC₃H₇-i) | 143 |
| 167 | — | O | i-C₃H₇ | (6-) Cl | (1,2,4-triazol-3(2H)-one, 2-methyl-4-methyl-5-S-CH₂C≡CH) | 122 |
| 168 | — | O | CH₃ | (6-) Cl | (1,2,4-triazol-3(2H)-one, 2-methyl-4-methyl-5-S-CH₂C≡CH) | 165 |

TABLE 1-continued
Examples of the compounds of the formula (I)
| Ex. No. | A | Q | R¹ | (position-) R² | R³ | Melting point (° C.) |
|---|---|---|---|---|---|---|
| 169 | — | O | n-$C_3H_7$ | (5-) Cl | 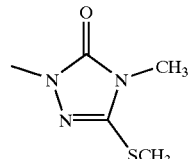 | 154 |
| 170 | — | O | n-$C_3H_7$ | (5-) Cl | 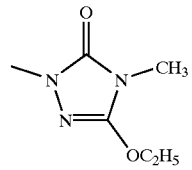 | 136 |
| 171 | — | O | n-$C_3H_7$ | (5-) Cl | 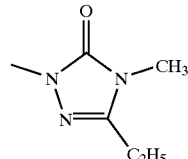 | 128 |
| 172 | — | O | $CH_3$ | (6-) Cl | 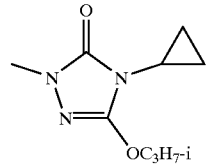 | 143 |
| 173 | — | O | i-$C_3H_7$ | (6-) Cl | 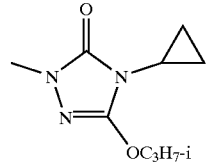 | 136 |
| 174 | — | O | i-$C_3H_7$ | (6-) Cl | 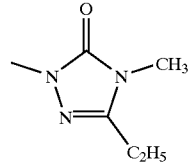 | 121 |
| 175 | — | O | i-$C_3H_7$ | (6-) Cl | 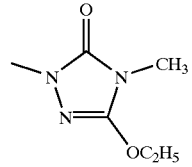 | 158 |
| 176 | — | O | i-$C_3H_7$ | (6-) Cl | 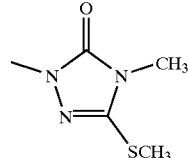 | 141 |

TABLE 1-continued

Examples of the compounds of the formula (I)

| Ex. No. | A | Q | R¹ | (position-) R² | R³ | Melting point (° C.) |
|---|---|---|---|---|---|---|
| 177 | — | O | i-C₃H₇ | (6-) Cl | [1-methyl-4-cyclopropyl-5-ethoxy-1,2,4-triazol-3(4H)-one] | 127 |
| 178 | — | O | i-C₃H₇ | (6-) Cl | [1-methyl-4-methyl-5-(2,2,2-trifluoroethoxy)-1,2,4-triazol-3(4H)-one] | 143 |
| 179 | — | O | i-C₃H₇ | (6-) Cl | [1-methyl-4-cyclopropyl-5-methoxymethyl-1,2,4-triazol-3(4H)-one] | 129 |
| 180 | — | O | i-C₃H₇ | (6-) Cl | [1-methyl-4-methyl-5-propyl-1,2,4-triazol-3(4H)-one] | 95 |
| 181 | — | O | n-C₃H₇ | (6-) CH₃ | [1-methyl-4-methyl-5-propyl-1,2,4-triazol-3(4H)-one] | 74 |
| 182 | — | O | n-C₃H₇ | (6-) CH₃ | [1-methyl-4-allyl-5-(2,2,2-trifluoroethoxy)-1,2,4-triazol-3(4H)-one] | 114 |
| 183 | — | O | n-C₃H₇ | (6-) CH₃ | [1-methyl-4-cyclopropyl-5-methyl-1,2,4-triazol-3(4H)-one] | 140 |
| 184 | — | O | n-C₃H₇ | (6-) CH₃ | [1-methyl-4-cyclopropyl-1,2,4-triazol-3(4H)-one] | 159 |

TABLE 1-continued

Examples of the compounds of the formula (I)

| Ex. No. | A | Q | R¹ | (position-) R² | R³ | Melting point (° C.) |
|---|---|---|---|---|---|---|
| 185 | — | O | n-C₃H₇ | (6-) CH₃ | (1,4-dimethyl-5-oxo-4,5-dihydro-1H-1,2,4-triazol-3-yl) with CH₂OC₂H₅ | 107 |
| 186 | — | O | n-C₃H₇ | (6-) CH₃ | (1,4-dimethyl-5-oxo-4,5-dihydro-1H-1,2,4-triazol-3-yl) with OC₆H₁₁ | 132 |
| 187 | — | O | n-C₃H₇ | (6-) CH₃ | (1,4-dimethyl-5-oxo-4,5-dihydro-1H-1,2,4-triazol-3-yl) with N(CH₃)₂ | 132 |
| 188 | — | O | n-C₃H₇ | (6-) CH₃ | (1-methyl-4-cyclopropyl-5-oxo-4,5-dihydro-1H-1,2,4-triazol-3-yl) with cyclopropyl | 110 |
| 189 | — | O | CH₃ | (6-) CH₃ | (1,4-dimethyl-5-oxo-4,5-dihydro-1H-1,2,4-triazol-3-yl) with S-CH₂-C≡CH | 159 |
| 190 | — | O | n-C₃H₇ | (6-) CH₃ | (1,4-dimethyl-5-oxo-4,5-dihydro-1H-1,2,4-triazol-3-yl) with OCH₂CH₂CH(CH₃)₂ | 138 |
| 191 | — | O | n-C₃H₇ | (6-) CH₃ | (1,4-dimethyl-5-oxo-4,5-dihydro-1H-1,2,4-triazol-3-yl) with H | 147 |

TABLE 1-continued

Examples of the compounds of the formula (I)

| Ex. No. | A | Q | R¹ | (position-) R² | R³ | Melting point (° C.) |
|---|---|---|---|---|---|---|
| 192 | — | O | n-C$_3$H$_7$ | (6-) CH$_3$ | triazolinone with N-CH$_3$, N-cyclopropyl, OC$_3$H$_7$-n | 114 |
| 193 | — | O | n-C$_3$H$_7$ | (6-) CH$_3$ | triazolinone with N-CH$_3$, N-CH$_3$, CH$_2$CH$_2$OC$_3$H$_7$-i | 125 |
| 194 | — | O | n-C$_3$H$_7$ | (6-) CH$_3$ | triazolinone with N-CH$_3$, N-CH$_3$, CH$_2$CH$_2$OCH$_3$ | 126 |
| 195 | — | O | n-C$_3$H$_7$ | (6-) CH$_3$ | triazolinone with N-CH$_3$, N-CH$_3$, OCH$_2$C(CH$_3$)$_3$ | 151 |
| 196 | — | O | n-C$_3$H$_7$ | (6-) CH$_3$ | triazolinone with N-CH$_3$, N-CH$_3$, cyclopropyl | 121 |
| 197 | — | O | n-C$_3$H$_7$ | (6-) CH$_3$ | triazolinone with N-CH$_3$, N-CH$_3$, OCH$_2$CCl$_3$ | 147 |
| 198 | NH | O | C$_2$H$_5$ | (6-) CH$_3$ | triazolinone with N-CH$_3$, N-CH$_3$, C$_2$H$_5$ | 135 |
| 199 | — | O | i-C$_3$H$_7$ | (6-) CH$_3$ | triazolinone with N-CH$_3$, N-CH$_3$, CH$_3$ | 263 (Sodium salt) |

TABLE 1-continued

Examples of the compounds of the formula (I)

| Ex. No. | A | Q | R¹ | (position-) R² | R³ | Melting point (° C.) |
|---|---|---|---|---|---|---|
| 200 | — | O | $C_2H_5$ | (6-) $CH_3$ | triazolinone with $CH_3$, $OC_3H_7$-i | 119 |
| 201 | — | O | $C_2H_5$ | (6-) $CH_3$ | triazolinone with $CH_3$, $OCH_2C_6H_5$ | 146 |
| 202 | — | O | $C_2H_5$ | (6-) $CH_3$ | triazolinone with cyclopropyl, $CH_3$ | 128 |
| 203 | — | O | $C_2H_5$ | (6-) $CH_3$ | triazolinone with cyclopropyl, H | 186 |
| 204 | — | O | $C_2H_5$ | (6-) $CH_3$ | triazolinone with $CH_3$, $CH_2OC_2H_5$ | 239 |
| 205 | — | O | $C_2H_5$ | (6-) $CH_3$ | triazolinone with $CH_3$, $OC_6H_{11}$ | 152 |
| 206 | — | O | $C_2H_5$ | (6-) $CH_3$ | triazolinone with $CH_3$, $N(CH_3)_2$ | 155 |
| 207 | — | O | $C_2H_5$ | (6-) $CH_3$ | triazolinone with $CH_3$, $OC_2H_5$ | 145 (Na salt) |

TABLE 1-continued
Examples of the compounds of the formula (I)
| Ex. No. | A | Q | R¹ | (position-) R² | R³ | Melting point (° C.) |
|---|---|---|---|---|---|---|
| 208 | — | O | i-C₃H₇ | (6-) CH₃ | 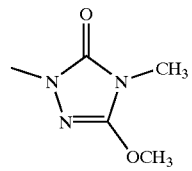 | 209 (Na salt) |
| 209 | — | O | C₂H₅ | (6-) CH₃ | 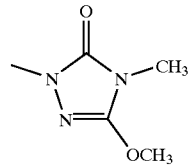 | 147 (Na salt) |
| 210 | — | O | C₂H₅ | (6-) CH₃ | 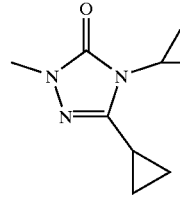 | 140 |
| 211 | — | O | C₂H₅ | (6-) CH₃ | 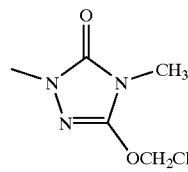 | 118 |
| 212 | — | O | C₂H₅ | (6-) CH₃ | 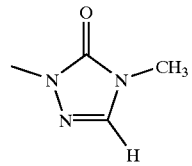 | 156 |
| 213 | — | O | C₂H₅ | (6-) CH₃ | 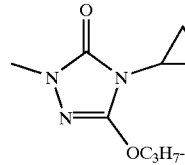 | 110 |
| 214 | — | O | C₂H₅ | (6-) CH₃ | 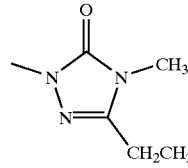 | 133 |
| 215 | — | O | i-C₃H₇ | (6-) CH₃ | 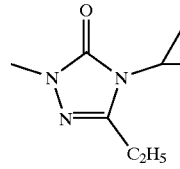 | 138 |

TABLE 1-continued

Examples of the compounds of the formula (I)

| Ex. No. | A | Q | R¹ | (position-) R² | R³ | Melting point (° C.) |
|---|---|---|---|---|---|---|
| 216 | — | O | i-C₃H₇ | (6-) CH₃ | (1-methyl-4-cyclopropyl-5-oxo-4,5-dihydro-1H-1,2,4-triazol-3-yl) with CH=CH-CH₃ | 154 |
| 217 | — | O | i-C₃H₇ | (6-) CH₃ | triazolone with N-CH₃ and OCH₂CH₂OCH₃ | 149 |
| 218 | — | O | i-C₃H₇ | (6-) CH₃ | triazolone with N-cyclopropyl and CH₂OC₂H₅ | 112 |
| 219 | — | O | i-C₃H₇ | (6-) CH₃ | triazolone with N-CH₃ and OCH₂CF₂CHF₂ | 162 |
| 220 | — | O | i-C₃H₇ | (6-) CH₃ | triazolone with N-allyl and OCH₂CF₃ | 99 |
| 221 | — | O | i-C₃H₇ | (6-) CH₃ | triazolone with N-C₂H₅ and OC₃H₇-i | 146 |
| 222 | — | O | C₂H₅ | (6-) CH₃ | triazolone with N-CH₃ and OC₂H₅ | 134 |
| 223 | — | O | CH₃ | (6-) CH₃ | triazolone with N-CH₃ and CH₃ | 199 |

TABLE 1-continued

Examples of the compounds of the formula (I)

| Ex. No. | A | Q | R¹ | (position-) R² | R³ | Melting point (° C.) |
|---|---|---|---|---|---|---|
| 224 | — | O | CH₃ | (6-) CH₃ | [1,2,4-triazol-3(2H)-one, 2,4-dimethyl-5-OCH₃] | 176 |
| 225 | — | O | CH₃ | (6-) CH₃ | [1,2,4-triazol-3(2H)-one, 2,4-dimethyl-5-CH₂OCH₃] | 145 |
| 226 | — | O | i-C₃H₇ | (6-) CH₃ | [1,2,4-triazol-3(2H)-one, 2,4-dimethyl-5-OC₄H₉-s] | 133 |
| 227 | NH | O | n-C₃H₇ | (5-) CH₃ | [1,2,4-triazol-3(2H)-one, 2,4-dimethyl-5-OC₂H₅] | 127 |
| 228 | — | O | i-C₃H₇ | (6-) CH₃ | [1,2,4-triazol-3(2H)-one, 2,4-dimethyl-5-OCH₂C₆H₅] | 144 |
| 229 | — | O | i-C₃H₇ | (6-) CH₃ | [1,2,4-triazol-3(2H)-one, 2-methyl-4-cyclopropyl-5-CH₃] | 141 |
| 230 | — | O | i-C₃H₇ | (6-) CH₃ | [1,2,4-triazol-3(2H)-one, 2-methyl-4-cyclopropyl-5-H] | 152 |
| 231 | — | O | i-C₃H₇ | (6-) CH₃ | [1,2,4-triazol-3(2H)-one, 2,4-dimethyl-5-CH₂OC₂H₅] | 132 |

TABLE 1-continued
Examples of the compounds of the formula (I)
| Ex. No. | A | Q | R¹ | (position-) R² | R³ | Melting point (° C.) |
|---|---|---|---|---|---|---|
| 232 | — | O | i-$C_3H_7$ | (6-) $CH_3$ | 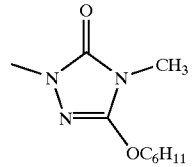 | 147 |
| 233 | — | O | i-$C_3H_7$ | (6-) $CH_3$ | 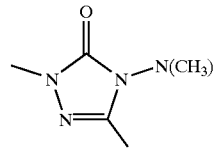 | 163 |
| 234 | — | O | i-$C_3H_7$ | (6-) $CH_3$ | 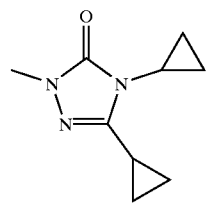 | 102 |
| 235 | — | O | $C_2H_5$ | (6-) $CH_3$ | 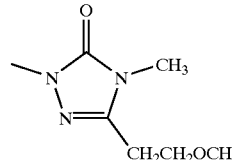 | 121 |
| 236 | — | O | $C_2H_5$ | (6-) $CH_3$ | 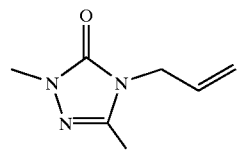 | 113 |
| 237 | — | O | $C_2H_5$ | (6-) $CH_3$ | 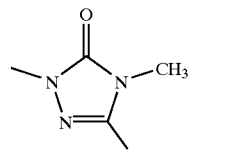 | 145 |
| 238 | — | O | $C_2H_5$ | (6-) $CH_3$ | 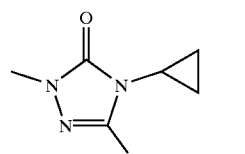 | 137 |
| 239 | — | O | $C_2H_5$ | (6-) $CH_3$ | 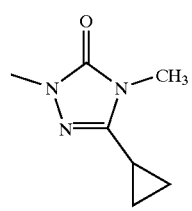 | 172 |

TABLE 1-continued
Examples of the compounds of the formula (I)
| Ex. No. | A | Q | R¹ | (position-) R² | R³ | Melting point (° C.) |
|---|---|---|---|---|---|---|
| 240 | — | O | $C_2H_5$ | (6-) $CH_3$ | 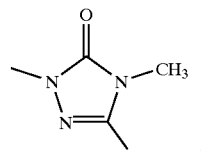 | 148 |
| 241 | — | O | $C_2H_5$ | (6-) $CH_3$ | 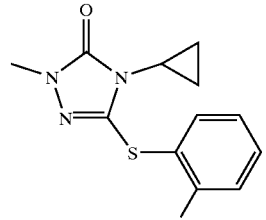 | 157 |
| 242 | — | O | $C_2H_5$ | (6-) $CH_3$ | 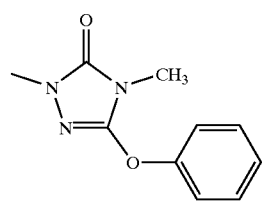 | 186 |
| 243 | NH | O | $CH_3$ | (6-) $OCH_3$ | 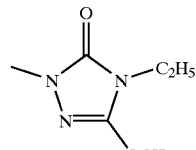 | 170 |
| 244 | — | O | $CHF_2$ | (5-) $CH_3$ | 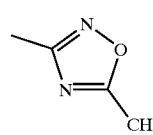 | |
| 245 | — | S | $i\text{-}C_3H_7$ | (6-) $CH_3$ | 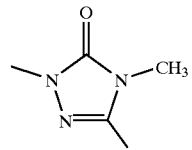 | 160 |
| 246 | — | O | $CH_3$ | (6-) $CF_3$ | 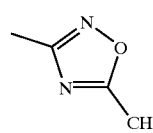 | 205 |
| 247 | — | S | $CH_3$ | (6-) $CF_3$ | 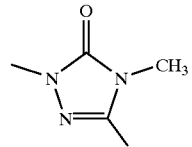 | 92 |

TABLE 1-continued

Examples of the compounds of the formula (I)

| Ex. No. | A | Q | $R^1$ | (position-) $R^2$ | $R^3$ | Melting point (° C.) |
|---|---|---|---|---|---|---|
| 248 | — | S | $CH_3$ | (6-) $CF_3$ | 1,2,4-triazol-3(2H)-one, 2,4-dimethyl-5-methoxy | 154 |
| 249 | — | S | $CH_3$ | (6-) $CF_3$ | 1,2,4-triazol-3(2H)-one, 2,4-dimethyl-5-ethoxy | 157 |
| 250 | — | O | $C_2H_5$ | (6-) $CF_3$ | 3,5-dimethyl-1,2,4-oxadiazole | 176 |
| 251 | — | O | n-$C_3H_7$-n | (6-) $CF_3$ | 3,5-dimethyl-1,2,4-oxadiazole | 166 |
| 252 | — | O | i-$C_3H_7$ | (6-) $CF_3$ | 3,5-dimethyl-1,2,4-oxadiazole | 190 |
| 253 | — | O | $CH_3$ | (6-) $CF_3$ | 1,2,4-triazol-3(2H)-one, 2,4-dimethyl-5-(methylthio) | 203 |
| 254 | — | O | $CH_3$ | (6-) $CF_3$ | 1,2,4-triazol-3(2H)-one, 2,4-dimethyl-5-(ethylthio) | 156 |
| 255 | — | O | $CH_3$ | (6-) $CF_3$ | 1,2,4-triazol-3(2H)-one, 2,4-dimethyl-5-methoxy | 170 |
| 256 | — | O | $CH_3$ | (6-) $CF_3$ | 1,2,4-triazol-3(2H)-one, 2,4-dimethyl-5-ethoxy | 198 |

TABLE 1-continued

Examples of the compounds of the formula (I)

| Ex. No. | A | Q | R¹ | (position-) R² | R³ | Melting point (° C.) |
|---|---|---|---|---|---|---|
| 257 | — | O | CH₃ | (6-) CF₃ | triazolinone with N-CH₃, N-CH₃, OC₃H₇-i | 213 |
| 258 | — | O | CH₃ | (6-) CF₃ | triazolinone with N-CH₃, N-CH₃, OC₃H₇-i | 152 |
| 259 | — | O | CH₃ | (6-) CF₃ | triazolinone with N-CH₃, N-C₂H₅, OCH₃ | 187 |
| 260 | — | O | CH₃ | (6-) CF₃ | triazolinone with N-CH₃, N-CH₃, CH₃ | 210 |
| 261 | — | O | CH₃ | (6-) CF₃ | triazolinone with N-CH₃, N-CH₃, C₂H₅ | 172 |
| 262 | — | O | CH₃ | (6-) CF₃ | triazolinone with N-CH₃, N-CH₃, C₃H₇-n | 145 |
| 263 | — | O | CH₃ | (6-) CF₃ | triazolinone with N-CH₃, N-CH₃, C₃H₇-i | 136 |
| 264 | — | O | CH₃ | (6-) CF₃ | triazolinone with N-CH₃, N-OC₂H₅, C₂H₅ | 153 |

TABLE 1-continued

Examples of the compounds of the formula (I)

| Ex. No. | A | Q | R¹ | (position-) R² | R³ | Melting point (° C.) |
|---|---|---|---|---|---|---|
| 265 | — | O | CH₃ | (6-) CF₃ | [1,2,4-triazol-3(2H)-one with N-CH₃, N-OCH₃, C-C₃H₇-n] | 136 |
| 266 | — | O | CH₃ | (6-) CF₃ | [1,2,4-triazol-3(2H)-one with N-CH₃, N-cyclopropyl, C-OC₂H₅] | 210 |
| 267 | — | O | CH₃ | (6-) CF₃ | [1,2,4-triazol-3(2H)-one with N-CH₃, N-CH₃, C-CH₂OCH₃] | 147 |
| 268 | — | O | CH₃ | (6-) CF₃ | [1,2,4-triazol-3(2H)-one with N-CH₃, N-CH₃, C-Br] | 169 |
| 269 | — | O | CH₃ | (6-) CF₃ | [1,2,4-triazol-3(2H)-one with N-CH₃, N-CH₃, C-OCH₂CF₃] | 215 |
| 270 | — | O | CH₃ | (6-) CF₃ | [1,2,4-triazol-3(2H)-one with N-CH₃, N-cyclopropyl, C-CH₂OCH₃] | 138 |
| 271 | — | O | CH₃ | (6-) CF₃ | [1,2,4-triazol-3(2H)-one with N-CH₃, N-C₂H₅, C-OCH₃] | 182 |
| 272 | — | S | C₂H₅ | (6-) CF₃ | [1,2,4-triazol-3(2H)-one with N-CH₃, N-CH₃, C-CH₃] | 112 |

TABLE 1-continued

Examples of the compounds of the formula (I)

| Ex. No. | A | Q | R¹ | (position-) R² | R³ | Melting point (° C.) |
|---|---|---|---|---|---|---|
| 273 | — | S | $C_2H_5$ | (6-) $CF_3$ | 1-methyl-4-methyl-5-methoxy-1,2,4-triazol-3(4H)-one | 167 |
| 274 | — | S | $C_2H_5$ | (6-) $CF_3$ | 1-methyl-4-methyl-5-ethoxy-1,2,4-triazol-3(4H)-one | 152 |
| 275 | — | S | n-$C_3H_7$ | (6-) $CF_3$ | 1-methyl-4-methyl-5-methyl-1,2,4-triazol-3(4H)-one | 119 |
| 276 | — | S | n-$C_3H_7$ | (6-) $CF_3$ | 1-methyl-4-methyl-5-methoxy-1,2,4-triazol-3(4H)-one | 157 |
| 277 | — | S | n-$C_3H_7$ | (6-) $CF_3$ | 1-methyl-4-methyl-5-ethoxy-1,2,4-triazol-3(4H)-one | 154 |
| 278 | — | S | i-$C_3H_7$ | (6-) $CF_3$ | 1-methyl-4-methyl-5-methyl-1,2,4-triazol-3(4H)-one | 137 |
| 279 | — | S | i-$C_3H_7$ | (6-) $CF_3$ | 1-methyl-4-methyl-5-methoxy-1,2,4-triazol-3(4H)-one | 167 |
| 280 | — | S | i-$C_3H_7$ | (6-) $CF_3$ | 1-methyl-4-methyl-5-ethoxy-1,2,4-triazol-3(4H)-one | 137 |

TABLE 1-continued

Examples of the compounds of the formula (I)

| Ex. No. | A | Q | R¹ | (position-) R² | R³ | Melting point (° C.) |
|---|---|---|---|---|---|---|
| 281 | — | O | $C_2H_5$ | (6-) $CF_3$ | 1,2,4-triazolin-5-one, N-CH₃, N-CH₃, C-OC₂H₅ | 154 |
| 282 | — | O | $C_2H_5$ | (6-) $CF_3$ | 1,2,4-triazolin-5-one, N-CH₃, N-CH₃, C-C₃H₇-n | 160 |
| 283 | — | O | $C_2H_5$ | (6-) $CF_3$ | 1,2,4-triazolin-5-one, N-CH₃, N-CH₃, C-OC₃H₇-i | 139 |
| 284 | — | O | $C_2H_5$ | (6-) $CF_3$ | 1,2,4-triazolin-5-one, N-CH₃, N-CH₃, C-OCH₃ | 134 |
| 285 | — | O | $C_2H_5$ | (6-) $CF_3$ | 1,2,4-triazolin-5-one, N-CH₃, N-OC₂H₅, C-C₂H₅ | 142 |
| 286 | — | O | $C_2H_5$ | (6-) $CF_3$ | 1,2,4-triazolin-5-one, N-CH₃, N-OCH₃, C-C₃H₇-n | 120 |
| 287 | — | O | n-$C_3H_7$ | (6-) $CF_3$ | 1,2,4-triazolin-5-one, N-CH₃, N-CH₃, C-OC₂H₅ | 130 |
| 288 | — | O | n-$C_3H_7$ | (6-) $CF_3$ | 1,2,4-triazolin-5-one, N-CH₃, N-CH₃, C-OC₃H₇-n | 127 |

TABLE 1-continued
Examples of the compounds of the formula (I)
| Ex. No. | A | Q | R¹ | (position-) R² | R³ | Melting point (° C.) |
|---|---|---|---|---|---|---|
| 289 | — | O | n-C₃H₇ | (6-) CF₃ | 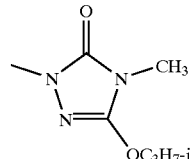 | 116 |
| 290 | — | O | n-C₃H₇ | (6-) CF₃ | 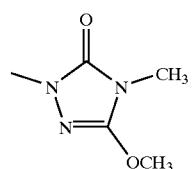 | 126 |
| 291 | — | O | n-C₃H₇ | (6-) CF₃ | 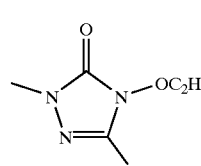 | 113 |
| 292 | — | O | i-C₃H₇ | (6-) CF₃ | 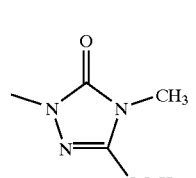 | 151 |
| 293 | — | O | i-C₃H₇ | (6-) CF₃ | 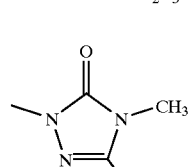 | 157 |
| 294 | — | O | i-C₃H₇ | (6-) CF₃ | 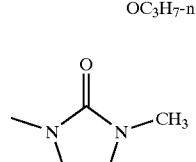 | 171 |
| 295 | — | O | i-C₃H₇ | (6-) CF₃ | 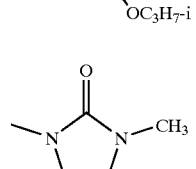 | 137 |
| 296 | — | O | i-C₃H₇ | (6-) CF₃ | 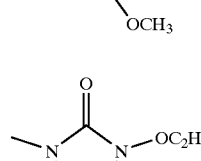 | 125 |

TABLE 1-continued

Examples of the compounds of the formula (I)

| Ex. No. | A | Q | R¹ | (position-) R² | R³ | Melting point (° C.) |
|---|---|---|---|---|---|---|
| 297 | — | O | n-C₃H₇ | (6-) CF₃ | 1-methyl-4-ethyl-5-ethoxy-1,2,4-triazol-3(4H)-one | 109 |
| 298 | — | O | n-C₃H₇ | (6-) CF₃ | 1-methyl-4-cyclopropyl-5-isopropoxy-1,2,4-triazol-3(4H)-one | 138 |
| 299 | — | O | i-C₃H₇ | (6-) CF₃ | 1-methyl-4-methoxy-5-n-propyl-1,2,4-triazol-3(4H)-one | 130 |
| 300 | — | O | C₂H₅ | (6-) CF₃ | 1-methyl-4-cyclopropyl-5-isopropoxy-1,2,4-triazol-3(4H)-one | 165 |
| 301 | — | O | i-C₃H₇ | (6-) CF₃ | 1-methyl-4-methyl-5-bromo-1,2,4-triazol-3(4H)-one | 148 |
| 302 | — | O | i-C₃H₇ | (6-) CF₃ | 1-methyl-4-methyl-5-(2,2,2-trifluoroethoxy)-1,2,4-triazol-3(4H)-one | 147 |
| 303 | — | O | i-C₃H₇ | (6-) CF₃ | 1-methyl-4-methyl-5-n-propyl-1,2,4-triazol-3(4H)-one | 172 |
| 304 | — | O | i-C₃H₇ | (6-) CF₃ | 1-methyl-4-methyl-5-methoxymethyl-1,2,4-triazol-3(4H)-one | 147 |

TABLE 1-continued

Examples of the compounds of the formula (I)

| Ex. No. | A | Q | R¹ | (position-) R² | R³ | Melting point (° C.) |
|---|---|---|---|---|---|---|
| 305 | — | O | i-$C_3H_7$ | (6-) $CF_3$ | 1-methyl-4-cyclopropyl-5-bromo-1,2,4-triazol-3(4H)-one | 136 |
| 306 | — | O | $C_2H_5$ | (6-) $CF_3$ | 1-methyl-4-methyl-5-methyl-1,2,4-triazol-3(4H)-one | 124 |
| 307 | — | O | $C_2H_5$ | (6-) $CF_3$ | 1-methyl-4-methyl-5-ethyl-1,2,4-triazol-3(4H)-one | 98 |
| 308 | — | O | $C_2H_5$ | (6-) $CF_3$ | 1-methyl-4-methyl-5-isopropyl-1,2,4-triazol-3(4H)-one | 125 |
| 309 | — | O | $C_2H_5$ | (6-) $CF_3$ | 1-methyl-4-methyl-5-methylthio-1,2,4-triazol-3(4H)-one | 179 |
| 310 | — | O | $C_2H_5$ | (6-) $CF_3$ | 1-methyl-4-methyl-5-ethylthio-1,2,4-triazol-3(4H)-one | 153 |
| 311 | — | O | $C_2H_5$ | (6-) $CF_3$ | 1-methyl-4-methyl-5-methoxy-1,2,4-triazol-3(4H)-one | 171 |
| 312 | — | O | n-$C_3H_7$ | (6-) $CF_3$ | 1-methyl-4-methyl-5-ethyl-1,2,4-triazol-3(4H)-one | 113 |

TABLE 1-continued
Examples of the compounds of the formula (I)
| Ex. No. | A | Q | R¹ | (position-) R² | R³ | Melting point (° C.) |
|---|---|---|---|---|---|---|
| 313 | — | O | n-$C_3H_7$ | (6-) $CF_3$ | 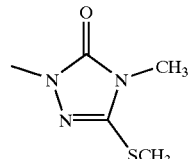 | 138 |
| 314 | — | O | n-$C_3H_7$ | (6-) $CF_3$ | 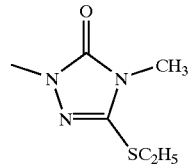 | 110 |
| 315 | — | O | n-$C_3H_7$ | (6-) $CF_3$ | 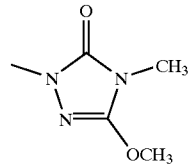 | 134 |
| 316 | — | O | i-$C_3H_7$ | (6-) $CF_3$ | 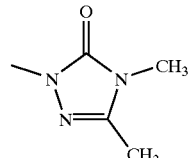 | 167 |
| 317 | — | O | i-$C_3H_7$ | (6-) $CF_3$ | 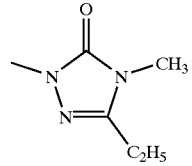 | 120 |
| 318 | — | O | i-$C_3H_7$ | (6-) $CF_3$ | 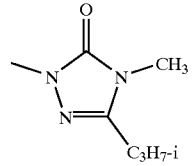 | 117 |
| 319 | — | O | i-$C_3H_7$ | (6-) $CF_3$ | 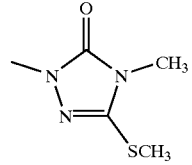 | 160 |
| 320 | — | O | i-$C_3H_7$ | (6-) $CF_3$ | 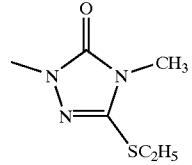 | 154 |

TABLE 1-continued

Examples of the compounds of the formula (I)

| Ex. No. | A | Q | R¹ | (position-) R² | R³ | Melting point (° C.) |
|---|---|---|---|---|---|---|
| 321 | — | O | i-C$_3$H$_7$ | (6-) CF$_3$ | triazolinone with N-CH$_3$, OCH$_3$ | 159 |
| 322 | — | O | n-C$_3$H$_7$ | (6-) CF$_3$ | triazolinone with N-cyclopropyl, OC$_2$H$_5$ | 141 |
| 323 | — | O | i-C$_3$H$_7$ | (6-) CF$_3$ | triazolinone with N-cyclopropyl, OC$_2$H$_5$ | 146 |
| 324 | — | O | i-C$_3$H$_7$ | (6-) CF$_3$ | triazolinone with N-C$_2$H$_5$, OC$_2$H$_5$ | 134 |
| 325 | — | O | i-C$_3$H$_7$ | (6-) CF$_3$ | triazolinone with N-cyclopropyl, OC$_3$H$_7$-i | 168 |
| 326 | — | O | CH$_3$ | (6-) C$_3$H$_7$-n | triazolinone with N-CH$_3$, OC$_2$H$_5$ | 158 |
| 327 | — | O | CH$_3$ | (6-) C$_3$H$_7$-n | triazolinone with N-CH$_3$, C$_2$H$_5$ | 172 |
| 328 | — | O | CH$_3$ | (6-) C$_3$H$_7$-n | triazolinone with N-CH$_3$, SCH$_3$ | 147 |

TABLE 1-continued

Examples of the compounds of the formula (I)

| Ex. No. | A | Q | R¹ | (position-) R² | R³ | Melting point (° C.) |
|---|---|---|---|---|---|---|
| 329 | — | O | C₂H₅ | (6-) CF₃ | 2-methyl-5-ethoxy-1,3-oxazole | 66 |
| 330 | — | O | C₂H₅ | (6-) CH₃ | 3-methyl-5-cyclopropyl-1,2,4-oxadiazole | 134 |
| 331 | — | O | C₂H₅ | (6-) CH₃ | 2-methyl-5-methyl-1,3-oxazole | 149 |
| 332 | — | O | n-C₃H₇ | (6-) CH₃ | 3-methyl-5-methyl-1,2,4-oxadiazole | 114 |
| 333 | — | O | H | (6-) Cl | 2-methyl-4-methyl-5-ethyl-1,2,4-triazol-3-one | 102 |
| 334 | — | O | H | (6-) Cl | 2-methyl-4-methyl-5-methylthio-1,2,4-triazol-3-one | 143 |
| 335 | — | O | —CH₂CH=CH₂ | (6-) Cl | 2-methyl-4-methyl-5-ethoxy-1,2,4-triazol-3-one | 130 |
| 336 | — | O | —CH₂C₆H₅ | (6-) Cl | 2-methyl-4-methyl-5-ethoxy-1,2,4-triazol-3-one | 143 |
| 337 | — | O | —CH₂C₆H₅ | (6-) Cl | 2-methyl-4-methyl-5-ethyl-1,2,4-triazol-3-one | 99 |

TABLE 1-continued
Examples of the compounds of the formula (I)
| Ex. No. | A | Q | R¹ | (position-) R² | R³ | Melting point (° C.) |
|---|---|---|---|---|---|---|
| 338 | — | O | —CH₂C≡CH | (6-) Cl | 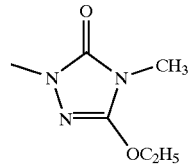 | 161 |
| 339 | — | O | n-C₃H₇ | (6-) CH₃ | 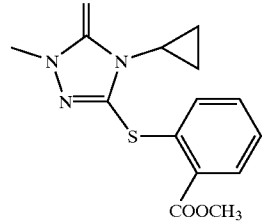 | 133 |
| 340 | — | O | H | (6-) CH₃ | 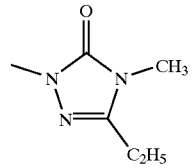 | 100 |
| 341 | — | O | H | (6-) CH₃ | 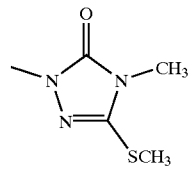 | 147 |
| 342 | — | O | —CH₂C₆H₅ | (6-) CH₃ | 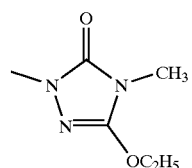 | 157 |
| 343 | — | O | —CH₂<br>\|<br>COOC₂H₅ | (6-) CH₃ |  | 150 |
| 344 | — | O | —CH₂C≡CH | (6-) CH₃ | 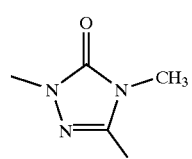 | 172 |
| 345 | — | O | i-C₃H₇ | (6-) CH₃ | 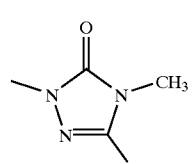 | 263 (Na salt) |

TABLE 1-continued

Examples of the compounds of the formula (I)

| Ex. No. | A | Q | R¹ | (position-) R² | R³ | Melting point (° C.) |
|---|---|---|---|---|---|---|
| 346 | — | O | $C_2H_5$ | (6-) $CH_3$ | 4-amino-2-methyl-5-(methoxymethyl)-2,4-dihydro-3H-1,2,4-triazol-3-one | 136 |
| 347 | — | O | i-$C_3H_7$ | (6-) $CH_3$ | 2,4-dimethyl-5-(isopentyloxy)-2,4-dihydro-3H-1,2,4-triazol-3-one ($OCH_2CH_2CH(CH_3)_2$) | 113 |
| 348 | — | O | i-$C_3H_7$ | (6-) $CH_3$ | 2,4-dimethyl-2,4-dihydro-3H-1,2,4-triazol-3-one (H) | 175 |
| 349 | — | O | i-$C_3H_7$ | (6-) $CH_3$ | 4-cyclopropyl-2-methyl-5-(n-propoxy)-2,4-dihydro-3H-1,2,4-triazol-3-one ($OC_3H_7$-n) | 135 |
| 350 | — | O | i-$C_3H_7$ | (6-) $CH_3$ | 2,4-dimethyl-5-(2-isopropoxyethyl)-2,4-dihydro-3H-1,2,4-triazol-3-one ($CH_2CH_2OCH(CH_3)_2$) | 78 |
| 351 | — | O | i-$C_3H_7$ | (6-) $CH_3$ | 4-cyclopropyl-2-methyl-5-[(2-methoxycarbonylphenyl)thio]-2,4-dihydro-3H-1,2,4-triazol-3-one (S-C₆H₄-COOCH₃) | 125 |
| 352 | — | O | i-$C_3H_7$ | (6-) $CH_3$ | 2,4-dimethyl-5-(2-methoxyethyl)-2,4-dihydro-3H-1,2,4-triazol-3-one ($CH_2CH_2OCH_3$) | 140 |

TABLE 1-continued

Examples of the compounds of the formula (I)

| Ex. No. | A | Q | R¹ | (position-) R² | R³ | Melting point (° C.) |
|---|---|---|---|---|---|---|
| 353 | — | O | $CH_3$ | (6-) $CH_3$ | triazolinone with $N-CH_3$, $N-CH_3$, $OC_3H_7-n$ | 161 |
| 354 | — | O | $CH_3$ | (6-) $CH_3$ | triazolinone with $N-CH_3$, $N-CH_3$, $C_3H_7-i$ | 142 |
| 355 | — | O | $CH_3$ | (6-) $CH_3$ | triazolinone with $N-CH_3$, $N-CH_3$, $OC_3H_7-n$ | 124 |
| 356 | — | O | $CH_3$ | (6-) $CH_3$ | triazolinone with $N-CH_3$, $N-CH_3$, $SC_2H_5$ | 153 |
| 357 | — | O | $CH_3$ | (6-) $CH_3$ | triazolinone with $N-CH_3$, $N-C_2H_5$, $OCH_3$ | 170 |
| 358 | — | O | $CH_3$ | (6-) $CH_3$ | triazolinone with $N-CH_3$, $N-C_2H_5$, $OC_2H_5$ | 116 |
| 359 | — | O | $CH_3$ | (6-) $CH_3$ | triazolinone with $N-CH_3$, $N-OCH_3$, $C_3H_7-n$ | 120 |
| 360 | — | O | $CH_3$ | (5-) Cl | triazolinone with $N-CH_3$, $N-CH_3$, $OCH_3$ | 172 |

TABLE 1-continued

Examples of the compounds of the formula (I)

| Ex. No. | A | Q | R¹ | (position-) R² | R³ | Melting point (° C.) |
|---|---|---|---|---|---|---|
| 361 | — | O | $CH_3$ | (5-) Cl | triazolinone with $OC_3H_7$-i | 175 |
| 362 | — | O | $CH_3$ | (5-) Cl | triazolinone with $SCH_3$ | 192 |
| 363 | — | O | $CH_3$ | (5-) Cl | triazolinone with $SC_2H_5$ | 195 |
| 364 | — | O | $CH_3$ | (5-) Cl | triazolinone with $SCH_2C_6H_5$ | 174 |
| 365 | — | O | $CH_3$ | (5-) Cl | triazolinone with $CH_2OCH_3$ | 160 |
| 366 | — | O | $CH_3$ | (5-) Cl | triazolinone with $OCH_3$ | 214 |
| 367 | — | O | $CH_3$ | (5-) Cl | triazolinone with $OC_3H_7$-n | 185 |
| 368 | — | O | $CH_3$ | (5-) Cl | triazolinone with $CH=CH-CH_3$ | 191 |

TABLE 1-continued

Examples of the compounds of the formula (I)

| Ex. No. | A | Q | R¹ | (position-) R² | R³ | Melting point (° C.) |
|---|---|---|---|---|---|---|
| 369 | NH | O | CH₃ | (6-) CH₃ | 1,2,4-triazol-3(2H)-one, 2-methyl-4-methyl-5-C₂H₅ | 161 |
| 370 | NH | O | i-C₃H₇ | (6-) CH₃ | 1,2,4-triazol-3(2H)-one, 2-methyl-4-methyl-5-C₂H₅ | 132 |
| 371 | NH | O | CH₃ | (6-) OCH₃ | 1,2,4-triazol-3(2H)-one, 2-methyl-4-methyl-5-C₂H₅ | 151 |
| 372 | NH | O | CH₃ | (6-) CH₃ | 1,2,4-triazol-3(2H)-one, 2-methyl-4-methyl-5-OC₂H₅ | 161 |
| 373 | NH | O | i-C₃H₇ | (6-) CH₃ | 1,2,4-triazol-3(2H)-one, 2-methyl-4-methyl-5-OC₂H₅ | 128 |
| 374 | NH | O | CH₃ | (6-) CH₃ | 1,2,4-triazol-3(2H)-one, 2-methyl-4-methyl-5-SCH₃ | 140 |
| 375 | — | S | i-C₃H₇ | (6-) CH₃ | 1,2,4-triazol-3(2H)-one, 2-methyl-4-methyl-5-CH₃ | 108 |
| 376 | — | O | CHF₂ | (4-) CH₃ | 1,3,4-oxadiazole, 2-methyl-5-CH₃ | 131 |

TABLE 1-continued
Examples of the compounds of the formula (I)
| Ex. No. | A | Q | R¹ | (position-) R² | R³ | Melting point (° C.) |
|---|---|---|---|---|---|---|
| 377 | — | O | CH₃ | (6-) CF₃ | 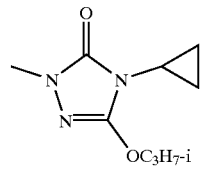 | 187 |
| 378 | — | O | CH₃ | (6-) CF₃ | 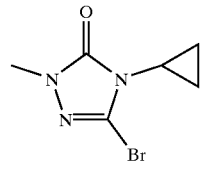 | 154 |
| 379 | — | O | CH₃ | (6-) C₂H₅ | 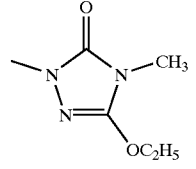 | 179 |
| 380 | — | O | CH₃ | (6-) C₂H₅ | 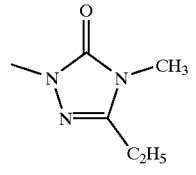 | 178 |
| 381 | — | O | CH₃ | (6-) C₂H₅ | 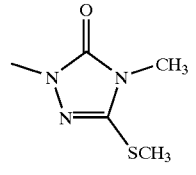 | 167 |
| 382 | — | O | C₂H₅ | (6-) C₂H₅ | 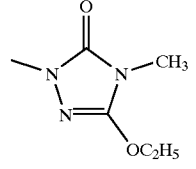 | 135 |
| 383 | — | O | C₂H₅ | (6-) C₂H₅ | 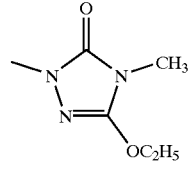 | 146 |
| 384 | — | O | C₂H₅ | (6-) C₂H₅ | 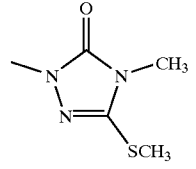 | 174 |

TABLE 1-continued

Examples of the compounds of the formula (I)

| Ex. No. | A | Q | R¹ | (position-) R² | R³ | Melting point (° C.) |
|---|---|---|---|---|---|---|
| 385 | — | O | $CH_3$ | (6-) $C_2H_5$ | 1-methyl-4-ethyl-5-methoxy-1,2,4-triazol-3(4H)-one | 130 |
| 386 | — | O | $CH_3$ | (6-) $C_2H_5$ | 1,4-dimethyl-5-methyl-1,2,4-triazol-3(4H)-one | 195 |
| 387 | — | O | $CH_3$ | (6-) $C_2H_5$ | 1,4-dimethyl-5-methoxy-1,2,4-triazol-3(4H)-one | 183 |
| 388 | — | O | $C_2H_5$ | (6-) $C_3H_7$-n | 1,4-dimethyl-5-ethoxy-1,2,4-triazol-3(4H)-one | 135 |
| 389 | — | O | $C_2H_5$ | (6-) $C_3H_7$-n | 1,4-dimethyl-5-methylthio-1,2,4-triazol-3(4H)-one | 149 |
| 390 | — | O | $CH_3$ | (6-) $C_3H_7$-n | 1,4-dimethyl-5-methyl-1,2,4-triazol-3(4H)-one | 193 |
| 391 | — | O | $CH_3$ | (6-) $C_3H_7$-n | 1-methyl-4-ethyl-5-methoxy-1,2,4-triazol-3(4H)-one | 125 |
| 392 | — | O | $CH_3$ | (6-) $C_3H_7$-n | 1,4-dimethyl-5-methoxy-1,2,4-triazol-3(4H)-one | 182 |

TABLE 1-continued

Examples of the compounds of the formula (I)

| Ex. No. | A | Q | R¹ | (position-) R² | R³ | Melting point (° C.) |
|---|---|---|---|---|---|---|
| 393 | — | O | $C_2H_5$ | (6-) $C_3H_7$-n | triazolinone with N-CH₃, N-CH₃, CH₃ | 120 |
| 394 | — | O | $C_2H_5$ | (6-) $C_3H_7$-n | triazolinone with N-CH₃, N-CH₃, OCH₃ | 158 |
| 395 | — | O | i-$C_3H_7$ | (6-) $CH_3$ | triazolinone with N-CH₃, N-CH₃, OC₆H₅ | 180 |
| 396 | — | O | n-$C_4H_9$ | (6-) $CH_3$ | triazolinone with N-CH₃, N-CH₃, OC₂H₅ | 132 |
| 397 | — | O | n-$C_4H_9$ | (6-) $CH_3$ | triazolinone with N-CH₃, N-CH₃, SCH₃ | 143 |
| 398 | — | O | n-$C_4H_9$ | (6-) $CH_3$ | triazolinone with N-CH₃, N-CH₃, C₂H₅ | 106 |
| 399 | — | O | n-$C_4H_9$ | (6-) $CH_3$ | triazolinone with N-CH₃, N-cyclopropyl, OC₂H₅ | 98 |
| 400 | — | O | n-$C_4H_9$ | (6-) $CH_3$ | triazolinone with N-CH₃, N-cyclopropyl, cyclopropyl | 140 |

TABLE 1-continued
Examples of the compounds of the formula (I)
| Ex. No. | A | Q | R¹ | (position-) R² | R³ | Melting point (° C.) |
|---|---|---|---|---|---|---|
| 401 | — | O | CH₃ | (6-) CH₃ | 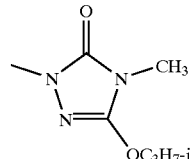 | 147 |
| 402 | — | O | CH₃ | (6-) CH₃ | 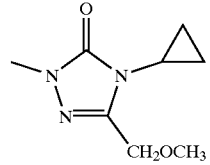 | 123 |
| 403 | — | O | CH₃ | (6-) CH₃ | 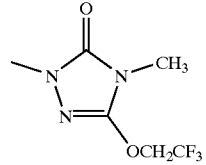 | 185 |
| 404 | — | O | CH₃ | (6-) CH₃ | 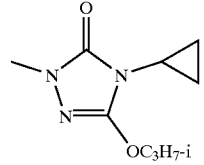 | 154 |
| 405 | NH | O | i-C₃H₇ | (6-) CH₃ | 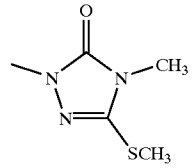 | 150 |
| 406 | — | O | C₂H₅ | (6-) C₂H₅ | 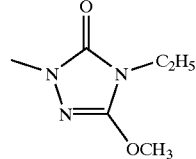 | 135 |
| 407 | — | O | C₂H₅ | (6-) C₂H₅ | 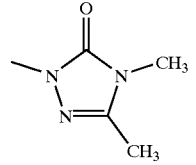 | 134 |
| 408 | — | O | C₂H₅ | (6-) C₂H₅ | 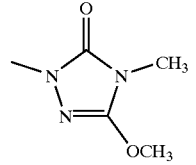 | 178 |

TABLE 1-continued

Examples of the compounds of the formula (I)

| Ex. No. | A | Q | R¹ | (position-) R² | R³ | Melting point (° C.) |
|---|---|---|---|---|---|---|
| 409 | — | O | $C_3H_7$-i | (6-) $C_2H_5$ | triazolinone with N-CH₃, N-CH₃, OC₂H₅ | 109 |
| 410 | — | O | $C_3H_7$-i | (6-) $C_2H_5$ | triazolinone with N-CH₃, N-CH₃, C₂H₅ | 125 |
| 411 | — | O | $C_3H_7$-i | (6-) $C_2H_5$ | triazolinone with N-CH₃, N-CH₃, SCH₃ | 161 |
| 412 | — | O | $C_3H_7$-i | (6-) $C_2H_5$ | triazolinone with N-CH₃, N-C₂H₅, OCH₃ | 114 |
| 413 | — | O | $C_3H_7$-i | (6-) $C_2H_5$ | triazolinone with N-CH₃, N-CH₃, CH₃ | 142 |
| 414 | — | O | $C_3H_7$-i | (6-) $C_2H_5$ | triazolinone with N-CH₃, N-CH₃, OCH₃ | 124 |
| 415 | — | O | $CH_3$ | (6-) $C_2H_5$ | triazolinone with N-CH₃, N-CH₃, OC₂H₅ | 175 (Na salt) |
| 416 | — | O | $C_2H_5$ | (6-) $C_3H_7$-n | triazolinone with N-CH₃, N-CH₃, C₂H₅ | 126 |

TABLE 1-continued

Examples of the compounds of the formula (I)

| Ex. No. | A | Q | R¹ | (position-) R² | R³ | Melting point (° C.) |
|---|---|---|---|---|---|---|
| 417 | — | O | C₂H₅ | (6-) C₃H₇-n | triazolinone with N-CH₃, N-C₂H₅, OCH₃ | 121 |
| 418 | — | O | CH₃ | (6-) C₃H₇-n | triazolinone with N-CH₃, N-C₂H₅, OC₂H₅ | 109 |
| 419 | — | O | CH₃ | (6-) C₃H₇-n | triazolinone with N-CH₃, N-OC₂H₅, C₂H₅ | 145 |
| 420 | — | O | CH₃ | (6-) C₃H₇-n | triazolinone with N-CH₃, N-OCH₃, C₃H₇-n | 126 |
| 421 | — | O | CH₃ | (6-) C₃H₇-n | triazolinone with N-CH₃, N-CH₃, OC₃H₇-n | 130 |
| 422 | — | O | CH₃ | (6-) C₃H₇-n | triazolinone with N-CH₃, N-CH₃, OCH₂CF₃ | 155 |
| 423 | — | O | CH₃ | (6-) C₃H₇-n | triazolinone with N-CH₃, N-CH₃, C₃H₇-i | 133 |
| 424 | — | O | CH₃ | (6-) C₃H₇-n | triazolinone with N-CH₃, N-CH₃, OC₃H₇-i | 145 |

TABLE 1-continued

Examples of the compounds of the formula (I)

| Ex. No. | A | Q | R¹ | (position-) R² | R³ | Melting point (° C.) |
|---|---|---|---|---|---|---|
| 425 | — | O | —SO$_2$CH$_3$ | (6-) CH$_3$ | 1,4-dimethyl-5-ethyl-1,2,4-triazol-3(2H)-one-2-yl | 95 |
| 426 | — | O | —SO$_2$CH$_3$ | (6-) CH$_3$ | 1,4-dimethyl-5-methylthio-1,2,4-triazol-3(2H)-one-2-yl | 153 |
| 427 | — | O | C$_4$H$_9$-n | (6-) CH$_3$ | 1,4-dimethyl-5-methoxy-1,2,4-triazol-3(2H)-one-2-yl | 154 |
| 428 | — | O | —CH$_2$C≡CH | (6-) CH$_3$ | 1,4-dimethyl-5-methoxy-1,2,4-triazol-3(2H)-one-2-yl | 167 |
| 429 | — | O | —CH$_2$C≡CH | (6-) CH$_3$ | 1,4-dimethyl-5-ethyl-1,2,4-triazol-3(2H)-one-2-yl | 170 |
| 430 | — | O | —CH$_2$C≡CH | (6-) CH$_3$ | 1,4-dimethyl-5-methylthio-1,2,4-triazol-3(2H)-one-2-yl | 153 |
| 431 | — | O | C$_4$H$_9$-i | (6-) CH$_3$ | 1,4-dimethyl-5-ethoxy-1,2,4-triazol-3(2H)-one-2-yl | 123 |
| 432 | — | O | C$_4$H$_9$-i | (6-) CH$_3$ | 1,4-dimethyl-5-ethyl-1,2,4-triazol-3(2H)-one-2-yl | 145 |

TABLE 1-continued

Examples of the compounds of the formula (I)

| Ex. No. | A | Q | R¹ | (position-) R² | R³ | Melting point (° C.) |
|---|---|---|---|---|---|---|
| 433 | — | O | $C_4H_9$-i | (6-) $CH_3$ | ![triazolinone with N-CH3, SCH3] | 143 |
| 434 | — | O | $C_3H_7$-i | (6-) $CH_3$ | ![triazolinone with N-CH2CH=CH2, H] | 138 |
| 435 | — | O | $C_3H_7$-i | (6-) $CH_3$ | ![triazolinone with N-CH3, OCH2C(CH3)3] | 161 |
| 436 | — | O | $C_3H_7$-i | (6-) $CH_3$ | ![triazolinone with N-cyclopropyl, CH2CH2OC3H7-i] | 128 |
| 437 | — | O | $C_3H_7$-i | (6-) $CH_3$ | ![triazolinone with N-CH3, cyclopropyl] | 177 |
| 438 | — | O | $C_3H_7$-i | (6-) $CH_3$ | ![triazolinone with N-CH3, OCH2CCl3] | 165 |
| 439 | — | O | $CH_3$ | (6-) $CH_3$ | ![triazolinone with N-cyclopropyl, OC2H5] | 157 |
| 440 | — | O | $CH_3$ | (6-) $CH_3$ | ![triazolinone with N-cyclopropyl, CH3] | 168 |

TABLE 1-continued

Examples of the compounds of the formula (I)

| Ex. No. | A | Q | R¹ | (position-) R² | R³ | Melting point (° C.) |
|---|---|---|---|---|---|---|
| 441 | — | O | CH₃ | (6-) CH₃ | (1-methyl-4-cyclopropyl-5-oxo-4,5-dihydro-1,2,4-triazol-3-yl, H at 3) | 164 |
| 442 | — | O | CH₃ | (6-) CH₃ | (1-methyl-4-cyclopropyl-5-oxo-4,5-dihydro-1,2,4-triazol-3-yl, OC₃H₇-n) | 125 |
| 443 | — | O | CH₃ | (6-) CH₃ | (1,4-dimethyl-5-oxo-4,5-dihydro-1,2,4-triazol-3-yl, H) | 162 |
| 444 | — | O | CH₃ | (6-) OCH₃ | (3,5-dimethyl-1,2,4-oxadiazol-yl) | 154 |
| 445 | — | S | CH₃ | (4-) C₃H₇-i | (1,4-dimethyl-5-oxo-4,5-dihydro-1,2,4-triazol-3-yl, SCH₃) | 116 |
| 446 | — | S | CH₃ | (4-) C₃H₇-i | (1,4-dimethyl-5-oxo-4,5-dihydro-1,2,4-triazol-3-yl, C₂H₅) | 110 |
| 447 | — | S | CH₃ | (4-) C₃H₇-i | (1,4-dimethyl-5-oxo-4,5-dihydro-1,2,4-triazol-3-yl, OC₂H₅) | 134 |
| 448 | — | O | CH₃ | (4-) C₃H₇-i | (1,4-dimethyl-5-oxo-4,5-dihydro-1,2,4-triazol-3-yl, SCH₃) | 152 |

TABLE 1-continued

Examples of the compounds of the formula (I)

| Ex. No. | A | Q | R¹ | (position-) R² | R³ | Melting point (° C.) |
|---|---|---|---|---|---|---|
| 449 | — | O | $CH_3$ | (4-) $C_3H_7$-i | 1-methyl-4-methyl-5-ethoxy-1,2,4-triazol-3(4H)-one | 159 |
| 450 | — | O | $CH_3$ | (4-) $C_3H_7$-i | 1-methyl-4-methyl-5-ethyl-1,2,4-triazol-3(4H)-one | 150 |
| 451 | — | O | $C_2H_5$ | (6-) $OCH_3$ | 1-methyl-4-methyl-5-ethyl-1,2,4-triazol-3(4H)-one | 107 |
| 452 | — | O | $C_2H_5$ | (6-) $OCH_3$ | 1-methyl-4-methyl-5-ethoxy-1,2,4-triazol-3(4H)-one | 104 |
| 453 | — | O | $C_2H_5$ | (6-) $OCH_3$ | 1-methyl-4-methyl-5-(2-methoxyphenoxy)-1,2,4-triazol-3(4H)-one | 100 |
| 454 | — | S | $C_2H_5$ | (6-) $OCH_3$ | 1-methyl-4-methyl-5-(methylthio)-1,2,4-triazol-3(4H)-one | 103 |
| 455 | — | S | $C_2H_5$ | (6-) $OCH_3$ | 1-methyl-4-methyl-5-ethyl-1,2,4-triazol-3(4H)-one | 95 |

TABLE 1-continued

Examples of the compounds of the formula (I)

| Ex. No. | A | Q | R¹ | (position-) R² | R³ | Melting point (° C.) |
|---|---|---|---|---|---|---|
| 456 | — | S | $C_2H_5$ | (6-) $OCH_3$ | 1-methyl-4-methyl-5-ethoxy-1,2,4-triazol-3(4H)-one | 105 |
| 457 | — | O | $C_2H_5$ | (6-) $OC_2H_5$ | 1-methyl-4-methyl-5-ethoxy-1,2,4-triazol-3(4H)-one | 130 |
| 458 | — | O | $C_2H_5$ | (6-) $OC_2H_5$ | 1-methyl-4-methyl-5-ethyl-1,2,4-triazol-3(4H)-one | 100 |
| 459 | — | O | $C_3H_7$-i | (6-) $OC_3H_7$-i | 1-methyl-4-methyl-5-methylthio-1,2,4-triazol-3(4H)-one | 114 |
| 460 | — | O | $C_3H_7$-i | (6-) $OC_3H_7$-i | 1-methyl-4-methyl-5-ethoxy-1,2,4-triazol-3(4H)-one | 125 |
| 461 | — | S | $C_3H_7$-i | (6-) $OC_3H_7$-i | 1-methyl-4-methyl-5-ethoxy-1,2,4-triazol-3(4H)-one | 143 |
| 462 | — | O | $C_2H_5$ | (6-) $OC_2H_5$ | 1-methyl-4-methyl-5-methyl-1,2,4-triazol-3(4H)-one | 120 |
| 463 | — | O | $-CF_2CHFCl$ | (6-) $CH_3$ | 1-methyl-4-methyl-5-ethyl-1,2,4-triazol-3(4H)-one | 124 |

TABLE 1-continued
Examples of the compounds of the formula (I)
| Ex. No. | A | Q | R¹ | (position-) R² | R³ | Melting point (° C.) |
|---|---|---|---|---|---|---|
| 464 | — | O | —CF₂CHFCl | (6-) CH₃ | 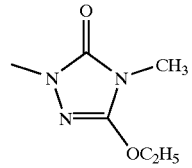 | 115 |
| 465 | — | O | —CF₂CHFCl | (6-) CH₃ | 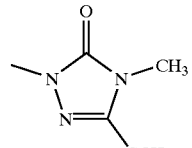 | 150 |
| 466 | — | O | CH₃ | (3-) CH₃ | 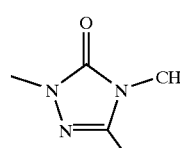 | 178 |
| 467 | — | O | CH₃ | (3-) Cl | 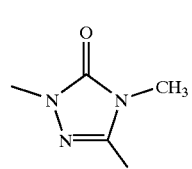 | 188 |
| 468 | — | O | C₂H₅ | (3-) Cl | 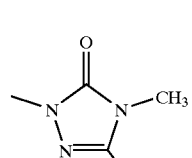 | 159 |
| 469 | — | O | CH₃ | (3-) F | 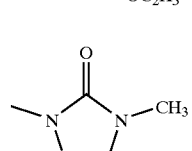 | 176 |
| 470 | — | O | C₂H₅ | (6-) CF₃ | 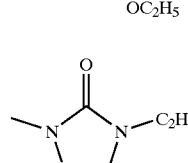 | 124 |
| 471 | — | O | C₂H₅ | (6-) CF₃ | 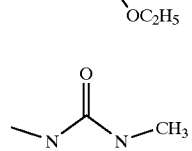 | 34 |

TABLE 1-continued

Examples of the compounds of the formula (I)

| Ex. No. | A | Q | R¹ | (position-) R² | R³ | Melting point (° C.) |
|---|---|---|---|---|---|---|
| 472 | — | O | $C_2H_5$ | (6-) $CF_3$ | ![structure: 1-methyl-4-methyl-5-(CH2OCH3)-1,2,4-triazol-3(2H)-one] | 68 |
| 473 | — | O | $C_3H_7$-i | (6-) $CF_3$ | ![structure: 1-methyl-4-cyclopropyl-5-(CH2OCH3)-1,2,4-triazol-3(2H)-one] | 41 |
| 474 | — | O | $C_2H_5$ | (6-) $CF_3$ | ![structure: 1-methyl-4-cyclopropyl-5-(OC2H5)-1,2,4-triazol-3(2H)-one] | 127 |
| 475 | — | O | H | (6-) $CF_3$ | ![structure: 1-methyl-4-methyl-5-(OC2H5)-1,2,4-triazol-3(2H)-one] | 125 |
| 476 | — | S | $C_2H_5$ | (6-) $CH_3$ | ![structure: 1-methyl-4-methyl-5-(OCH3)-1,2,4-triazol-3(2H)-one] | 214 (Na salt) |
| 477 | NH | O | $C_2H_5$ | (6-) $CH_3$ | ![structure: 1-methyl-4-cyclopropyl-5-(OC2H5)-1,2,4-triazol-3(2H)-one] | 128 |
| 478 | NH | O | $C_2H_5$ | (6-) $CH_3$ | ![structure: 1-methyl-4-methyl-5-(SCH3)-1,2,4-triazol-3(2H)-one] | 148 |
| 479 | NH | O | $C_3H_7$-n | (6-) $CH_3$ | ![structure: 1-methyl-4-methyl-5-(OC2H5)-1,2,4-triazol-3(2H)-one] | 127 |

TABLE 1-continued

Examples of the compounds of the formula (I)

| Ex. No. | A | Q | R¹ | (position-) R² | R³ | Melting point (° C.) |
|---|---|---|---|---|---|---|
| 480 | NH | O | $C_3H_7$-n | (6-) $CH_3$ | 1,4-dimethyl-5-ethyl-1,2,4-triazol-3(4H)-one-2-yl | 57 |
| 481 | NH | O | $C_2H_5$ | (6-) $CH_3$ | 1,4-dimethyl-5-methoxy-1,2,4-triazol-3(4H)-one-2-yl | 125 |
| 482 | NH | O | $C_3H_7$-n | (6-) $CH_3$ | 1,4-dimethyl-5-methylthio-1,2,4-triazol-3(4H)-one-2-yl | 115 |
| 483 | NH | O | $C_3H_7$-n | (6-) $CH_3$ | 1,4-dimethyl-5-methoxy-1,2,4-triazol-3(4H)-one-2-yl | 151 |
| 484 | NH | O | $C_2H_5$ | (5-) $CH_3$ | 1,4-dimethyl-5-ethoxy-1,2,4-triazol-3(4H)-one-2-yl | 132 |
| 485 | NH | O | $C_2H_5$ | (5-) $CH_3$ | 1,4-dimethyl-5-ethyl-1,2,4-triazol-3(4H)-one-2-yl | 106 |
| 486 | NH | O | $C_2H_5$ | (5-) $CH_3$ | 1,4-dimethyl-5-methylthio-1,2,4-triazol-3(4H)-one-2-yl | 163 |
| 487 | NH | O | $C_2H_5$ | (5-) $CH_3$ | 1,4-dimethyl-5-methoxy-1,2,4-triazol-3(4H)-one-2-yl | 137 |

TABLE 1-continued

Examples of the compounds of the formula (I)

| Ex. No. | A | Q | R¹ | (position-) R² | R³ | Melting point (° C.) |
|---|---|---|---|---|---|---|
| 488 | — | O | $C_2H_5$ | (6-) $C_3H_7$-i | triazolinone with N-CH₃, N-cyclopropyl, $OC_3H_7$-i | 166 |
| 489 | — | O | $C_2H_5$ | (6-) $C_3H_7$-i | triazolinone with N-CH₃, N-CH₃, $OC_2H_5$ | 169 |
| 490 | — | O | $C_2H_5$ | (6-) $C_3H_7$-i | triazolinone with N-CH₃, N-CH₃, $C_2H_5$ | 130 |
| 491 | NH | O | cyclopentylmethyl | (6-) $CH_3$ | triazolinone with N-CH₃, N-CH₃, $OC_2H_5$ | 148 |
| 492 | NH | O | cyclopentylmethyl | (6-) $CH_3$ | triazolinone with N-CH₃, N-CH₃, $C_2H_5$ | 138 |
| 493 | NH | O | cyclopentylmethyl | (6-) $CH_3$ | triazolinone with N-CH₃, N-CH₃, $SCH_3$ | 147 |
| 494 | — | O | cyclopentylmethyl | (6-) $CH_3$ | triazolinone with N-CH₃, N-CH₃, $C_2H_5$ | 124 |
| 495 | — | O | cyclopentylmethyl | (6-) $CH_3$ | triazolinone with N-CH₃, N-CH₃, $SCH_3$ | 152 |

TABLE 1-continued

Examples of the compounds of the formula (I)

| Ex. No. | A | Q | R¹ | (position-) R² | R³ | Melting point (° C.) |
|---|---|---|---|---|---|---|
| 496 | — | O | cyclopentyl-CH₂ | (6-) CH₃ | 1-methyl-4-cyclopropyl-5-isopropoxy-1,2,4-triazol-3(4H)-one | 141 |
| 497 | — | O | cyclopentyl-CH₂ | (6-) CH₃ | 1-methyl-4-cyclopropyl-5-ethoxy-1,2,4-triazol-3(4H)-one | 127 |
| 498 | — | O | cyclopentyl-CH₂ | (6-) CH₃ | 1,4-dimethyl-5-methyl-1,2,4-triazol-3(4H)-one | 144 |
| 499 | — | O | cyclopentyl-CH₂ | (6-) CH₃ | 1-methyl-4-cyclopropyl-5-methyl-1,2,4-triazol-3(4H)-one | 107 |
| 500 | — | O | $C_3H_7$-n | (6-) CH₃ | 1-methyl-4-dimethylamino-5-methyl-1,2,4-triazol-3(4H)-one | 265 (Na salt) |
| 501 | — | O | $C_2H_5$ | (6-) CH₃ | 1-methyl-4-dimethylamino-5-methyl-1,2,4-triazol-3(4H)-one | 269 (Na salt) |
| 502 | — | O | $C_3H_7$-i | (6-) CH₃ | 1-methyl-4-dimethylamino-5-methyl-1,2,4-triazol-3(4H)-one | 237 (Na salt) |
| 503 | — | O | cyclopentyl-CH₂ | (6-) CH₃ | 3,5-dimethyl-1,3,4-oxadiazole | 73 |

TABLE 1-continued

Examples of the compounds of the formula (I)

| Ex. No. | A | Q | R¹ | (position-) R² | R³ | Melting point (° C.) |
|---|---|---|---|---|---|---|
| 504 | — | O | $C_3H_7$-i | (6-) $CH_3$ | 1,2-dimethyl-5-ethoxy-1,2,4-triazol-3(2H)-one-4-yl | 220 (Na salt) |
| 505 | — | O | $C_3H_7$-i | (6-) $CH_3$ | 4-amino-5-cyclopropyl-2-methyl-1,2,4-triazol-3(2H)-one-yl | 140 |
| 506 | — | O | $C_4H_9$-s | (6-) $CH_3$ | 1,2-dimethyl-5-ethoxy-1,2,4-triazol-3(2H)-one-4-yl | 120 |
| 507 | — | O | $C_4H_9$-s | (6-) $CH_3$ | 1,2-dimethyl-5-methylthio-1,2,4-triazol-3(2H)-one-4-yl | 117 |
| 508 | — | O | $C_4H_9$-s | (6-) $CH_3$ | 1,2,5-trimethyl-1,2,4-triazol-3(2H)-one-4-yl | 128 |
| 509 | — | O | $C_4H_9$-s | (6-) $CH_3$ | 1,2-dimethyl-5-methoxy-1,2,4-triazol-3(2H)-one-4-yl | 232 |
| 510 | — | O | $C_4H_9$-s | (6-) $CH_3$ | 4,5-dicyclopropyl-2-methyl-1,2,4-triazol-3(2H)-one-yl | 268 |
| 511 | — | O | $C_4H_9$-s | (6-) $CH_3$ | 4-ethyl-5-isopropoxy-2-methyl-1,2,4-triazol-3(2H)-one-yl | 130 |

TABLE 1-continued
Examples of the compounds of the formula (I)
| Ex. No. | A | Q | R¹ | (position-) R² | R³ | Melting point (° C.) |
|---|---|---|---|---|---|---|
| 512 | — | O | $C_4H_9$-s | (6-) $CH_3$ | 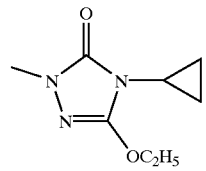 | 137 |
| 513 | — | O | $C_4H_9$-s | (6-) $CH_3$ | 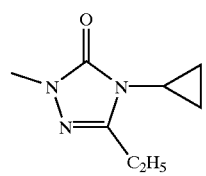 | 145 |
| 514 | — | O | $C_4H_9$-s | (6-) $CH_3$ | 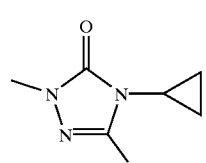 | 164 |
| 515 | — | O | $C_4H_9$-s | (6-) $CH_3$ | 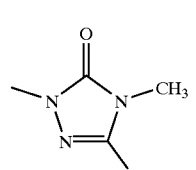 | 89 |
| 516 | — | O | $C_4H_9$-s | (6-) $CH_3$ | 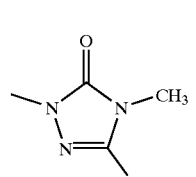 | 86 |
| 517 | — | O | $C_4H_9$-s | (6-) $CH_3$ | 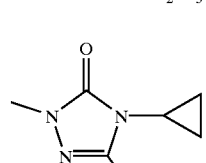 | 98 |
| 518 | — | O | $C_4H_9$-s | (6-) $CH_3$ | 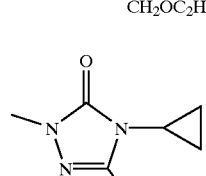 | 122 |
| 519 | — | O | $C_4H_9$-s | (6-) $CH_3$ | 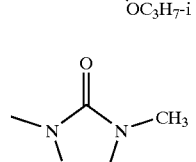 | 135 |

TABLE 1-continued
Examples of the compounds of the formula (I)
| Ex. No. | A | Q | R¹ | (position-) R² | R³ | Melting point (° C.) |
|---|---|---|---|---|---|---|
| 520 | — | O | C₂H₅ | (6-) CH₃ | 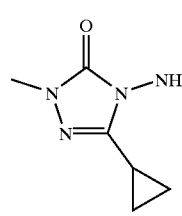 | 142 |
| 521 | — | O | CH₃ | (6-) CH₃ | 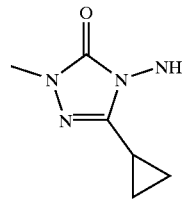 | 157 |
| 522 | — | O | C₃H₇-n | (6-) CH₃ | 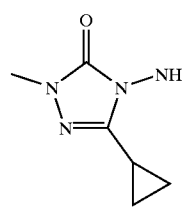 | 126 |
| 523 | — | O | C₄H₉-s | (6-) CH₃ | 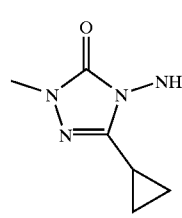 | 140 |
| 524 | — | O | C₂H₅ | (6-) CH₃ | 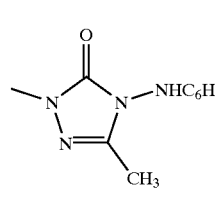 | 164 |
| 525 | — | O | CH₃ | (6-) CH₃ | 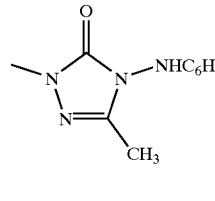 | 166 |
| 526 | — | O | C₃H₇-n | (6-) CH₃ | 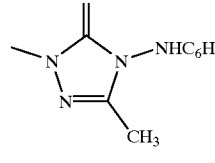 | 145 |

TABLE 1-continued

Examples of the compounds of the formula (I)

| Ex. No. | A | Q | R¹ | (position-) R² | R³ | Melting point (° C.) |
|---|---|---|---|---|---|---|
| 527 | — | O | CH₃ | (6-) CH₃ | | 239 (Na salt) |
| 528 | — | O | C₃H₇-n | (6-) CH₃ | | 206 (Na salt) |
| 529 | — | O | C₂H₅ | (6-) CH₃ | | 211 (Na salt) |
| 530 | — | O | CH₃ | (6-) C₃H₇-i | | 166 |
| 531 | — | O | CH₃ | (6-) C₃H₇-i | | 178 |
| 532 | — | O | C₃H₇-i | (6-) C₃H₇-i | | 131 |
| 533 | — | O | C₃H₇-i | (6-) C₃H₇-i | | 130 |

TABLE 1-continued
Examples of the compounds of the formula (I)
| Ex. No. | A | Q | R¹ | (position-) R² | R³ | Melting point (° C.) |
|---|---|---|---|---|---|---|
| 534 | — | O | $C_3H_7$-i | (6-) $C_3H_7$-i | 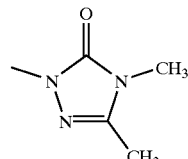 | 133 |
| 535 | — | O | $C_3H_7$-i | (6-) $C_3H_7$-i | 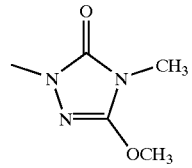 | 116 |
| 536 | — | O | $CH_3$ | (6-) $C_3H_7$-i | 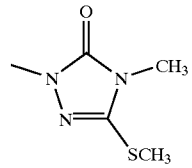 | 192 |
| 537 | — | O | $CH_3$ | (6-) $C_3H_7$-i | 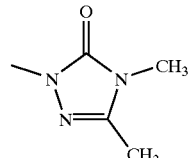 | 200 |
| 538 | — | O | $CH_3$ | (6-) $C_3H_7$-i | 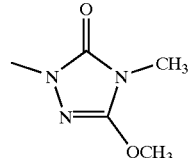 | 200 |
| 539 | — | O | $CH_3$ | (6-) $C_3H_7$-i | 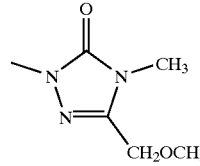 | 105 |
| 540 | — | O | $CH_3$ | (6-) $C_3H_7$-i | 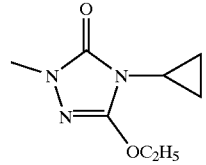 | 154 |
| 541 | — | O | $CH_3$ | (6-) $C_3H_7$-i | 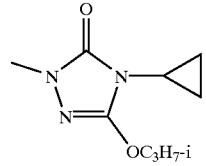 | 152 |

TABLE 1-continued

Examples of the compounds of the formula (I)

| Ex. No. | A | Q | R$^1$ | (position-) R$^2$ | R$^3$ | Melting point (° C.) |
|---|---|---|---|---|---|---|
| 542 | — | O | C$_3$H$_7$-n | (6-) C$_3$H$_7$-i | 1,4-dimethyl-5-ethoxy-1,2,4-triazol-3(2H)-one-2-yl | 132 |
| 543 | — | O | C$_3$H$_7$-n | (6-) C$_3$H$_7$-i | 1,4-dimethyl-5-ethyl-1,2,4-triazol-3(2H)-one-2-yl | 129 |
| 544 | — | O | C$_3$H$_7$-n | (6-) C$_3$H$_7$-i | 1,4-dimethyl-5-methylthio-1,2,4-triazol-3(2H)-one-2-yl | 179 |
| 545 | — | O | CH$_3$ | (6-) C$_3$H$_7$-i | 1,4-dimethyl-5-ethoxy-1,2,4-triazol-3(2H)-one-2-yl | 174 (Na salt) |
| 546 | — | O | C$_3$H$_7$-n | (6-) C$_3$H$_7$-i | 1,4-dimethyl-5-ethoxy-1,2,4-triazol-3(2H)-one-2-yl | 158 (Na salt) |
| 547 | — | O | C$_2$H$_5$ | (6-) C$_3$H$_7$-i | 1,4-dimethyl-5-methylthio-1,2,4-triazol-3(2H)-one-2-yl | 200 |
| 548 | — | O | C$_2$H$_5$ | (6-) C$_3$H$_7$-i | 1,4,5-trimethyl-1,2,4-triazol-3(2H)-one-2-yl | 147 |
| 549 | — | O | C$_2$H$_5$ | (6-) C$_3$H$_7$-i | 1,4-dimethyl-5-methoxy-1,2,4-triazol-3(2H)-one-2-yl | 149 |

TABLE 1-continued

Examples of the compounds of the formula (I)

| Ex. No. | A | Q | R¹ | (position-) R² | R³ | Melting point (° C.) |
|---|---|---|---|---|---|---|
| 550 | — | O | $C_2H_5$ | (6-) $C_3H_7$-i | triazolinone with N–CH₃, N–CH₃, C–CH₂OCH₃ | 136 |
| 551 | — | O | $C_2H_5$ | (6-) $C_3H_7$-i | triazolinone with N–CH₃, N–cyclopropyl, C–OC₂H₅ | 134 |
| 552 | — | O | $C_3H_7$-i | (6-) $C_3H_7$-i | triazolinone with N–CH₃, N–cyclopropyl, C–CH₃ | 175 |
| 553 | — | O | $C_3H_7$-i | (6-) $C_3H_7$-i | triazolinone with N–CH₃, N–cyclopropyl, C–cyclopropyl | 147 |
| 554 | — | O | $C_3H_7$-i | (6-) $C_3H_7$-i | triazolinone with N–CH₃, N–cyclopropyl, C–OC₃H₇-i | 167 |
| 555 | — | O | $C_3H_7$-i | (6-) $C_3H_7$-i | triazolinone with N–CH₃, N–CH₃, C–SCH₃ | 173 |
| 556 | — | O | $C_3H_7$-i | (6-) $CH_3$ | triazolinone with N–CH₃, N–NH–CO–CH₃, C–cyclopropyl | 188 |
| 557 | NH | O | $CH_3$ | (6-) $CH_3$ | triazolinone with N–CH₃, N–cyclopropyl, C–OC₂H₅ | 181 |

TABLE 1-continued

Examples of the compounds of the formula (I)

| Ex. No. | A | Q | R¹ | (position-) R² | R³ | Melting point (° C.) |
|---|---|---|---|---|---|---|
| 558 | NH | O | $C_3H_7$-i | (6-) $CH_3$ | 1-methyl-4-cyclopropyl-5-ethoxy-1,2,4-triazol-3(4H)-one | 136 |
| 559 | — | O | $CH_3$ | (6-) $CH_3$ | 1,4-dimethyl-5-ethoxy-1,2,4-triazol-3(4H)-one | 241 (Na salt) |
| 560 | NH | O | $C_3H_7$-n | (6-) $CH_3$ | 1-methyl-4-cyclopropyl-5-ethoxy-1,2,4-triazol-3(4H)-one | 129 |
| 561 | — | O | $C_3H_7$-i | (6-) $OCH_3$ | 1,4-dimethyl-5-methylthio-1,2,4-triazol-3(4H)-one | 94 |
| 562 | — | O | $C_3H_7$-i | (6-) $OCH_3$ | 1,4-dimethyl-5-ethyl-1,2,4-triazol-3(4H)-one | 80 |
| 563 | — | O | $C_3H_7$-i | (6-) $OC_2H_5$ | 1,4-dimethyl-5-ethyl-1,2,4-triazol-3(4H)-one | 68 |
| 564 | — | O | $C_3H_7$-i | (6-) $OC_2H_5$ | 1,4-dimethyl-5-ethyl-1,2,4-triazol-3(4H)-one | 91 |
| 565 | — | O | $C_3H_7$-n | (6-) $OCH_3$ | 1-methyl-4-cyclopropyl-5-methoxy-1,2,4-triazol-3(4H)-one | 123 |

TABLE 1-continued

Examples of the compounds of the formula (I)

| Ex. No. | A | Q | R$^1$ | (position-) R$^2$ | R$^3$ | Melting point (° C.) |
|---|---|---|---|---|---|---|
| 566 | — | O | C$_3$H$_7$-n | (6-) OCH$_3$ | triazolinone with N-CH$_3$, N-CH$_3$, OC$_2$H$_5$ | 104 |
| 567 | — | O | C$_3$H$_7$-n | (6-) OCH$_3$ | triazolinone with N-CH$_3$, N-CH$_3$, C$_2$H$_5$ | 90 |
| 568 | — | S | C$_3$H$_7$-n | (6-) OCH$_3$ | triazolinone with N-CH$_3$, N-CH$_3$, C$_2$H$_5$ | 107 |
| 569 | — | O | C$_3$H$_7$-n | (6-) OCH$_3$ | oxadiazole with CH$_3$ | 70 |
| 570 | — | O | C$_2$H$_5$ | (6-) OC$_2$H$_5$ | triazolinone with N-CH$_3$, N-CH$_3$, SCH$_3$ | 132 |
| 571 | — | S | CH$_3$ | (6-) OCH$_3$ | triazolinone with N-CH$_3$, N-CH$_3$, OC$_2$H$_5$ | 150 |
| 572 | — | O | C$_2$H$_5$ | (6-) OCH$_3$ | oxadiazole with CH$_3$ | 127 |
| 573 | — | O | C$_3$H$_7$-i | (6-) OC$_3$H$_7$-i | triazolinone with N-CH$_3$, N-CH$_3$, C$_2$H$_5$ | 110 |

TABLE 1-continued
Examples of the compounds of the formula (I)
| Ex. No. | A | Q | $R^1$ | (position-) $R^2$ | $R^3$ | Melting point (° C.) |
|---|---|---|---|---|---|---|
| 574 | — | S | $C_3H_7$-n | (6-) $OC_3H_7$-n | 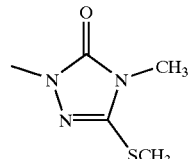 | 130 |
| 575 | — | S | $C_3H_7$-n | (6-) $OC_3H_7$-n | 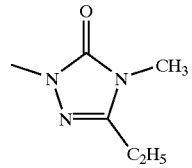 | 135 |
| 576 | — | S | $C_3H_7$-n | (6-) $OC_3H_7$-n | 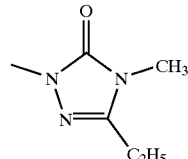 | 199 (Na salt) |
| 577 | — | O | $C_2H_5$ | (6-) $OC_2H_5$ | 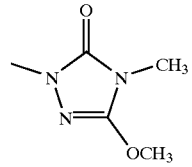 | 173 |
| 578 | — | O | $C_2H_5$ | (6-) $OCH_3$ | 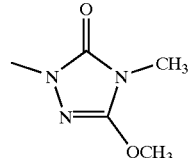 | 168 |
| 579 | — | O | $C_3H_7$-n | (6-) $OC_3H_7$-n | 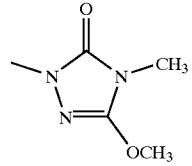 | 125 |
| 580 | — | O | $C_3H_7$-n | (6-) $OC_2H_5$ | 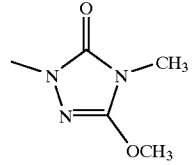 | 140 |
| 581 | — | O | $C_3H_7$-n | (6-) $OCH_3$ | 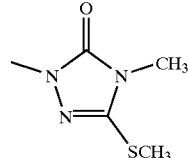 | 115 |

TABLE 1-continued
Examples of the compounds of the formula (I)
| Ex. No. | A | Q | R¹ | (position-) R² | R³ | Melting point (° C.) |
|---|---|---|---|---|---|---|
| 582 | — | S | C₃H₇-n | (6-) OCH₃ | 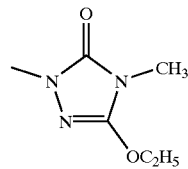 | 111 |
| 583 | — | S | C₃H₇-n | (6-) OCH₃ | 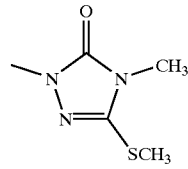 | 138 |
| 584 | — | O | C₃H₇-i | (6-) OCH₃ | 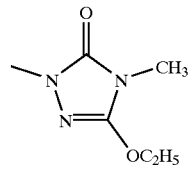 | 127 |
| 585 | — | O | C₃H₇-i | (6-) OC₂H₅ | 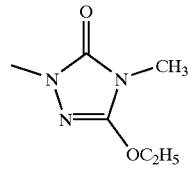 | 142 |
| 586 | — | O | C₃H₇-i | (6-) OC₂H₅ | 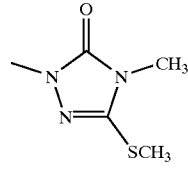 | 143 |
| 587 | — | O | C₂H₅ | (6-) OCH₃ | 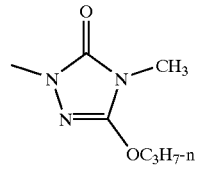 | 104 |
| 588 | — | O | C₂H₅ | (6-) OCH₃ | 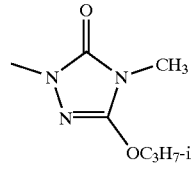 | 118 |
| 589 | — | O | C₂H₅ | (6-) OCH₃ | 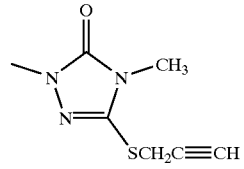 | 70 |

TABLE 1-continued

Examples of the compounds of the formula (I)

| Ex. No. | A | Q | R¹ | (position-) R² | R³ | Melting point (° C.) |
|---|---|---|---|---|---|---|
| 590 | — | O | $C_2H_5$ | (6-) $OCH_3$ | 1,2,4-triazol-3(2H)-one, 2-methyl, 4-CH₃, 5-$C_3H_7$-n | 110 |
| 591 | — | O | $C_2H_5$ | (6-) $OCH_3$ | 1,2,4-triazol-3(2H)-one, 2-methyl, 4-$C_2H_5$, 5-$OCH_3$ | 156 |
| 592 | — | O | $C_3H_7$-n | (6-) $OCH_3$ | 1,2,4-triazol-3(2H)-one, 2-methyl, 4-CH₃, 5-Br | 140 |
| 593 | — | O | $C_3H_7$-n | (6-) $OCH_3$ | 1,2,4-triazol-3(2H)-one, 2-methyl, 4-CH₃, 5-$OCH_3$ | 148 |
| 594 | — | O | $C_3H_7$-n | (6-) $OCH_3$ | 1,2,4-triazol-3(2H)-one, 2-methyl, 4-CH₃, 5-$OCH_2CF_3$ | 145 |
| 595 | — | O | $C_2H_5$ | (6-) $OCH_3$ | 1,2,4-triazol-3(2H)-one, 2-methyl, 4-CH₃, 5-$OCH_2CF_3$ | 120 |
| 596 | — | O | $C_2H_5$ | (6-) $OCH_3$ | 1,2,4-triazol-3(2H)-one, 2-methyl, 4-cyclopropyl, 5-$OC_2H_5$ | 100 |
| 597 | — | O | $C_2H_5$ | (6-) $OCH_3$ | 1,2,4-triazol-3(2H)-one, 2-methyl, 4-CH₃, 5-$SCH_3$ | 130 |

TABLE 1-continued

Examples of the compounds of the formula (I)

| Ex. No. | A | Q | R¹ | (position-) R² | R³ | Melting point (° C.) |
|---|---|---|---|---|---|---|
| 598 | — | O | $C_2H_5$ | (6-) $OCH_3$ | N-methyl-4-cyclopropyl-5-bromo-1,2,4-triazol-3(4H)-one | 103 |
| 599 | — | O | $C_2H_5$ | (6-) $OCH_3$ | N-methyl-4-cyclopropyl-5-($CH_2OCH_3$)-1,2,4-triazol-3(4H)-one | 104 |
| 600 | — | O | $C_3H_7$-n | (6-) $OCH_3$ | N-methyl-4-$CH_3$-5-$CH_3$-1,2,4-triazol-3(4H)-one | 185 |
| 601 | — | O | $C_3H_7$-n | (6-) $OCH_3$ | N-methyl-4-$OC_2H_5$-5-$C_2H_5$-1,2,4-triazol-3(4H)-one | 100 |
| 602 | — | O | $C_3H_7$-n | (6-) $OCH_3$ | N-methyl-4-cyclopropyl-5-Br-1,2,4-triazol-3(4H)-one | 138 |
| 603 | — | O | $C_3H_7$-n | (6-) $OCH_3$ | N-methyl-4-$CH_3$-5-$OC_3H_7$-n-1,2,4-triazol-3(4H)-one | 106 |
| 604 | — | O | $C_3H_7$-n | (6-) $OCH_3$ | N-methyl-4-cyclopropyl-5-$OC_2H_5$-1,2,4-triazol-3(4H)-one | 112 |
| 605 | — | O | $C_3H_7$-n | (6-) $OCH_3$ | N-methyl-4-$CH_3$-5-$SCH_2C\equiv CH$-1,2,4-triazol-3(4H)-one | 140 |

TABLE 1-continued
Examples of the compounds of the formula (I)
| Ex. No. | A | Q | R¹ | (position-) R² | R³ | Melting point (° C.) |
|---|---|---|---|---|---|---|
| 606 | — | O | C₃H₇-n | (6-) OCH₃ | 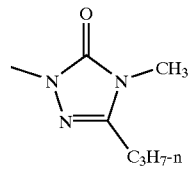 | 160 |
| 607 | — | O | C₃H₇-n | (6-) OCH₃ | 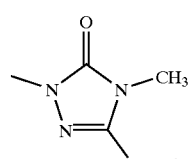 | 180 |
| 608 | — | O | C₃H₇-n | (6-) OCH₃ | 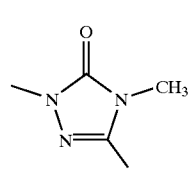 | 142 |
| 609 | — | O | C₃H₇-n | (6-) OCH₃ | 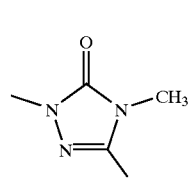 | 158 |
| 610 | — | O | C₃H₇-n | (6-) OCH₃ | 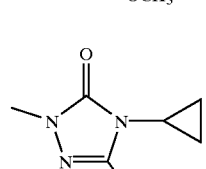 | 134 |
| 611 | — | O | C₃H₇-i | (6-) OCH₃ | 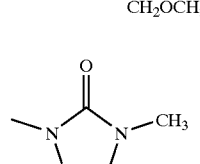 | 140 |
| 612 | — | O | C₃H₇-i | (6-) OCH₃ | 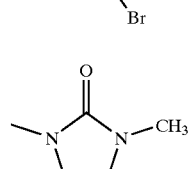 | 142 |
| 613 | — | O | C₃H₇-i | (6-) OCH₃ | 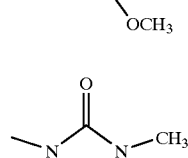 | 148 |

TABLE 1-continued
Examples of the compounds of the formula (I)
| Ex. No. | A | Q | R¹ | (position-) R² | R³ | Melting point (° C.) |
|---|---|---|---|---|---|---|
| 614 | — | O | $C_3H_7$-i | (6-) $OCH_3$ | 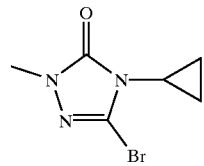 | 146 |
| 615 | — | O | $C_3H_7$-i | (6-) $OCH_3$ | 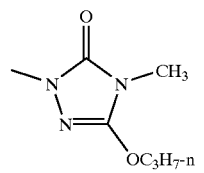 | 104 |
| 616 | — | O | $C_2H_5$ | (6-) $OC_2H_5$ | 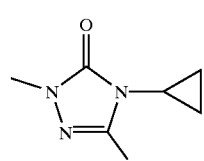 | 123 |
| 617 | — | O | $C_3H_7$-n | (6-) $OC_3H_7$-n | 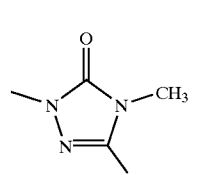 | 123 |
| 618 | — | O | $C_3H_7$-n | (6-) $OC_3H_7$-n | 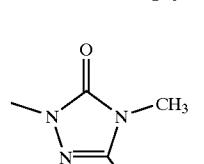 | 82 |
| 619 | — | O | $C_3H_7$-n | (6-) $OC_3H_7$-n | 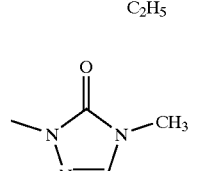 | 81 |
| 620 | — | S | $C_3H_7$-n | (6-) $OC_3H_7$-n | 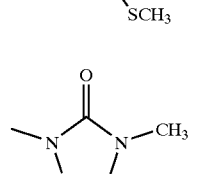 | 88 |
| 621 | — | S | $C_2H_5$ | (6-) $OCH_3$ | 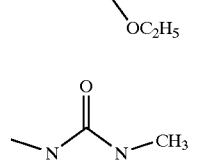 | 145 |

TABLE 1-continued

Examples of the compounds of the formula (I)

| Ex. No. | A | Q | R¹ | (position-) R² | R³ | Melting point (° C.) |
|---|---|---|---|---|---|---|
| 622 | — | S | $C_2H_5$ | (6-) $OC_2H_5$ | ![triazolinone with N-CH3, OC3H7-n] | 147 |
| 623 | — | S | $C_3H_7$-n | (6-) $OCH_3$ | ![triazolinone with N-CH3, OC3H7-n] | 205 |
| 624 | — | S | $C_3H_7$-n | (6-) $OC_2H_5$ | ![triazolinone with N-CH3, OC3H7-n] | 202 |
| 625 | — | S | $C_3H_7$-i | (6-) $OC_3H_7$-i | ![triazolinone with N-CH3, OC3H7-n] | 152 |
| 626 | — | S | $C_2H_5$ | (6-) $OC_2H_5$ | ![triazolinone with N-CH3, OCH3] | 168 |
| 627 | — | S | $C_3H_7$-n | (6-) $C_3H_7$-n | ![triazolinone with N-CH3, OCH3] | 145 |
| 628 | — | S | $C_3H_7$-n | (6-) $OCH_3$ | ![triazolinone with N-CH3, OCH3] | 158 |
| 629 | — | S | $C_3H_7$-i | (6-) $OC_3H_7$-i | ![triazolinone with N-CH3, OCH3] | 155 |

TABLE 1-continued

Examples of the compounds of the formula (I)

| Ex. No. | A | Q | R¹ | (position-) R² | R³ | Melting point (° C.) |
|---|---|---|---|---|---|---|
| 630 | — | O | $C_3H_7$-i | (6-) $OCH_3$ | (1-methyl-4-cyclopropyl-5-ethoxy-1,2,4-triazol-3(4H)-one) | 145 |
| 631 | — | O | $C_3H_7$-i | (6-) $OCH_3$ | (1-methyl-4-methyl-5-(propargylthio)-1,2,4-triazol-3(4H)-one; $SCH_2C{\equiv}CH$) | 111 |
| 632 | — | O | $C_3H_7$-i | (6-) $OCH_3$ | (1-methyl-4-methyl-5-n-propyl-1,2,4-triazol-3(4H)-one; $C_3H_7$-n) | 122 |
| 633 | — | O | $C_3H_7$-i | (6-) $OCH_3$ | (1-methyl-4-methyl-5-isopropoxy-1,2,4-triazol-3(4H)-one; $OC_3H_7$-i) | 171 |
| 634 | — | O | $C_3H_7$-i | (6-) $OCH_3$ | (1-methyl-4-ethyl-5-methoxy-1,2,4-triazol-3(4H)-one; $C_2H_5$, $OCH_3$) | 160 |
| 635 | — | O | $C_3H_7$-i | (6-) $OCH_3$ | (1-methyl-4-cyclopropyl-5-(methoxymethyl)-1,2,4-triazol-3(4H)-one; $CH_2OCH_3$) | 142 |
| 636 | — | O | $C_2H_5$ | (6-) $OC_2H_5$ | (1-methyl-4-methyl-5-(2,2,2-trifluoroethoxy)-1,2,4-triazol-3(4H)-one; $OCH_2CF_3$) | 106 |
| 637 | — | O | $C_2H_5$ | (6-) $OC_2H_5$ | (1-methyl-4-ethoxy-5-ethyl-1,2,4-triazol-3(4H)-one; $OC_2H_5$, $C_2H_5$) | 106 |

TABLE 1-continued

Examples of the compounds of the formula (I)

| Ex. No. | A | Q | R¹ | (position-) R² | R³ | Melting point (° C.) |
|---|---|---|---|---|---|---|
| 638 | — | O | $C_2H_5$ | (6-) $OC_2H_5$ | 1-methyl-4-cyclopropyl-5-bromo-1,2,4-triazol-3(4H)-one | 159 |
| 639 | — | O | $C_2H_5$ | (6-) $OC_2H_5$ | 1-methyl-4-methyl-5-(n-propoxy)-1,2,4-triazol-3(4H)-one | 148 |
| 640 | — | O | $C_2H_5$ | (6-) $OC_2H_5$ | 1-methyl-4-cyclopropyl-5-ethoxy-1,2,4-triazol-3(4H)-one | 126 |
| 641 | — | O | $C_2H_5$ | (6-) $OC_2H_5$ | 1-methyl-4-methyl-5-(n-propyl)-1,2,4-triazol-3(4H)-one | 111 |
| 642 | — | O | $C_2H_5$ | (6-) $OC_2H_5$ | 1-methyl-4-methyl-5-(i-propoxy)-1,2,4-triazol-3(4H)-one | 171 |
| 643 | — | O | $C_2H_5$ | (6-) $OC_2H_5$ | 1-methyl-4-methyl-5-(methoxymethyl)-1,2,4-triazol-3(4H)-one | 127 |
| 644 | — | O | $C_2H_5$ | (6-) $OC_2H_5$ | 1-methyl-4-ethyl-5-methoxy-1,2,4-triazol-3(4H)-one | 148 |
| 645 | — | O | $C_2H_5$ | (6-) $OC_2H_5$ | 1-methyl-4-cyclopropyl-5-(methoxymethyl)-1,2,4-triazol-3(4H)-one | 123 |

TABLE 1-continued
Examples of the compounds of the formula (I)
| Ex. No. | A | Q | R¹ | (position-) R² | R³ | Melting point (° C.) |
|---|---|---|---|---|---|---|
| 646 | — | O | $C_3H_7$-n | (6-) $OC_3H_7$-n | 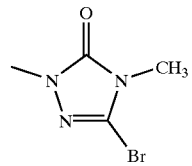 | 138 |
| 647 | — | O | $C_3H_7$-n | (6-) $OC_3H_7$-n | 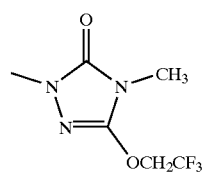 | 95 |
| 648 | — | O | $C_3H_7$-n | (6-) $OC_3H_7$-n | 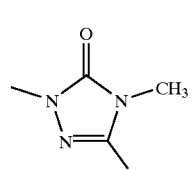 | 130 |
| 649 | — | O | $C_3H_7$-n | (6-) $OC_3H_7$-n | 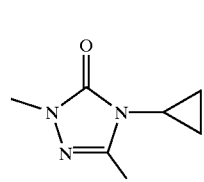 | 74 |
| 650 | — | O | $C_3H_7$-n | (6-) $OC_3H_7$-n | 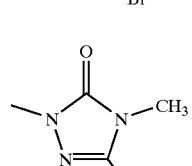 | 109 |
| 651 | — | O | $C_3H_7$-n | (6-) $OC_3H_7$-n | 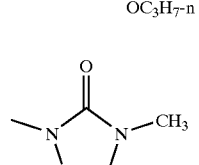 | 75 |
| 652 | — | O | $C_3H_7$-n | (6-) $OC_3H_7$-n | 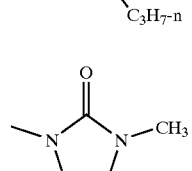 | 147 |
| 653 | — | O | $C_3H_7$-n | (6-) $OC_3H_7$-n | 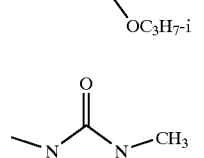 | 99 |

TABLE 1-continued

Examples of the compounds of the formula (I)

| Ex. No. | A | Q | R¹ | (position-) R² | R³ | Melting point (° C.) |
|---|---|---|---|---|---|---|
| 654 | — | O | $C_3H_7$-n | (6-) $OC_3H_7$-n | (1-methyl-4-ethyl-5-methoxy-1,2,4-triazol-3(4H)-one) | 102 |
| 655 | — | O | $C_3H_7$-n | (6-) $OC_3H_7$-n | (1-methyl-4-cyclopropyl-5-methoxymethyl-1,2,4-triazol-3(4H)-one) | 98 |
| 656 | — | O | $C_3H_7$-i | (6-) $OC_3H_7$-i | (1-methyl-4-methyl-5-bromo-1,2,4-triazol-3(4H)-one) | 138 |
| 657 | — | O | $C_3H_7$-i | (6-) $OC_3H_7$-i | (1-methyl-4-methyl-5-methoxy-1,2,4-triazol-3(4H)-one) | 127 |
| 658 | — | O | $C_3H_7$-i | (6-) $OC_3H_7$-i | (1-methyl-4-methyl-5-$OCH_2CF_3$-1,2,4-triazol-3(4H)-one) | 160 |
| 659 | — | O | $C_3H_7$-i | (6-) $OC_3H_7$-i | (1-methyl-4-methyl-5-methyl-1,2,4-triazol-3(4H)-one) | 115 |
| 660 | — | O | $C_3H_7$-i | (6-) $OC_3H_7$-i | (1-methyl-4-$OC_2H_5$-5-$C_2H_5$-1,2,4-triazol-3(4H)-one) | 108 |
| 661 | — | O | $C_3H_7$-i | (6-) $OC_3H_7$-i | (1-methyl-4-cyclopropyl-5-bromo-1,2,4-triazol-3(4H)-one) | 154 |

TABLE 1-continued

Examples of the compounds of the formula (I)

| Ex. No. | A | Q | R¹ | (position-) R² | R³ | Melting point (° C.) |
|---|---|---|---|---|---|---|
| 662 | — | O | $C_3H_7$-i | (6-) $OC_3H_7$-i | triazolone with N-CH₃, N-CH₃, O$C_3H_7$-n | 144 |
| 663 | — | O | $C_2H_4OC_2H_5$ | (6-) $OCH_3$ | triazolone with N-CH₃, N-CH₃, O$C_2H_5$ | 124 |
| 664 | — | O | $C_2H_4OC_2H_5$ | (6-) $OCH_3$ | triazolone with N-CH₃, N-CH₃, S$CH_3$ | 138 |
| 665 | — | O | $C_4H_9$-n | (6-) $OCH_3$ | triazolone with N-CH₃, N-CH₃, O$C_2H_5$ | 130 |
| 666 | — | O | $C_4H_9$-n | (6-) $OCH_3$ | triazolone with N-CH₃, N-CH₃, S$CH_3$ | 132 |
| 667 | — | O | $C_3H_7$-i | (6-) $OC_3H_7$-i | triazolone with N-CH₃, N-cyclopropyl, O$C_2H_5$ | 100 |
| 668 | — | O | $C_3H_7$-i | (6-) $OC_3H_7$-i | triazolone with N-CH₃, N-CH₃, S$CH_2C{\equiv}CH$ | 108 |
| 669 | — | O | $C_3H_7$-i | (6-) $OC_3H_7$-i | triazolone with N-CH₃, N-CH₃, $C_3H_7$-n | 130 |

TABLE 1-continued

Examples of the compounds of the formula (I)

| Ex. No. | A | Q | R¹ | (position-) R² | R³ | Melting point (° C.) |
|---|---|---|---|---|---|---|
| 670 | — | O | $C_3H_7$-i | (6-) $OC_3H_7$-i | triazolinone with N-CH₃, N-CH₃, $OC_3H_7$-i | 133 |
| 671 | — | O | $C_3H_7$-i | (6-) $OC_3H_7$-i | triazolinone with N-CH₃, N-CH₃, $CH_2OCH_3$ | 125 |
| 672 | — | O | $C_3H_7$-i | (6-) $OC_3H_7$-i | triazolinone with N-CH₃, N-$C_2H_5$, $OCH_3$ | 108 |
| 673 | — | O | $C_3H_7$-i | (6-) $OC_3H_7$-i | triazolinone with N-CH₃, N-cyclopropyl, $CH_2OCH_3$ | 110 |
| 674 | — | O | $C_4H_9$-n | (6-) $OCH_3$ | triazolinone with N-CH₃, N-CH₃, Br | 144 |
| 675 | — | O | $C_4H_9$-n | (6-) $OCH_3$ | triazolinone with N-CH₃, N-CH₃, $C_2H_5$ | 116 |
| 676 | — | O | $C_4H_9$-n | (6-) $OCH_3$ | triazolinone with N-CH₃, N-CH₃, $OCH_3$ | 139 |
| 677 | — | O | $C_4H_9$-n | (6-) $OCH_3$ | triazolinone with N-CH₃, N-CH₃, $CH_3$ | 174 |

TABLE 1-continued

Examples of the compounds of the formula (I)

| Ex. No. | A | Q | R¹ | (position-) R² | R³ | Melting point (° C.) |
|---|---|---|---|---|---|---|
| 678 | — | O | $C_4H_9$-n | (6-) $OCH_3$ | triazolinone with $CH_3$ and $OCH_2CF_3$ | 149 |
| 679 | — | O | $C_4H_9$-n | (6-) $OCH_3$ | triazolinone with cyclopropyl and Br | 104 |
| 680 | — | O | $C_4H_9$-n | (6-) $OCH_3$ | triazolinone with $CH_3$ and $OC_3H_7$-n | 98 |
| 681 | — | O | $C_4H_9$-n | (6-) $OCH_3$ | triazolinone with cyclopropyl and $OC_2H_5$ | 112 |
| 682 | — | O | $C_4H_9$-n | (6-) $OCH_3$ | triazolinone with $CH_3$ and $SCH_2C\equiv CH$ | 100 |
| 683 | — | O | $C_4H_9$-n | (6-) $OCH_3$ | triazolinone with $CH_3$ and $C_3H_7$-n | 92 |
| 684 | — | O | $C_4H_9$-n | (6-) $OCH_3$ | triazolinone with $CH_3$ and $OC_3H_7$-i | 115 |
| 685 | — | O | $C_4H_9$-n | (6-) $OCH_3$ | triazolinone with $CH_3$ and $CH_2OCH_3$ | 99 |

TABLE 1-continued
Examples of the compounds of the formula (I)
| Ex. No. | A | Q | R¹ | (position-) R² | R³ | Melting point (° C.) |
|---|---|---|---|---|---|---|
| 686 | — | O | $C_4H_9$-n | (6-) $OCH_3$ | 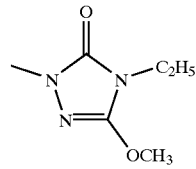 | 102 |
| 687 | — | O | $C_4H_9$-n | (6-) $OCH_3$ | 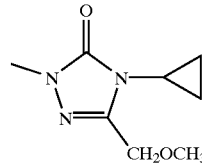 | 106 |
| 688 | — | O | $C_2H_4OC_2H_5$ | (6-) $OCH_3$ | 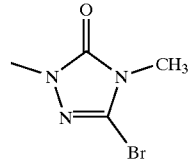 | 120 |
| 689 | — | O | $C_2H_4OC_2H_5$ | (6-) $OCH_3$ | 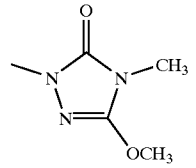 | 98 |
| 690 | — | O | $C_2H_4OC_2H_5$ | (6-) $OCH_3$ | 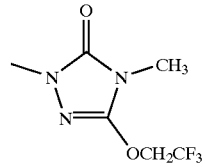 | 138 |
| 691 | — | O | $C_4H_9$-i | (6-) $OC_2H_5$ | 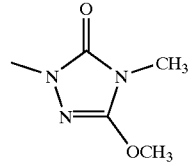 | 118 |
| 692 | — | O | $C_2H_4OC_2H_5$ | (6-) $OCH_3$ | 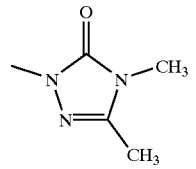 | 138 |
| 693 | — | O | $C_2H_4OC_2H_5$ | (6-) $OCH_3$ | 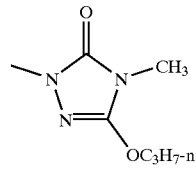 | 94 |

TABLE 1-continued

Examples of the compounds of the formula (I)

| Ex. No. | A | Q | R¹ | (position-) R² | R³ | Melting point (° C.) |
|---|---|---|---|---|---|---|
| 694 | — | O | $C_2H_4OC_2H_5$ | (6-) $OCH_3$ | 1-methyl-4-cyclopropyl-5-ethoxy-1,2,4-triazol-3(4H)-one | 94 |
| 695 | — | O | $C_2H_4OC_2H_5$ | (6-) $OCH_3$ | 1-methyl-4-methyl-5-isopropoxy-1,2,4-triazol-3(4H)-one | 65 |
| 696 | — | O | $C_2H_4OC_2H_5$ | (6-) $OCH_3$ | 1-methyl-4-methyl-5-methoxymethyl-1,2,4-triazol-3(4H)-one | 60 |
| 697 | — | O | $C_2H_4OC_2H_5$ | (6-) $OCH_3$ | 1-methyl-4-ethyl-5-methoxy-1,2,4-triazol-3(4H)-one | 104 |
| 698 | — | O | $C_4H_9$-n | (6-) $OC_4H_9$-n | 1-methyl-4-methyl-5-ethoxy-1,2,4-triazol-3(4H)-one | 104 |
| 699 | — | O | $C_4H_9$-n | (6-) $OC_4H_9$-n | 1-methyl-4-methyl-5-ethyl-1,2,4-triazol-3(4H)-one | 137 |
| 700 | — | O | $C_4H_9$-n | (6-) $OC_4H_9$-n | 1-methyl-4-methyl-5-methylthio-1,2,4-triazol-3(4H)-one | 70 |
| 701 | — | O | $C_4H_9$-n | (6-) $OC_4H_9$-n | 1-methyl-4-methyl-5-bromo-1,2,4-triazol-3(4H)-one | 110 |

TABLE 1-continued

Examples of the compounds of the formula (I)

| Ex. No. | A | Q | R¹ | (position-) R² | R³ | Melting point (° C.) |
|---|---|---|---|---|---|---|
| 702 | — | O | $C_4H_9$-n | (6-) $OC_4H_9$-n | triazolinone with N-CH₃, N-CH₃, OCH₃ | 102 |
| 703 | — | O | $C_3H_7$-i | (6-) $OC_3H_7$-i | triazolinone with N-CH₃, N-cyclopropyl, OCH₃ | 137 |
| 704 | — | O | $C_3H_7$-i | (6-) $OCH_3$ | triazolinone with N-CH₃, N-cyclopropyl, OCH₃ | 160 |
| 705 | — | O | $C_3H_7$-n | (6-) $OC_3H_7$-n | triazolinone with N-CH₃, N-cyclopropyl, OCH₃ | 94 |
| 706 | — | O | $C_3H_7$-n | (6-) $OC_2H_5$ | triazolinone with N-CH₃, N-CH₃, $OC_2H_5$ | 155 |
| 707 | — | O | $C_3H_7$-n | (6-) $OC_2H_5$ | triazolinone with N-CH₃, N-CH₃, $SCH_3$ | 130 |
| 708 | — | O | $C_3H_7$-n | (6-) $OC_2H_5$ | triazolinone with N-CH₃, N-CH₃, Br | 142 |
| 709 | — | O | $C_3H_7$-n | (6-) $OC_2H_5$ | triazolinone with N-CH₃, N-CH₃, $OCH_2CF_3$ | 85 |

TABLE 1-continued

Examples of the compounds of the formula (I)

| Ex. No. | A | Q | R¹ | (position-) R² | R³ | Melting point (° C.) |
|---|---|---|---|---|---|---|
| 710 | — | O | $C_3H_7$-n | (6-) $OC_2H_5$ | 1-methyl-4-methyl-5-(n-propoxy)-1,2,4-triazol-3(4H)-one | 106 |
| 711 | — | O | $C_3H_7$-n | (6-) $OC_2H_5$ | 1-methyl-4-cyclopropyl-5-ethoxy-1,2,4-triazol-3(4H)-one | 87 |
| 712 | — | S | $C_3H_7$-i | (6-) $OCH_3$ | 1-methyl-4-methyl-5-(n-propoxy)-1,2,4-triazol-3(4H)-one | 120 |
| 713 | — | S | $C_4H_9$-n | (6-) $OCH_3$ | 1-methyl-4-cyclopropyl-5-ethoxy-1,2,4-triazol-3(4H)-one | 143 |
| 714 | — | S | $C_3H_7$-i | (6-) $OC_3H_7$-i | 1-methyl-4-cyclopropyl-5-ethoxy-1,2,4-triazol-3(4H)-one | 152 |
| 715 | — | S | $C_2H_4OC_2H_5$ | (6-) $OCH_3$ | 1-methyl-4-cyclopropyl-5-ethoxy-1,2,4-triazol-3(4H)-one | 112 |
| 716 | — | S | $C_3H_7$-i | (6-) $OCH_3$ | 1-methyl-4-cyclopropyl-5-ethoxy-1,2,4-triazol-3(4H)-one | 130 |
| 717 | — | S | $C_3H_7$-i | (6-) $OCH_3$ | 1-methyl-4-methyl-5-methoxy-1,2,4-triazol-3(4H)-one | 165 |

TABLE 1-continued

Examples of the compounds of the formula (I)

| Ex. No. | A | Q | R¹ | (position-) R² | R³ | Melting point (° C.) |
|---|---|---|---|---|---|---|
| 718 | — | S | $C_3H_7$-i | (6-) $OC_3H_7$-i | triazolinone with $N-CH_3$, $N-CH_3$, $OCH_2CF_3$ | 161 |
| 719 | — | S | $C_4H_9$-n | (6-) $OCH_3$ | triazolinone with $N-CH_3$, $N-CH_3$, $OCH_3$ | 111 |
| 720 | — | S | $C_2H_5$ | (6-) $OCH_3$ | triazolinone with $N-CH_3$, $N-CH_3$, $OCH_3$ | 156 |
| 721 | — | S | $C_2H_4OC_2H_5$ | (6-) $OCH_3$ | triazolinone with $N-CH_3$, $N-CH_3$, $OCH_3$ | 137 |
| 722 | — | S | $CH_3$ | (6-) $OCH_3$ | triazolinone with $N-CH_3$, $N-CH_3$, $OC_3H_7$-i | 163 |
| 723 | — | S | $C_3H_7$-n | (6-) $OCH_3$ | triazolinone with $N-CH_3$, $N-CH_3$, $OC_3H_7$-i | 113 |
| 724 | — | S | $C_3H_7$-n | (6-) $OCH_3$ | triazolinone with $N-CH_3$, $N-CH_3$, $OCH_2CF_3$ | 130 |
| 725 | — | S | $C_4H_9$-n | (6-) $OCH_3$ | triazolinone with $N-CH_3$, $N-CH_3$, $OC_3H_7$-i | 154 |

TABLE 1-continued

Examples of the compounds of the formula (I)

| Ex. No. | A | Q | R¹ | (position-) R² | R³ | Melting point (° C.) |
|---|---|---|---|---|---|---|
| 726 | — | S | $C_3H_7$-i | (6-) $OC_3H_7$-i | 1,4-dimethyl-5-(O$C_3H_7$-i)-1,2,4-triazol-3(2H)-one | 157 |
| 727 | — | S | $C_3H_7$-n | (6-) $OC_3H_7$-n | 1,4-dimethyl-5-(O$C_3H_7$-i)-1,2,4-triazol-3(2H)-one | 142 |
| 728 | — | S | $C_2H_5$ | (6-) $OC_2H_5$ | 1,4-dimethyl-5-(O$C_3H_7$-i)-1,2,4-triazol-3(2H)-one | 162 |
| 729 | — | S | $CH_3$ | (6-) $OCH_3$ | 1,4-dimethyl-5-(O$CH_2CF_3$)-1,2,4-triazol-3(2H)-one | 157 |
| 730 | — | S | $C_2H_5$ | (6-) $OCH_3$ | 1,4-dimethyl-5-(O$CH_2CF_3$)-1,2,4-triazol-3(2H)-one | 108 |
| 731 | — | S | $CH_3$ | (6-) $OCH_3$ | 1-methyl-4-cyclopropyl-5-(O$C_2H_5$)-1,2,4-triazol-3(2H)-one | 172 |
| 732 | — | S | $CH_3$ | (6-) $OCH_3$ | 1,4-dimethyl-5-(S$CH_3$)-1,2,4-triazol-3(2H)-one | 147 |
| 733 | — | S | $C_3H_7$-n | (6-) $OC_3H_7$-n | 1-methyl-4-cyclopropyl-5-(O$C_2H_5$)-1,2,4-triazol-3(2H)-one | 160 |

TABLE 1-continued
Examples of the compounds of the formula (I)
| Ex. No. | A | Q | R¹ | (position-) R² | R³ | Melting point (° C.) |
|---|---|---|---|---|---|---|
| 734 | — | S | $C_3H_7$-n | (6-) $OC_3H_7$-n | 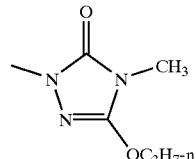 | 103 |
| 735 | — | O | $C_3H_7$-n | (6-) $OC_3H_7$-n | 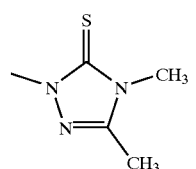 | 172 |
| 736 | — | S | $C_2H_5$ | (6-) $OC_2H_5$ | 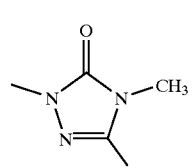 | 137 |
| 737 | — | S | $C_2H_5$ | (6-) $OC_2H_5$ | 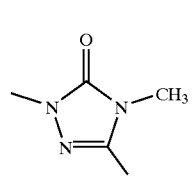 | 156 |
| 738 | — | S | $C_2H_4OC_2H_5$ | (6-) $OCH_3$ | 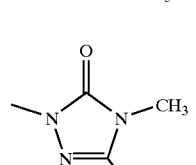 | 103 |
| 739 | — | S | $C_3H_7$-i | (6-) $OC_3H_7$-i | 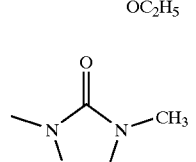 | 134 |
| 740 | — | S | $C_4H_9$-n | (6-) $OC_4H_9$-n | 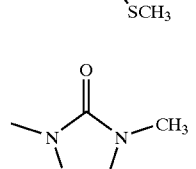 | 87 |
| 741 | — | S | $C_4H_9$-n | (6-) $OC_4H_9$-n | 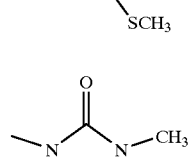 | 110 |

TABLE 1-continued

Examples of the compounds of the formula (I)

| Ex. No. | A | Q | R$^1$ | (position-) R$^2$ | R$^3$ | Melting point (° C.) |
|---|---|---|---|---|---|---|
| 742 | — | S | C$_4$H$_9$-n | (6-) OC$_4$H$_9$-n | 1,2,4-triazol-3(2H)-one, 2-methyl, 4-CH$_3$, 5-OC$_2$H$_5$ | 88 |
| 743 | — | S | C$_4$H$_9$-n | (6-) OC$_4$H$_9$-n | 1,2,4-triazol-3(2H)-one, 2-methyl, 4-cyclopropyl, 5-OC$_2$H$_5$ | 98 |
| 744 | — | S | C$_4$H$_9$-n | (6-) OC$_4$H$_9$-n | 1,2,4-triazol-3(2H)-one, 2-methyl, 4-CH$_3$, 5-OC$_3$H$_7$-n | 98 |
| 745 | — | S | C$_4$H$_9$-n | (6-) OC$_4$H$_9$-n | 1,2,4-triazol-3(2H)-one, 2-methyl, 4-CH$_3$, 5-SCH$_3$ | 88 |
| 746 | — | S | C$_4$H$_9$-n | (6-) OC$_4$H$_9$-n | 1,2,4-triazol-3(2H)-one, 2-methyl, 4-CH$_3$, 5-OCH$_2$CF$_3$ | 104 |
| 747 | — | S | C$_4$H$_9$-n | (6-) OC$_4$H$_9$-n | 1,2,4-triazol-3(2H)-one, 2-methyl, 4-CH$_3$, 5-OC$_3$H$_7$-i | 75 |
| 748 | — | O | C$_2$H$_5$ | (6-) OC$_2$H$_5$ | 1,3,4-oxadiazole, 2-methyl, 5-CH$_3$ | 145 |
| 749 | — | S | C$_3$H$_7$-i | (6-) OC$_2$H$_5$ | 1,2,4-triazol-3(2H)-one, 2-methyl, 4-CH$_3$, 5-SCH$_3$ | 131 |

TABLE 1-continued

Examples of the compounds of the formula (I)

| Ex. No. | A | Q | R¹ | (position-) R² | R³ | Melting point (° C.) |
|---|---|---|---|---|---|---|
| 750 | — | S | $C_3H_7$-i | (6-) $OC_2H_5$ | 1,2,4-triazol-3(2H)-one, 2-methyl, 4-methyl, 5-OCH₃ | 158 |
| 751 | — | S | $C_3H_7$-i | (6-) $OC_2H_5$ | 1,2,4-triazol-3(2H)-one, 2-methyl, 4-methyl, 5-OC₃H₇-n | 132 |
| 752 | — | S | $C_3H_7$-i | (6-) $OC_2H_5$ | 1,2,4-triazol-3(2H)-one, 2-methyl, 4-cyclopropyl, 5-OC₂H₅ | 142 |
| 753 | — | S | $C_3H_7$-i | (6-) $OC_2H_5$ | 1,2,4-triazol-3(2H)-one, 2-methyl, 4-methyl, 5-C₂H₅ | 130 |
| 754 | — | S | $C_3H_7$-i | (6-) $OC_2H_5$ | 1,2,4-triazol-3(2H)-one, 2-methyl, 4-methyl, 5-OC₃H₇-i | 170 |
| 755 | — | S | $C_3H_7$-n | (6-) $OC_2H_5$ | 1,2,4-triazol-3(2H)-one, 2-methyl, 4-methyl, 5-OCH₃ | 152 |
| 756 | — | S | $C_3H_7$-n | (6-) $OC_2H_5$ | 1,2,4-triazol-3(2H)-one, 2-methyl, 4-methyl, 5-SCH₃ | 138 |
| 757 | — | S | $C_3H_7$-n | (6-) $OC_2H_5$ | 1,2,4-triazol-3(2H)-one, 2-methyl, 4-methyl, 5-C₂H₅ | 130 |

TABLE 1-continued

Examples of the compounds of the formula (I)

| Ex. No. | A | Q | R¹ | (position-) R² | R³ | Melting point (° C.) |
|---|---|---|---|---|---|---|
| 758 | — | S | $C_3H_7$-n | (6-) $OC_2H_5$ | 1-methyl-4-methyl-5-(OCH₂CF₃)-1,2,4-triazol-3(4H)-one | 150 |
| 759 | — | S | $C_3H_7$-n | (6-) $OC_2H_5$ | 1-methyl-4-cyclopropyl-5-($OC_2H_5$)-1,2,4-triazol-3(4H)-one | 156 |
| 760 | — | S | $C_3H_7$-n | (6-) $OC_2H_5$ | 1-methyl-4-methyl-5-($SC_2H_5$)-1,2,4-triazol-3(4H)-one | 110 |
| 761 | — | S | $C_3H_7$-n | (6-) $OC_2H_5$ | 1-methyl-4-methyl-5-$CH_3$-1,2,4-triazol-3(4H)-one | 120 |
| 762 | — | S | $C_4H_9$-n | (6-) $OC_4H_9$-n | 1-methyl-4-methyl-5-($SC_2H_5$)-1,2,4-triazol-3(4H)-one | 104 |
| 763 | — | S | $C_3H_7$-i | (6-) $OCH_3$ | 1-methyl-4-methyl-5-($SC_2H_5$)-1,2,4-triazol-3(4H)-one | 105 |
| 764 | — | S | $C_3H_7$-n | (6-) $OC_3H_7$-n | 1-methyl-4-methyl-5-($SC_2H_5$)-1,2,4-triazol-3(4H)-one | 120 |
| 765 | — | S | $C_3H_7$-n | (6-) $OCH_3$ | 1-methyl-4-methyl-5-($SC_2H_5$)-1,2,4-triazol-3(4H)-one | 135 |

TABLE 1-continued
Examples of the compounds of the formula (I)
| Ex. No. | A | Q | R¹ | (position-) R² | R³ | Melting point (° C.) |
|---|---|---|---|---|---|---|
| 766 | — | S | $C_3H_7$-n | (6-) $OC_3H_7$-n | 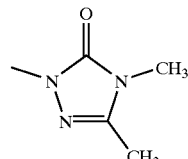 | 116 |
| 767 | — | S | $C_3H_7$-i | (6-) $OC_3H_7$-i | 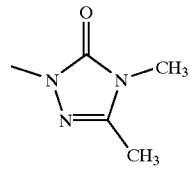 | 110 |
| 768 | — | S | $C_2H_4OC_2H_5$ | (6-) $OCH_3$ | 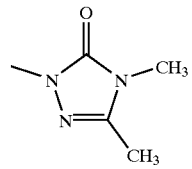 | 95 |
| 769 | — | S | $C_3H_7$-i | (6-) $OCH_3$ | 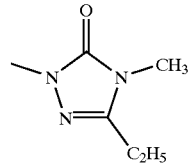 | 112 |
| 770 | — | O | $C_3H_7$-i | (6-) $OC_2H_5$ | 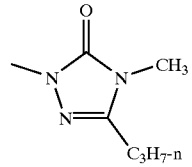 | 70 |
| 771 | — | O | $C_3H_7$-i | (6-) $OC_2H_5$ | 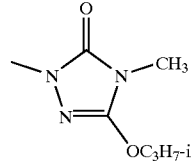 | 132 |
| 772 | — | O | $C_3H_7$-i | (6-) $OC_2H_5$ | 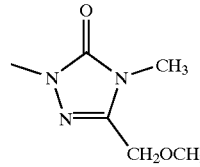 | 75 |
| 773 | — | O | $C_3H_7$-i | (6-) $OC_2H_5$ | 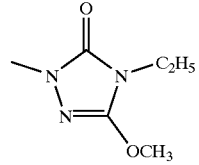 | 118 |

TABLE 1-continued

Examples of the compounds of the formula (I)

| Ex. No. | A | Q | R¹ | (position-) R² | R³ | Melting point (° C.) |
|---|---|---|---|---|---|---|
| 774 | — | O | $C_3H_7$-i | (6-) $OC_2H_5$ | ![structure: 1-methyl-4-cyclopropyl-5-(CH2OCH3)-1,2,4-triazol-3(4H)-one] | 85 |
| 775 | — | O | $C_3H_7$-i | (6-) $OC_2H_5$ | ![structure: 1-methyl-4-methyl-5-Br-1,2,4-triazol-3(4H)-one] | 130 |
| 776 | — | O | $C_3H_7$-i | (6-) $OC_2H_5$ | ![structure: 1-methyl-4-methyl-5-OCH3-1,2,4-triazol-3(4H)-one] | 120 |
| 777 | — | O | $C_3H_7$-i | (6-) $OC_2H_5$ | ![structure: 1-methyl-4-methyl-5-OCH2CF3-1,2,4-triazol-3(4H)-one] | 124 |
| 778 | — | O | $C_3H_7$-i | (6-) $OC_2H_5$ | ![structure: 1-methyl-4-methyl-5-OC3H7-n-1,2,4-triazol-3(4H)-one] | 130 |
| 779 | — | O | $C_3H_7$-i | (6-) $OC_2H_5$ | ![structure: 1-methyl-4-cyclopropyl-5-OC2H5-1,2,4-triazol-3(4H)-one] | 100 |
| 780 | — | O | $C_2H_5$ | (6-) $OCH_3$ | ![structure: 1-methyl-4-cyclopropyl-5-OCH3-1,2,4-triazol-3(4H)-one] | 172 |
| 781 | — | O | $C_2H_5$ | (6-) $OCH_3$ | ![structure: 1-methyl-4-cyclopropyl-5-OC3H7-i-1,2,4-triazol-3(4H)-one] | 164 |

TABLE 1-continued

Examples of the compounds of the formula (I)

| Ex. No. | A | Q | R¹ | (position-) R² | R³ | Melting point (° C.) |
|---|---|---|---|---|---|---|
| 782 | — | O | $C_3H_7$-i | (6-) $OC_3H_7$-i | triazolinone with N-CH₃, N-cyclopropyl, $OC_3H_7$-i | 118 |
| 783 | — | O | $C_3H_7$-i | (6-) $OC_3H_7$-i | triazolinone with N-CH₃, N-cyclopropyl, $OC_3H_7$-n | 88 |
| 784 | — | O | $C_4H_9$-s | (6-) $OCH_3$ | triazolinone with N-CH₃, N-CH₃, $OC_2H_5$ | 124 |
| 785 | — | O | $C_4H_9$-s | (6-) $OCH_3$ | triazolinone with N-CH₃, N-CH₃, $C_2H_5$ | 100 |
| 786 | — | O | $C_4H_9$-n | (6-) $OC_2H_5$ | triazolinone with N-CH₃, N-CH₃, $OC_2H_5$ | 106 |
| 787 | — | O | $C_4H_9$-n | (6-) $OC_2H_5$ | triazolinone with N-CH₃, N-CH₃, $SCH_3$ | 108 |
| 788 | — | O | $C_4H_9$-n | (6-) $OC_2H_5$ | triazolinone with N-CH₃, N-CH₃, $C_2H_5$ | 105 |
| 789 | — | O | $C_4H_9$-s | (6-) $OCH_3$ | triazolinone with N-CH₃, N-cyclopropyl, $OCH_3$ | 112 |

TABLE 1-continued
Examples of the compounds of the formula (I)
| Ex. No. | A | Q | R¹ | (position-) R² | R³ | Melting point (° C.) |
|---|---|---|---|---|---|---|
| 790 | — | O | C₄H₉-n | (6-) OC₂H₅ | 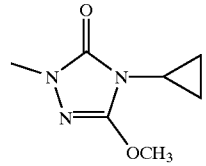 | 80 |
| 791 | — | O | C₄H₉-s | (6-) OCH₃ | 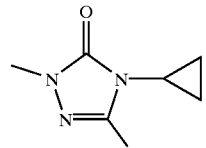 | 130 |
| 792 | — | O | C₄H₉-n | (6-) OC₂H₅ | 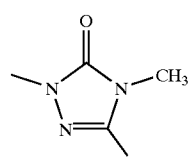 | 120 |
| 793 | — | O | C₄H₉-n | (6-) OC₂H₅ | 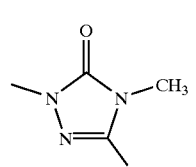 | 95 |
| 794 | — | O | C₄H₉-n | (6-) OC₂H₅ | 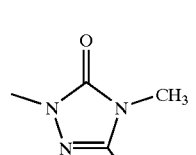 | 96 |
| 795 | — | O | C₄H₉-s | (6-) OCH₃ | 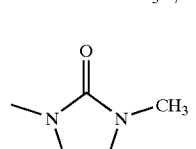 | 130 |
| 796 | — | O | C₄H₉-s | (6-) OCH₃ | 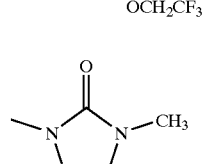 | 118 |
| 797 | — | O | C₄H₉-s | (6-) OCH₃ | 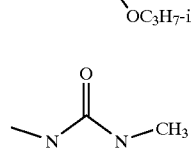 | 134 |

TABLE 1-continued

Examples of the compounds of the formula (I)

| Ex. No. | A | Q | R¹ | (position-) R² | R³ | Melting point (° C.) |
|---|---|---|---|---|---|---|
| 798 | — | O | $C_4H_9$-s | (6-) $OCH_3$ | N-methyl, N'-methyl triazolone with $OCH_3$ | 118 |
| 799 | — | O | $C_4H_9$-n | (6-) $OC_2H_5$ | N-methyl, N'-cyclopropyl triazolone with $OC_2H_5$ | 90 |
| 800 | — | O | $C_4H_9$-s | (6-) $OCH_3$ | N-methyl, N'-methyl triazolone with $OC_3H_7$-n | 78 |
| 801 | — | O | $C_4H_9$-s | (6-) $OCH_3$ | N-methyl, N'-cyclopropyl triazolone with $OC_2H_5$ | 112 |
| 802 | — | O | $C_4H_9$-s | (6-) $OCH_3$ | N-methyl, N'-methyl triazolone with $CH_2OCH_3$ | 78 |
| 803 | — | O | $C_4H_9$-s | (6-) $OCH_3$ | N-methyl, N'-ethyl triazolone with $OCH_3$ | 80 |
| 804 | — | O | $C_4H_9$-n | (6-) $OC_4H_9$-n | N-methyl, N'-methyl triazolone with $OC_3H_7$-n | 55 |
| 805 | — | O | $C_4H_9$-n | (6-) $OC_4H_9$-n | N-methyl, N'-cyclopropyl triazolone with $OC_2H_5$ | 100 |

TABLE 1-continued

Examples of the compounds of the formula (I)

| Ex. No. | A | Q | R¹ | (position-) R² | R³ | Melting point (° C.) |
|---|---|---|---|---|---|---|
| 806 | — | O | $C_4H_9$-n | (6-) $OC_4H_9$-n | 1-methyl-4-ethyl-5-methoxy-1,2,4-triazol-3(4H)-one | 92 |
| 807 | — | O | $C_3H_7$-n | (6-) $OC_2H_5$ | 1-methyl-4-methyl-5-(n-propyl)-1,2,4-triazol-3(4H)-one | 74 |
| 808 | — | O | $C_3H_7$-n | (6-) $OC_2H_5$ | 1-methyl-4-methyl-5-(i-propoxy)-1,2,4-triazol-3(4H)-one | 143 |
| 809 | — | O | $C_3H_7$-n | (6-) $OC_2H_5$ | 1-methyl-4-methyl-5-($CH_2OCH_3$)-1,2,4-triazol-3(4H)-one | 102 |
| 810 | — | O | $C_3H_7$-n | (6-) $OC_2H_5$ | 1-methyl-4-ethyl-5-methoxy-1,2,4-triazol-3(4H)-one | 95 |
| 811 | — | O | $C_4H_9$-n | (6-) $OC_4H_9$-n | 1-methyl-4-methyl-5-(i-propoxy)-1,2,4-triazol-3(4H)-one | 82 |
| 812 | — | O | $C_4H_9$-n | (6-) $OC_2H_5$ | 1-methyl-4-cyclopropyl-5-(i-propoxy)-1,2,4-triazol-3(4H)-one | 92 |
| 813 | — | O | $C_4H_9$-n | (6-) $OCH_3$ | 1-methyl-4-cyclopropyl-5-(i-propoxy)-1,2,4-triazol-3(4H)-one | 90 |

TABLE 1-continued

Examples of the compounds of the formula (I)

| Ex. No. | A | Q | R¹ | (position-) R² | R³ | Melting point (° C.) |
|---|---|---|---|---|---|---|
| 814 | — | O | $C_4H_9$-n | (6-) $OCH_3$ | triazolinone with cyclopropyl and $OCH_3$ | 124 |
| 815 | — | O | $C_4H_9$-n | (6-) $OCH_3$ | triazolinone with cyclopropyl and $OC_3H_7$-n | 85 |
| 816 | — | O | $C_4H_9$-n | (6-) $OCH_3$ | triazolinone with cyclopropyl and $OCH_2CF_3$ | 90 |
| 817 | — | O | $C_2H_4OC_2H_5$ | (6-) $OCH_3$ | triazolinone with cyclopropyl and $OCH_3$ | 90 |
| 818 | — | O | cyclopentyl | (6-) $OCH_3$ | triazolinone with $CH_3$ and $OC_2H_5$ | 165 |
| 819 | — | O | cyclopentyl | (6-) $OCH_3$ | triazolinone with $CH_3$ and $SCH_3$ | 130 |
| 820 | — | O | cyclopentyl | (6-) $OCH_3$ | triazolinone with $CH_3$ and $OCH_3$ | 149 |
| 821 | — | O | $C_4H_9$-s | (6-) $OC_4H_9$-s | triazolinone with $CH_3$ and $OC_2H_5$ | 125 |

TABLE 1-continued
Examples of the compounds of the formula (I)
| Ex. No. | A | Q | R¹ | (position-) R² | R³ | Melting point (° C.) |
|---|---|---|---|---|---|---|
| 822 | — | O | 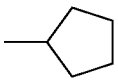 | (6-) OCH₃ | 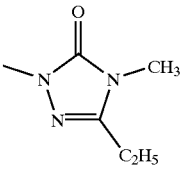 | 112 |
| 823 | — | O | 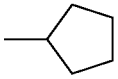 | (6-) OCH₃ | 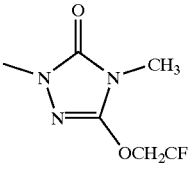 | 156 |
| 824 | — | O | 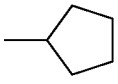 | (6-) OCH₃ | 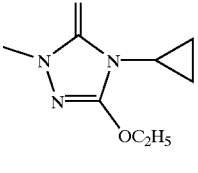 | 148 |
| 825 | — | O | 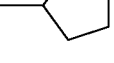 | (6-) OCH₃ | 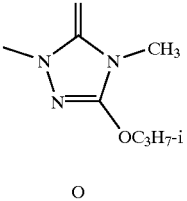 | 145 |
| 826 | — | O | 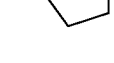 | (6-) OCH₃ | 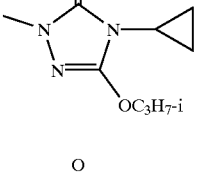 | 156 |
| 827 | — | O | 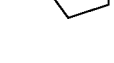 | (6-) OCH₃ | 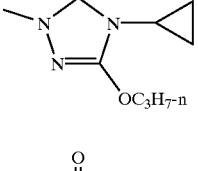 | 126 |
| 828 | — | O | 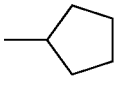 | (6-) OCH₃ | 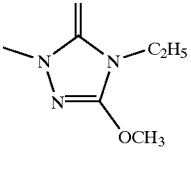 | 134 |
| 829 | — | O | 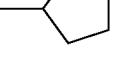 | (6-) OCH₃ | 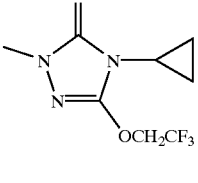 | 114 |

TABLE 1-continued

Examples of the compounds of the formula (I)

| Ex. No. | A | Q | R¹ | (position-) R² | R³ | Melting point (° C.) |
|---|---|---|---|---|---|---|
| 830 | — | O | cyclopentylmethyl | (6-) OCH₃ | 4-cyclopropyl-2-methyl-5-methoxy-2,4-dihydro-3H-1,2,4-triazol-3-one | 141 |
| 831 | — | O | $C_4H_9$-i | (6-) $OC_2H_5$ | 4-methyl-2-methyl-5-ethoxy-2,4-dihydro-3H-1,2,4-triazol-3-one | 125 |
| 832 | — | O | $C_4H_9$-i | (6-) $OC_2H_5$ | 4-methyl-2-methyl-5-methylthio-2,4-dihydro-3H-1,2,4-triazol-3-one | 128 |
| 833 | — | O | $C_4H_9$-i | (6-) $OC_2H_5$ | 4-cyclopropyl-2-methyl-5-methoxy-2,4-dihydro-3H-1,2,4-triazol-3-one | 106 |
| 834 | — | O | $C_4H_9$-i | (6-) $OC_2H_5$ | 4-methyl-2-methyl-5-n-propoxy-2,4-dihydro-3H-1,2,4-triazol-3-one | 88 |
| 835 | — | O | $C_4H_9$-i | (6-) $OC_2H_5$ | 4-cyclopropyl-2-methyl-5-ethoxy-2,4-dihydro-3H-1,2,4-triazol-3-one | 112 |
| 836 | — | O | $C_4H_9$-i | (6-) $OC_2H_5$ | 4-methyl-2-methyl-5-isopropoxy-2,4-dihydro-3H-1,2,4-triazol-3-one | 125 |
| 837 | — | O | $C_4H_9$-i | (6-) $OC_2H_5$ | 4-methyl-2-methyl-5-(2,2,2-trifluoroethoxy)-2,4-dihydro-3H-1,2,4-triazol-3-one | 106 |

TABLE 1-continued

Examples of the compounds of the formula (I)

| Ex. No. | A | Q | R¹ | (position-) R² | R³ | Melting point (° C.) |
|---|---|---|---|---|---|---|
| 838 | — | O | H | (6-) OH | 1,2,4-triazol-3(2H)-one, 2-CH₃, 4-CH₃, 5-OC₂H₅ | 172 |
| 839 | — | O | C₄H₉-i | (6-) OCH₃ | 1,2,4-triazol-3(2H)-one, 2-CH₃, 4-CH₃, 5-OC₂H₅ | 102 |
| 840 | — | O | C₄H₉-i | (6-) OCH₃ | 1,2,4-triazol-3(2H)-one, 2-CH₃, 4-CH₃, 5-SCH₃ | 114 |
| 841 | — | O | C₄H₉-i | (6-) OCH₃ | 1,2,4-triazol-3(2H)-one, 2-CH₃, 4-CH₃, 5-OCH₃ | 124 |
| 842 | — | O | C₄H₉-i | (6-) OCH₃ | 1,2,4-triazol-3(2H)-one, 2-CH₃, 4-CH₃, 5-OC₃H₇-n | 98 |
| 843 | — | O | C₄H₉-i | (6-) OCH₃ | 1,2,4-triazol-3(2H)-one, 2-CH₃, 4-cyclopropyl, 5-OC₂H₅ | 146 |
| 844 | — | O | C₄H₉-i | (6-) OCH₃ | 1,2,4-triazol-3(2H)-one, 2-CH₃, 4-cyclopropyl, 5-OCH₃ | 97 |
| 845 | — | O | C₄H₉-i | (6-) OCH₃ | 1,2,4-triazol-3(2H)-one, 2-CH₃, 4-CH₃, 5-OC₃H₇-i | 117 |

TABLE 1-continued

Examples of the compounds of the formula (I)

| Ex. No. | A | Q | R¹ | (position-) R² | R³ | Melting point (° C.) |
|---|---|---|---|---|---|---|
| 846 | — | O | $C_4H_9$-i | (6-) $OCH_3$ | (1-methyl-4-cyclopropyl-5-(i-propoxy)-1,2,4-triazol-3(4H)-one) | 142 |
| 847 | — | O | $C_4H_9$-i | (6-) $OCH_3$ | (1-methyl-4-cyclopropyl-5-(n-propoxy)-1,2,4-triazol-3(4H)-one) | 109 |
| 848 | — | S | $C_2H_5$ | (6-) $OCH_3$ | (1,4-dimethyl-5-(ethylthio)-1,2,4-triazol-3(4H)-one) | 138 |
| 849 | — | S | $C_2H_5$ | (6-) $OCH_3$ | (1-methyl-4-cyclopropyl-5-ethoxy-1,2,4-triazol-3(4H)-one) | 135 |
| 850 | — | S | $C_2H_5$ | (6-) $OCH_3$ | (1,4,5-trimethyl-1,2,4-triazol-3(4H)-one) | 155 |
| 851 | — | S | $C_2H_5$ | (6-) $OCH_3$ | (1,4-dimethyl-5-(i-propoxy)-1,2,4-triazol-3(4H)-one) | 160 |
| 852 | — | S | $C_4H_9$-s | (6-) $OCH_3$ | (1,4,5-trimethyl-1,2,4-triazol-3(4H)-one) | 108 |
| 853 | — | S | $C_4H_9$-s | (6-) $OCH_3$ | (1,4-dimethyl-5-(methylthio)-1,2,4-triazol-3(4H)-one) | 143 |

TABLE 1-continued

Examples of the compounds of the formula (I)

| Ex. No. | A | Q | R¹ | (position-) R² | R³ | Melting point (° C.) |
|---|---|---|---|---|---|---|
| 854 | — | S | $C_4H_9$-s | (6-) $OCH_3$ | triazolinone with $CH_3$, $CH_3$, $OC_3H_7$-n | 105 |
| 855 | — | S | $C_4H_9$-s | (6-) $OCH_3$ | triazolinone with $CH_3$, $CH_3$, $SC_2H_5$ | 65 |
| 856 | — | S | $C_4H_9$-s | (6-) $OCH_3$ | triazolinone with $CH_3$, $CH_3$, $OCH_2CF_3$ | 114 |
| 857 | — | O | $C_2H_5$ | (3-) $CH_3$ | triazolinone with $CH_3$, $CH_3$, $OC_2H_5$ | 179 |
| 858 | — | S | $C_4H_9$-s | (6-) $OCH_3$ | triazolinone with $CH_3$, cyclopropyl, $OC_2H_5$ | 146 |
| 859 | — | S | $C_3H_7$-i | (6-) $OCH_3$ | triazolinone with $CH_3$, $CH_3$, $SCH_3$ | 146 |
| 860 | — | S | $C_4H_9$-n | (6-) $OCH_3$ | triazolinone with $CH_3$, $CH_3$, $C_2H_5$ | 132 |
| 861 | — | S | $C_4H_9$-n | (6-) $OCH_3$ | triazolinone with $CH_3$, $CH_3$, $OCH_2CF_3$ | 112 |

TABLE 1-continued

Examples of the compounds of the formula (I)

| Ex. No. | A | Q | R¹ | (position-) R² | R³ | Melting point (° C.) |
|---|---|---|---|---|---|---|
| 862 | — | S | $C_4H_9$-n | (6-) $OCH_3$ | (1-methyl-4-methyl-5-(n-propoxy)-1,2,4-triazol-3(4H)-one) | 100 |
| 863 | — | S | $C_4H_9$-n | (6-) $OCH_3$ | (1-methyl-4-cyclopropyl-5-methoxy-1,2,4-triazol-3(4H)-one) | 138 |
| 864 | — | S | $C_3H_7$-i | (6-) $OC_2H_5$ | (1-methyl-4-methyl-5-ethoxy-1,2,4-triazol-3(4H)-one) | 155 |
| 865 | — | S | $C_3H_7$-i | (6-) $OC_2H_5$ | (1-methyl-4-cyclopropyl-5-methoxy-1,2,4-triazol-3(4H)-one) | 140 |
| 866 | — | S | $C_4H_9$-n | (6-) $OCH_3$ | (1-methyl-4-methyl-5-ethoxy-1,2,4-triazol-3(4H)-one) | 140 |
| 867 | — | O | $C_4H_9$-i | (6-) $OCH_3$ | (1-methyl-4-ethyl-5-methoxy-1,2,4-triazol-3(4H)-one) | 131 |
| 868 | — | O | $C_4H_9$-i | (6-) $OCH_3$ | (1-methyl-4-cyclopropyl-5-(i-propoxy)-1,2,4-triazol-3(4H)-one) | 135 |
| 869 | — | O | $C_4H_9$-i | (6-) $OCH_3$ | (1-methyl-4-cyclopropyl-5-(n-propoxy)-1,2,4-triazol-3(4H)-one) | 137 |

TABLE 1-continued

Examples of the compounds of the formula (I)

| Ex. No. | A | Q | R¹ | (position-) R² | R³ | Melting point (° C.) |
|---|---|---|---|---|---|---|
| 870 | — | O | $C_4H_9$-n | (6-) $OC_4H_9$-n | 1,4-dimethyl-5-methyl-1,2,4-triazol-3(2H)-one | 123 |
| 871 | — | O | $C_4H_9$-n | (6-) $OC_2H_5$ | 1,4-dimethyl-5-methyl-1,2,4-triazol-3(2H)-one | 118 |
| 872 | — | O | cyclopentylmethyl | (6-) $OCH_3$ | 1,4-dimethyl-5-methyl-1,2,4-triazol-3(2H)-one | 164 |
| 873 | — | O | $C_3H_7$-i | (6-) $OCH_3$ | 4-cyclopropyl-5-ethylthio-1-methyl-1,2,4-triazol-3(2H)-one | 150 |
| 874 | — | O | $C_3H_7$-i | (6-) $OC_3H_7$-i | 4-cyclopropyl-5-ethylthio-1-methyl-1,2,4-triazol-3(2H)-one | 148 |
| 875 | — | O | $C_3H_7$-n | (6-) $OCH_3$ | 4-cyclopropyl-5-ethylthio-1-methyl-1,2,4-triazol-3(2H)-one | 147 |
| 876 | — | O | $C_2H_5$ | (6-) $OC_2H_5$ | 4-cyclopropyl-5-ethylthio-1-methyl-1,2,4-triazol-3(2H)-one | 108 |
| 877 | — | O | $C_3H_7$-i | (6-) $OC_3H_7$-i | 4-methyl-5-ethylthio-1-methyl-1,2,4-triazol-3(2H)-one | 108 |

TABLE 1-continued

Examples of the compounds of the formula (I)

| Ex. No. | A | Q | R¹ | (position-) R² | R³ | Melting point (° C.) |
|---|---|---|---|---|---|---|
| 878 | — | O | $C_3H_7$-i | (6-) $OC_3H_7$-i | [triazolinone with N-CH₃, N-cyclopropyl, C₂H₅] | 148 |
| 879 | — | O | $C_2H_5$ | (6-) $OC_2H_5$ | [triazolinone with N-CH₃, N-cyclopropyl, CH₃] | 176 |
| 880 | — | O | $C_3H_7$-n | (6-) $OCH_3$ | [triazolinone with N-CH₃, N-cyclopropyl, CH₃] | 144 |
| 881 | — | O | $C_3H_7$-i | (6-) $OC_3H_7$-i | [triazolinone with N-CH₃, N-cyclopropyl, CH₃] | 167 |
| 882 | — | O | $C_2H_5$ | (6-) $OC_2H_5$ | [triazolinone with N-CH₃, N-cyclopropyl, cyclopropyl] | 135 |
| 883 | — | O | $C_3H_7$-n | (6-) $OCH_3$ | [triazolinone with N-CH₃, N-cyclopropyl, cyclopropyl] | 100 |
| 884 | — | O | $C_2H_5$ | (6-) $OC_2H_5$ | [triazolinone with N-CH₃, N-cyclopropyl, $SCH_3$] | 158 |

TABLE 1-continued

Examples of the compounds of the formula (I)

| Ex. No. | A | Q | R$^1$ | (position-) R$^2$ | R$^3$ | Melting point (° C.) |
|---|---|---|---|---|---|---|
| 885 | — | O | C$_3$H$_7$-n | (6-) OCH$_3$ | 1-methyl-4-(cyclopropylmethyl)-5-cyclopropyl-1,2,4-triazol-3(4H)-one | 108 |
| 886 | — | O | C$_3$H$_7$-i | (6-) OC$_3$H$_7$-i | 1-methyl-4-(cyclopropylmethyl)-5-cyclopropyl-1,2,4-triazol-3(4H)-one | 164 |
| 887 | — | O | C$_3$H$_7$-i | (6-) OC$_3$H$_7$-i | 1-methyl-4-(cyclopropylmethyl)-5-ethyl-1,2,4-triazol-3(4H)-one | 157 |
| 888 | — | O | C$_3$H$_7$-n | (6-) OCH$_3$ | 1-methyl-4-(cyclopropylmethyl)-5-(n-propyl)-1,2,4-triazol-3(4H)-one | 113 |
| 889 | — | O | C$_3$H$_7$-i | (6-) OC$_3$H$_7$-i | 1-methyl-4-(cyclopropylmethyl)-5-(n-propyl)-1,2,4-triazol-3(4H)-one | 132 |
| 890 | — | O | C$_3$H$_7$-n | (6-) OCH$_3$ | 1-methyl-4-(cyclopropylmethyl)-5-ethyl-1,2,4-triazol-3(4H)-one | 92 |
| 891 | — | O | C$_3$H$_7$-i | (6-) OC$_3$H$_7$-i | 1-methyl-4-methyl-5-(i-butyl)-1,2,4-triazol-3(4H)-one | 141 |
| 892 | — | O | C$_3$H$_7$-i | (6-) OC$_3$H$_7$-i | 1-methyl-4-cyclopropyl-5-(methylthio)-1,2,4-triazol-3(4H)-one | 159 |

TABLE 1-continued

Examples of the compounds of the formula (I)

| Ex. No. | A | Q | R¹ | (position-) R² | R³ | Melting point (° C.) |
|---|---|---|---|---|---|---|
| 893 | — | O | $C_2H_5$ | (6-) $OC_2H_5$ | 1,2,4-triazol-3(2H)-one, 2-CH₃, 4-CH₃, 5-$SC_2H_5$ | 139 |
| 894 | — | O | $C_2H_5$ | (6-) $OC_2H_5$ | 1,2,4-triazol-3(2H)-one, 2-CH₃, 4-cyclopropyl, 5-$C_2H_5$ | 150 |
| 895 | — | O | $C_3H_7$-n | (6-) $OCH_3$ | 1,2,4-triazol-3(2H)-one, 2-CH₃, 4-cyclopropyl, 5-$C_2H_5$ | 126 |
| 896 | — | O | $C_3H_7$-i | (6-) $CH_3$ | 1,2,4-triazol-3(2H)-one, 2-CH₃, 4-cyclopropyl, 5-O—CH₂-cyclopropyl | 148 |
| 897 | — | O | $C_3H_7$-i | (6-) $CH_3$ | 1,2,4-triazol-3(2H)-one, 2-CH₃, 4-CH₃, 5-O—CH₂-cyclopropyl | 157 |
| 898 | — | O | $C_3H_7$-i | (6-) $CH_3$ | 1,2,4-triazol-3(2H)-one, 2-CH₃, 4-cyclopropyl, 5-$OCH_2CH=CH_2$ | 125 |
| 899 | NH | O | $CH_3$ | (6-) $OCH_3$ | 1,2,4-triazol-3(2H)-one, 2-CH₃, 4-CH₃, 5-$OC_2H_5$ | 182 |
| 900 | NH | O | $CH_3$ | (6-) $OCH_3$ | 1,2,4-triazol-3(2H)-one, 2-CH₃, 4-CH₃, 5-$SCH_3$ | 175 |

TABLE 1-continued

Examples of the compounds of the formula (I)

| Ex. No. | A | Q | R¹ | (position-) R² | R³ | Melting point (° C.) |
|---|---|---|---|---|---|---|
| 901 | — | O | CF₃ | (6-) CH₃ | ![triazolinone with N-CH₃, N-CH₃, OCH₃] | 198 (Na salt) |
| 902 | — | O | CF₃ | (6-) CH₃ | ![triazolinone with N-CH₃, N-CH₃, OC₃H₇-n] | 129 |
| 903 | — | O | CF₃ | (6-) CH₃ | ![triazolinone with N-CH₃, N-CH₃, OC₂H₅] | 149 |
| 904 | — | O | CF₃ | (6-) CH₃ | ![triazolinone with N-CH₃, N-cyclopropyl, OC₃H₇-i] | 163 |
| 905 | — | O | CF₃ | (6-) C₂H₅ | ![triazolinone with N-CH₃, N-CH₃, OCH₃] | 121 |
| 906 | — | O | C₃H₇-i | (6-) CH₃ | ![triazolinone with N-CH₃, N-cyclopropyl, OCH₃] | 170 |
| 907 | — | O | C₃H₇-i | (6-) CH₃ | ![triazolinone with N-CH₃, N-CH₂-cyclopropyl, OCH₃] | 125 |
| 908 | — | O | C₃H₇-i | (6-) CH₃ | ![triazolinone with N-CH₃, N-CH₂-cyclopropyl, OC₂H₅] | 129 |

TABLE 1-continued

Examples of the compounds of the formula (I)

| Ex. No. | A | Q | R¹ | (position-) R² | R³ | Melting point (° C.) |
|---|---|---|---|---|---|---|
| 909 | — | O | $C_3H_7$-i | (6-) $CH_3$ | 2,5-dimethyl-1,3,4-oxadiazole | 156 |
| 910 | — | O | $CH_3$ | (6-) $OCH_3$ | 1,4-dimethyl-3-ethoxy-1,2,4-triazol-5(4H)-one | 157 |
| 911 | — | O | $CH_3$ | (6-) $OCH_3$ | 1,4-dimethyl-3-ethyl-1,2,4-triazol-5(4H)-one | 177 |
| 912 | — | O | $CH_3$ | (6-) $OCH_3$ | 1,4-dimethyl-3-methylthio-1,2,4-triazol-5(4H)-one | 172 |
| 913 | — | O | $C_3H_7$-i | (6-) $CH_3$ | 1-methyl-4-cyclopropyl-3-(2-chloroethylthio)-1,2,4-triazol-5(4H)-one | 132 |
| 914 | — | O | $C_3H_7$-i | (6-) $CH_3$ | 1-methyl-4-methoxy-3-methylthio-1,2,4-triazol-5(4H)-one | 153 |
| 915 | — | O | $C_3H_7$-i | (6-) $CH_3$ | 1-methyl-4-methoxy-3-ethylthio-1,2,4-triazol-5(4H)-one | 150 |
| 916 | — | O | $C_3H_7$-i | (6-) $CH_3$ | 1-methyl-4-cyclopropylmethyl-3-n-propoxy-1,2,4-triazol-5(4H)-one | 110 |

TABLE 1-continued

Examples of the compounds of the formula (I)

| Ex. No. | A | Q | R¹ | (position-) R² | R³ | Melting point (° C.) |
|---|---|---|---|---|---|---|
| 917 | — | O | $C_3H_7$-i | (6-) $CH_3$ | (1-methyl-4-methyl-5-(SCH₂CH₂F)-1,2,4-triazol-3(4H)-one) | 131 |
| 918 | — | O | $C_3H_7$-i | (6-) $CH_3$ | (1-methyl-4-cyclopropyl-5-(SCH₂CH₂F)-1,2,4-triazol-3(4H)-one) | 133 |
| 919 | — | O | $CH_3$ | (6-) $OCH_3$ | (1-methyl-4-methyl-5-(O—CH₂-cyclopropyl)-1,2,4-triazol-3(4H)-one) | 153 |
| 920 | — | O | $C_3H_7$-i | (6-) $CH_3$ | (1-methyl-4-methyl-5-(SCH₂Cl)-1,2,4-triazol-3(4H)-one) | 122 |
| 921 | — | O | $C_3H_7$-i | (6-) $CH_3$ | (1-methyl-4-OCH₃-5-OCH₃-1,2,4-triazol-3(4H)-one) | 147 |
| 922 | — | O | $CH_3$ | (6-) $OCH_3$ | (1-methyl-4-methyl-5-OCH₃-1,2,4-triazol-3(4H)-one) | 160 |
| 923 | — | O | $CH_3$ | (6-) $OCH_3$ | (1-methyl-4-methyl-5-OC₃H₇-n-1,2,4-triazol-3(4H)-one) | 182 |
| 924 | — | O | $CH_3$ | (6-) $OCH_3$ | (1-methyl-4-methyl-5-OC₃H₇-i-1,2,4-triazol-3(4H)-one) | 142 |

TABLE 1-continued

Examples of the compounds of the formula (I)

| Ex. No. | A | Q | R¹ | (position-) R² | R³ | Melting point (° C.) |
|---|---|---|---|---|---|---|
| 925 | — | O | CH₃ | (6-) OCH₃ | ![structure: N-methyl-N'-methyl-triazolone-OCH₂CF₃] | 178 |
| 926 | — | O | C₃H₇-i | (6-) CH₃ | ![structure: triazolone with N-OC₂H₅ and OC₂H₅] | 151 |
| 927 | — | O | CH₃ | (6-) OCH₃ | ![structure: N-cyclopropyl triazolone-OCH₃] | 178 |
| 928 | — | O | CH₃ | (6-) OCH₃ | ![structure: N-cyclopropyl triazolone-OC₂H₅] | 130 |
| 929 | — | O | CH₃ | (6-) OCH₃ | ![structure: N-cyclopropyl triazolone-OC₃H₇-n] | 124 |
| 930 | — | O | CH₃ | (6-) OCH₃ | ![structure: N-cyclopropyl triazolone-OC₃H₇-i] | 153 |
| 931 | — | O | CH₃ | (6-) OCH₃ | ![structure: N-cyclopropyl triazolone-OCH₂CF₃] | 157 |
| 932 | — | O | CH₃ | (6-) OCH₃ | ![structure: N-cyclopropyl triazolone-OCH₂CH=CH₂] | 114 |

TABLE 1-continued

Examples of the compounds of the formula (I)

| Ex. No. | A  | Q | R¹       | (position-) R² | R³ | Melting point (° C.) |
|---------|----|---|----------|----------------|----|----------------------|
| 933     | —  | O | CH₃      | (6-) OCH₃      |    | 130                  |
| 934     | —  | O | C₃H₇-i   | (6-) CH₃       |    | 151                  |
| 935     | —  | O | C₃H₇-i   | (6-) CH₃       |    | 153                  |
| 936     | —  | O | CH₃      | (6-) OCH₃      |    | 167                  |
| 937     | —  | O | CF₂Cl    | (6-) CH₃       |    | 180 (Na salt)        |
| 938     | —  | O | CH₃      | (6-) OCH₃      |    | 157 (Na salt)        |
| 939     | NH | O | CH₂CH₂F  | (6-) CH₃       |    | 163                  |
| 940     | NH | O | CH₂CHF₂  | (6-) CH₃       |    | 160                  |

TABLE 1-continued

Examples of the compounds of the formula (I)

| Ex. No. | A | Q | R¹ | (position-) R² | R³ | Melting point (° C.) |
|---|---|---|---|---|---|---|
| 941 | NH | O | CF$_2$CHFCl | (6-) CH$_3$ | 1,2,4-triazol-3(2H)-one, 2-methyl-4-methyl-5-OC$_2$H$_5$ | 88 |
| 942 | — | O | CH$_2$CH$_2$F | (6-) CH$_3$ | 1,2,4-triazol-3(2H)-one, 2-methyl-4-cyclopropyl-5-OCH$_3$ | 178 |
| 943 | — | O | CH$_2$CH$_2$F | (6-) CH$_3$ | 1,2,4-triazol-3(2H)-one, 2-methyl-4-cyclopropyl-5-OC$_3$H$_7$-i | 135 |
| 944 | — | O | CH$_2$CH$_2$F | (6-) CH$_3$ | 1,2,4-triazol-3(2H)-one, 2-methyl-4-methyl-5-OC$_3$H$_7$-n | 127 |
| 945 | — | O | CH$_2$CH$_2$F | (6-) CH$_3$ | 1,2,4-triazol-3(2H)-one, 2-methyl-4-methyl-5-OC$_3$H$_7$-i | 139 |
| 946 | — | O | CH$_2$CH$_2$F | (6-) CH$_3$ | 1,2,4-triazol-3(2H)-one, 2-methyl-4-methyl-5-CH$_3$ | 280 (Na salt) |
| 947 | — | O | CH$_2$CH$_2$F | (6-) CH$_3$ | 1,2,4-triazol-3(2H)-one, 2-methyl-4-methyl-5-OCH$_3$ | 171 |
| 948 | — | O | CH$_2$CH$_2$F | (6-) CH$_3$ | 1,2,4-triazol-3(2H)-one, 2-methyl-4-methyl-5-OC$_2$H$_5$ | 144 |

TABLE 1-continued
Examples of the compounds of the formula (I)
| Ex. No. | A | Q | R¹ | (position-) R² | R³ | Melting point (° C.) |
|---|---|---|---|---|---|---|
| 949 | — | O | CH₂CHF₂ | (6-) CH₃ | 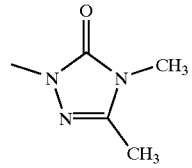 | 273 (Na salt) |
| 950 | — | O | CH₂CHF₂ | (6-) CH₃ | 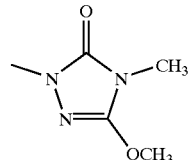 | 181 |
| 951 | — | O | CH₂CHF₂ | (6-) CH₃ | 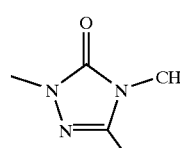 | 142 |
| 952 | — | O | CH₂CHF₂ | (6-) CH₃ | 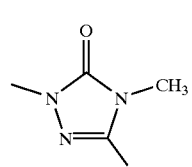 | 114 |
| 953 | — | O | CH₂CHF₂ | (6-) CH₃ | 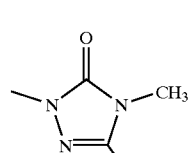 | 108 |
| 954 | — | O | CH₂CHF₂ | (6-) CH₃ | 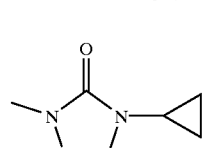 | 185 |
| 955 | — | O | CH₂CHF₂ | (6-) CH₃ | 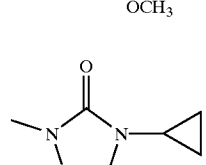 | 150 |
| 956 | — | O | CF₃ | (6-) C₂H₅ | 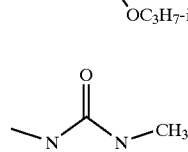 | 143 (Na salt) |

TABLE 1-continued

Examples of the compounds of the formula (I)

| Ex. No. | A | Q | R¹ | (position-) R² | R³ | Melting point (° C.) |
|---|---|---|---|---|---|---|
| 957 | — | O | $CF_3$ | (6-) $CH_3$ | triazolinone with $N-CH_3$, $N-CH_3$, $OCH_2CF_3$ | 155 |
| 958 | — | O | $CF_3$ | (6-) $CH_3$ | triazolinone with $N-CH_3$, $N-CH_3$, $O-CH_2$-cyclopropyl | 112 |
| 959 | — | O | $CF_3$ | (6-) $CH_3$ | triazolinone with $N-CH_3$, $N$-cyclopropyl, $OCH_3$ | 166 |
| 960 | — | O | $CF_3$ | (6-) $CH_3$ | triazolinone with $N-CH_3$, $N$-cyclopropyl, $OC_2H_5$ | 137 |
| 961 | — | O | $CF_3$ | (6-) $CH_3$ | triazolinone with $N-CH_3$, $N$-cyclopropyl, $OC_3H_7$-n | 132 |
| 962 | — | O | $CF_3$ | (6-) $CH_3$ | triazolinone with $N-CH_3$, $N$-cyclopropyl, $OCH_2CF_3$ | 172 |
| 963 | — | O | $CF_3$ | (6-) $CH_3$ | triazolinone with $N-CH_3$, $N$-cyclopropyl, $O-CH_2$-cyclopropyl | 139 |
| 964 | — | O | $CF_3$ | (6-) $CH_3$ | triazolinone with $N-CH_3$, $N-CH_3$, $OC_3H_7$-i | 130 |

TABLE 1-continued

Examples of the compounds of the formula (I)

| Ex. No. | A | Q | $R^1$ | (position-) $R^2$ | $R^3$ | Melting point (° C.) |
|---|---|---|---|---|---|---|
| 965 | — | O | $C_2H_5$ | (3-) $CH_3$ | 1,4-dimethyl-3-oxo-5-(methylthio)-1,2,4-triazol-yl | 184 |

TABLE 1A

Examples of the compounds of the formula (IA)

(IA)

Structure: aryl with $R^1O$–, $R^2$ substituent, –A–SO$_2$–NH–C(Q)–N(triazolinone with Q$^1$, $R^4$, $R^5$)

| Ex. No. | A | Q | $R^1$ | (Position-) $R^2$ | $Q^1$ | $R^4$ | $R^5$ | Melting point ° C. |
|---|---|---|---|---|---|---|---|---|
| 966 | NH | O | $C_4H_9$ | (6-)$CH_3$ | O | cyclopropyl | $OC_2H_5$ | 121 |
| 967 | NH | O | $CH_2CH(CH_3)_2$ | (6-)$CH_3$ | O | cyclopropyl | $OC_2H_5$ | 127 |
| 968 | NH | O | $CH_2CF_3$ | (6-)$CH_3$ | O | $CH_3$ | $OCH_3$ | 164 |
| 969 | NH | O | $CH_2CF_3$ | (6-)$CH_3$ | O | $CH_3$ | $OC_2H_5$ | 138 |
| 970 | NH | O | $CH_2CF_3$ | (6-)$CH_3$ | O | $CH_3$ | $OC_3H_7$ | 123 |
| 971 | NH | O | $CH_2CF_3$ | (6-)$CH_3$ | O | $CH_3$ | $OCH(CH_3)_2$ | 141 |
| 972 | — | O | $CH_2CH_2F$ | (3-)Cl | O | $CH_3$ | $OC_2H_5$ | 139 |
| 973 | — | O | $CH_2CH_2F$ | (3-)$CH_3$ | O | $CH_3$ | $OC_2H_5$ | 154 |
| 974 | — | O | $C_3H_7$-i | (6-)$CF_3$ | O | cyclopropyl | $C_4H_9$-s | |
| 975 | — | O | $C_3H_7$-i | (6-)$CF_3$ | O | $CH_3$ | $C_4H_9$-s | |
| 976 | — | O | $C_3H_7$-i | (6-)$CF_3$ | O | $CH_3$ | $C_4H_9$ | |
| 977 | — | O | $C_3H_7$-i | (6-)$CF_3$ | O | $CH_3$ | $C_4H_9$-i | |
| 978 | — | S | $C_3H_7$-i | (6-)$CF_3$ | O | $CH_3$ | $C_2H_5$ | |
| 979 | — | S | $C_3H_7$ | (6-)$CH_3$ | O | cyclopropyl | $OC_2H_5$ | |
| 980 | — | S | $C_3H_7$ | (6-)$CH_3$ | O | $C_2H_5$ | $OC_2H_5$ | |
| 981 | — | S | $C_3H_7$-i | (6-)$CH_3$ | O | cyclopropyl | $OC_2H_5$ | |
| 982 | — | S | $C_3H_7$-i | (6-)$CH_3$ | O | $C_2H_5$ | $OC_2H_5$ | |
| 983 | — | S | $C_3H_7$ | (6-)$CH_3$ | O | $CH_3$ | $OC_3H_7$-i | |
| 984 | — | S | $C_3H_7$-i | (6-)$CH_3$ | O | $CH_3$ | $OC_3H_7$-i | |
| 985 | — | S | $C_3H_7$ | (6-)$CH_3$ | O | $CH_3$ | $OC_3H_7$ | |
| 986 | — | S | $C_3H_7$-i | (6-)$CH_3$ | O | $CH_3$ | $OC_3H_7$ | |
| 987 | — | S | $C_3H_7$ | (6-)$CH_3$ | O | cyclopropyl | $OCH_3$ | |
| 988 | — | O | $CH_3$ | (6-)$CF_3$ | O | cyclopropyl | $C_4H_9$-s | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 989 | — | O | C₂H₅ | (6-)CF₃ | O | ▷ | C₄H₉-s | |
| 990 | — | O | C₃H₇ | (6-)CF₃ | O | ▷ | C₄H₉-s | |
| 991 | — | O | CH₃ | (6-)CF₃ | O | CH₃ | C₄H₉-s | |
| 992 | — | O | C₂H₅ | (6-)CF₃ | O | CH₃ | C₄H₉-s | |
| 993 | — | O | CH₃ | (6-)CF₃ | O | CH₃ | C₄H₉ | |
| 994 | — | O | CH₃ | (6-)CF₃ | O | ▷ | C₄H₉-t | |
| 995 | — | O | CH₃ | (6-)CF₃ | O | ▷ | OC₃H₇ | |
| 996 | — | O | C₂H₅ | (6-)CF₃ | O | ▷ | OC₃H₇ | |
| 997 | — | O | C₃H₇ | (6-)CF₃ | O | ▷ | OC₃H₇ | |
| 998 | — | O | C₂H₅ | (6-)CF₃ | O | CH₃ | C₄H₉ | |
| 999 | — | O | C₃H₇ | (6-)CF₃ | O | CH₃ | C₄H₉ | |
| 1000 | — | O | CH₃ | (6-)CF₃ | O | CH₃ | C₄H₉-i | |
| 1001 | — | S | CH₃ | (6-)CF₃ | O | CH₃ | SCH₃ | |
| 1002 | — | S | CH₃ | (6-)CF₃ | O | ▷ | OC₂H₅ | |
| 1003 | — | S | CH₃ | (6-)CF₃ | O | CH₃ | OC₃H₇-i | |
| 1004 | — | S | CH₃ | (6-)CF₃ | O | C₂H₅ | OC₂H₅ | |
| 1005 | — | S | CH₃ | (6-)CF₃ | O | ▷ | OC₃H₇ | |
| 1006 | — | S | CH₃ | (6-)CF₃ | O | ▷ | OC₃H₇-i | |
| 1007 | — | S | CH₃ | (6-)CF₃ | O | CH₃ | OCH₂CF₃ | |
| 1008 | — | S | CH₃ | (6-)CF₃ | O | CH₃ | OC₃H₇ | |
| 1009 | — | S | CH₃ | (6-)CF₃ | O | ▷ | ▷ | |
| 1010 | — | S | CH₃ | (6-)CF₃ | O | ▷ | OCH₃ | |
| 1011 | — | S | CH₃ | (6-)CF₃ | O | ▷ | OCH₂CF₃ | |
| 1012 | — | S | CH₃ | (6-)CH₃ | O | CH₃ | CH₃ | |

TABLE 1A-continued

Examples of the compounds of the formula (IA)

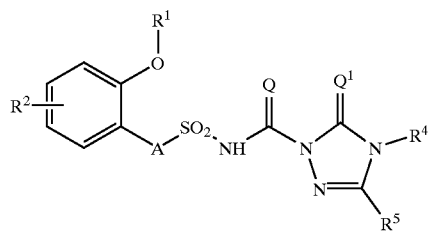

(IA)

| Ex. No. | A | Q | R¹ | (Position-) R² | Q¹ | R⁴ | R⁵ | Melting point ° C. |
|---|---|---|---|---|---|---|---|---|
| 1013 | — | S | CH₃ | (6-)CH₃ | O | CH₃ | OCH₃ | |
| 1014 | — | S | CH₃ | (6-)CH₃ | O | CH₃ | OC₂H₅ | |
| 1015 | — | S | CH₃ | (6-)CH₃ | O | CH₃ | OH₅ | |
| 1016 | — | S | C₂H₅ | (6-)CH₃ | O | CH₃ | C₂H₅ | |
| 1017 | — | S | CH₃ | (6-)CH₃ | O | CH₃ | SCH₃ | |
| 1018 | — | S | C₂H₅ | (6-)CH₃ | O | CH₃ | SCH₃ | |
| 1019 | — | S | CH₃ | (6-)CH₃ | O | c-C₃H₅ | OC₂H₅ | |
| 1020 | — | S | C₂H₅ | (6-)CH₃ | O | c-C₃H₅ | OC₂H₅ | |
| 1021 | — | S | CH₃ | (6-)CH₃ | O | CH₃ | OC₃H₇-i | |
| 1022 | — | S | C₂H₅ | (6-)CH₃ | O | c-C₃H₅ | OC₃H₇ | |
| 1023 | — | O | CH₃ | (6-)CF₃ | O | —CH₂—CH=CH₂ | OCH₂CF₃ | |
| 1024 | — | O | CH₃ | (6-)CF₃ | O | c-C₃H₅ | C₃H₇-i | |
| 1025 | — | O | CH₃ | (6-)CF₃ | O | CH₃ | C₄H₉-t | |
| 1026 | — | O | CH₃ | (6-)CF₃ | O | c-C₃H₅ | C₃H₇ | |
| 1027 | — | O | CH₃ | (6-)CF₃ | O | c-C₃H₅ | C₃H₇-i | |
| 1028 | — | O | CH₃ | (6-)CF₃ | O | C₂H₅ | C₂H₅ | |
| 1029 | — | O | CH₃ | (6-)CF₃ | O | C₃H₇ | C₂H₅ | |
| 1030 | — | O | CH₃ | (6-)CF₃ | O | C₃H₇-i | C₂H₅ | |
| 1031 | — | O | CH₃ | (6-)CF₃ | O | C₂H₅ | C₃H₇ | |
| 1032 | — | O | CH₃ | (6-)CF₃ | O | C₃H₇ | C₃H₇ | |
| 1033 | — | O | CH₃ | (6-)CF₃ | O | N(CH₃)₂ | CH₃ | |
| 1034 | — | O | CH₃ | (6-)CF₃ | O | CH₃ | H | |
| 1035 | — | O | CH₃ | (6-)CF₃ | O | CH₃ | CH₂CH₂O | |
| 1036 | — | O | CH₃ | (6-)CF₃ | O | CH₃ | c-C₃H₅ | |
| 1037 | — | O | CH₃ | (6-)CF₃ | O | C₃H₇-i | C₃H₇ | |
| 1038 | — | O | CH₃ | (6-)CF₃ | O | C₂H₅ | C₃H₇-i | |
| 1039 | — | O | CH₃ | (6-)CF₃ | O | C₃H₇ | C₃H₇-i | |
| 1040 | — | O | CH₃ | (6-)CF₃ | O | C₃H₇-i | C₃H₇-i | |
| 1041 | — | O | CH₃ | (6-)CF₃ | O | C₂H₅ | c-C₃H₅ | |
| 1042 | — | O | CH₃ | (6-)CF₃ | O | C₃H₇ | c-C₃H₅ | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1043 | — | O | CH₃ | (6-)CF₃ | O | $C_3H_7$-i |  | |
| 1044 | — | O | C₂H₅ | (6-)CF₃ | O | $C_3H_7$-i |  | |
| 1045 | — | O | C₃H₇ | (6-)CF₃ | O | $C_3H_7$-i |  | |
| 1046 | — | O | CH₃ | (6-)CF₃ | O | CH₃ | OCH₂CF₂CHF₂ | |
| 1047 | — | O | C₃H₇ | (6-)CF₃ | O | CH₃ | OCH₂CF₂CHF₂ | |
| 1048 | — | O | CH₃ | (6-)CF₃ | O | CH₃ | OC₆H₁₁ | |
| 1049 | — | O | C₂H₅ | (6-)CF₃ | O | CH₃ | OC₆H₁₁ | |
| 1050 | — | O | C₃H₇ | (6-)CF₃ | O | CH₃ | OC₆H₁₁ | |
| 1051 | — | O | CH₃ | (6-)CF₃ | O | CH₃ | O—CH(CH₃)—CH₂—CH₃ | |
| 1052 | — | O | CH₃ | (6-)CF₃ | O |  | $C_4H_9$-i | |
| 1053 | — | O | CH₃ | (6-)CF₃ | O |  | C₄H₉ | |
| 1054 | — | O | CH₃ | (6-)CF₃ | O |  | CH₃ | |
| 1055 | — | O | CH₃ | (6-)CF₃ | O |  | C₂H₅ | |
| 1056 | — | O | CH₃ | (6-)CF₃ | O |  |  | |
| 1057 | — | O | CH₃ | (6-)CF₃ | O | C₂H₅ | CH₃ | |
| 1058 | — | O | $C_3H_7$-i | (6-)CF₃ | O | $C_3H_7$-i |  | |
| 1059 | — | O | $C_3H_7$-i | (6-)CF₃ | O | CH₃ | OCH₂CF₂CHF₂ | |
| 1060 | — | O | C₃H₇ | (6-)CF₃ | O | CH₃ | CH₃ | |
| 1061 | — | O | C₃H₇ | (6-)CF₃ | O | CH₃ | $C_3H_7$-i | |
| 1062 | — | O | C₃H₇ | (6-)CF₃ | O | CH₃ | CH₂OCH₃ | |
| 1063 | — | O | C₃H₇ | (6-)CF₃ | O | CH₃ | Br | |
| 1064 | — | O | C₂H₅ | (6-)CF₃ | O | CH₃ | OCH₂CF₃ | |
| 1065 | — | O | C₃H₇ | (6-)CF₃ | O | OCH₃ | C₃H₇ | |
| 1066 | — | O | C₃H₇ | (6-)CF₃ | O |  | Br | |
| 1067 | — | O | C₂H₅ | (6-)CF₃ | O |  | CH₂OCH₃ | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1068 | — | O | $C_3H_7$ | (6-)$CF_3$ | O | ▷ | $CH_2OCH_3$ | |
| 1069 | — | S | $C_2H_5$ | (6-)$CF_3$ | O | $CH_3$ | $SCH_3$ | |
| 1070 | — | S | $C_3H_7$ | (6-)$CF_3$ | O | $CH_3$ | $SCH_3$ | |
| 1071 | — | S | $C_3H_7$-i | (6-)$CF_3$ | O | $CH_3$ | $SCH_3$ | |
| 1072 | — | S | $C_2H_5$ | (6-)$CF_3$ | O | ▷ | $OC_2H_5$ | |
| 1073 | — | S | $C_3H_7$ | (6-)$CF_3$ | O | ▷ | $OC_2H_5$ | |
| 1074 | — | S | $C_3H_7$-i | (6-)$CF_3$ | O | ▷ | $OC_2H_5$ | |
| 1075 | — | S | $C_2H_5$ | (6-)$CF_3$ | O | $CH_3$ | $OC_3H_7$-i | |
| 1076 | — | S | $C_3H_7$ | (6-)$CF_3$ | O | $CH_3$ | $OC_3H_7$-i | |
| 1077 | — | S | $C_3H_7$-i | (6-)$CF_3$ | O | $CH_3$ | $OC_3H_7$-i | |
| 1078 | — | S | $C_2H_5$ | (6-)$CF_3$ | O | $C_2H_5$ | $OC_2H_5$ | |
| 1079 | — | S | $C_3H_7$ | (6-)$CF_3$ | O | $C_2H_5$ | $OC_2H_5$ | |
| 1080 | — | S | $C_3H_7$-i | (6-)$CF_3$ | O | $C_2H_5$ | $OC_2H_5$ | |
| 1081 | — | S | $C_2H_5$ | (6-)$CF_3$ | O | ▷ | $OC_3H_7$ | |
| 1082 | — | S | $C_3H_7$ | (6-)$CF_3$ | O | ▷ | $OC_3H_7$ | |
| 1083 | — | S | $C_3H_7$-i | (6-)$CF_3$ | O | ▷ | $OC_3H_7$ | |
| 1084 | — | O | $C_3H_7$-i | (6-)$CF_3$ | O | ▷ | $C_4H_9$-t | |
| 1085 | — | O | $C_2H_5$ | (6-)$CF_3$ | O | $CH_3$ | $OC_4H_9$-s | |
| 1086 | — | O | $C_3H_7$ | (6-)$CF_3$ | O | $CH_3$ | O—CH(CH₃)—$CH_2$—$CH_3$ | |
| 1087 | — | O | $C_3H_7$-i | (6-)$CF_3$ | O | $CH_3$ | $OC_4H_9$-s | |
| 1088 | — | O | $C_2H_5$ | (6-)$CF_3$ | O | $CH_3$ | $OC_6H_5$ | |
| 1089 | — | O | $C_3H_7$ | (6-)$CF_3$ | O | $CH_3$ | $OC_6H_5$ | |
| 1090 | — | O | $C_3H_7$-i | (6-)$CF_3$ | O | $CH_3$ | $OC_6H_5$ | |
| 1091 | — | O | $C_2H_5$ | (6-)$CF_3$ | O | $CH_2CH=CH_2$ | $OCH_2CF_3$ | |
| 1092 | — | O | $C_3H_7$ | (6-)$CF_3$ | O | $CH_2CH=CH_2$ | $OCH_2CF_3$ | |
| 1093 | — | O | $C_3H_7$-i | (6-)$CF_3$ | O | $CH_2CH=CH_2$ | $OCH_2CF_3$ | |
| 1094 | — | O | $C_2H_5$ | (6-)$CF_3$ | O | $CH_3$ | $OCH_2C_2H_5$ | |
| 1095 | — | O | $C_3H_7$ | (6-)$CF_3$ | O | $CH_3$ | $OCH_2C_6H_5$ | |
| 1096 | — | O | $C_3H_7$-i | (6-)$CF_3$ | O | $CH_3$ | $OCH_2C_6H_5$ | |
| 1097 | — | O | $C_2H_5$ | (6-)$CF_3$ | O | $N(CH_3)_2$ | $CH_3$ | |
| 1098 | — | O | $C_3H_7$ | (6-)$CF_3$ | O | $N(CH_3)_2$ | $CH_3$ | |
| 1099 | — | O | $C_3H_7$-i | (6-)$CF_3$ | O | $N(CH_3)_2$ | $CH_3$ | |
| 1100 | — | O | $C_3H_7$ | (6-)$CF_3$ | O | $CH_3$ | H | |
| 1101 | — | O | $C_2H_5$ | (6-)$CF_3$ | O | $CH_3$ | $CH_2CH_2OC_3H_7$-i | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1102 | — | O | C₃H₇-i | (6-)CF₃ | O | CH₃ | CH₂CH₂OC₃H₇-i | |
| 1103 | — | O | OH | (6-)CF₃ | O | CH₃ | cyclopropyl | |
| 1104 | — | O | C₃H₇ | (6-)CF₃ | O | CH₃ | cyclopropyl | |
| 1105 | — | O | C₃H₇-i | (6-)CF₃ | O | CH₃ | cyclopropyl | |
| 1106 | — | O | C₂H₅ | (6-)CF₃ | O | CH₃ | OCH₂CF₂CHF₂ | |
| 1107 | — | S | C₃H₇-i | (6-)CH₃ | O | cyclopropyl | OCH₃ | |
| 1108 | — | S | C₃H₇ | (6-)CH₃ | O | cyclopropyl | OC₃H₇-i | |
| 1109 | — | S | C₃H₇-i | (6-)CH₃ | O | cyclopropyl | OC₃H₇-i | |
| 1110 | — | S | C₃H₇ | (6-)CH₃ | O | cyclopropyl | OC₃H₇ | |
| 1111 | — | S | C₃H₇-i | (6-)CH₃ | O | cyclopropyl | OC₃H₇ | |
| 1112 | — | O | C₂H₅ | (6-)CF₃ | O | cyclopropyl | C₄H₉-i | |
| 1113 | — | O | C₃H₇ | (6-)CF₃ | O | cyclopropyl | C₄H₉-i | |
| 1114 | — | O | C₃H₇-i | (6-)CF₃ | O | cyclopropyl | C₄H₉-i | |
| 1115 | — | O | C₂H₅ | (6-)CF₃ | O | cyclopropyl | C₄H₉ | |
| 1116 | — | O | C₃H₇ | (6-)CF₃ | O | cyclopropyl | C₄H₉ | |
| 1117 | — | O | C₃H₇-i | (6-)CF₃ | O | cyclopropyl | C₄H₉ | |
| 1118 | — | O | C₂H₅ | (6-)CF₃ | O | cyclopropyl | CH₃ | |
| 1119 | — | O | C₃H₇ | (6-)CF₃ | O | cyclopropyl | CH₃ | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1120 | — | O | $C_3H_7$-i | (6-)$CF_3$ | O | cyclopropyl | $CH_3$ | |
| 1121 | — | O | $C_2H_5$ | (6-)$CF_3$ | O | cyclopropyl | $C_2H_5$ | |
| 1122 | — | O | $C_3H_7$ | (6-)$CF_3$ | O | cyclopropyl | $C_2H_5$ | |
| 1123 | — | O | $C_3H_7$-i | (6-)$CF_3$ | O | cyclopropyl | $C_2H_5$ | |
| 1124 | — | O | $C_2H_5$ | (6-)$CF_3$ | O | cyclopropyl | cyclopropyl | |
| 1125 | — | O | $C_3H_7$ | (6-)$CF_3$ | O | cyclopropyl | cyclopropyl | |
| 1126 | — | O | $C_3H_7$-i | (6-)$CF_3$ | O | cyclopropyl | cyclopropyl | |
| 1127 | — | O | $C_2H_5$ | (6-)$CF_3$ | O | $C_3H_7$ | cyclopropyl | |
| 1128 | — | O | $C_3H_7$ | (6-)$CF_3$ | O | $C_3H_7$ | cyclopropyl | |
| 1129 | — | O | $C_3H_7$-i | (6-)$CF_3$ | O | $C_3H_7$ | cyclopropyl | |
| 1130 | — | O | $C_2H_5$ | (6-)$CF_3$ | O | $C_2H_5$ | $CH_3$ | |
| 1131 | — | O | $C_3H_7$ | (6-)$CF_3$ | O | $C_2H_5$ | $CH_3$ | |
| 1132 | — | O | $C_3H_7$-i | (6-)$CF_3$ | O | $C_2H_5$ | $CH_3$ | |
| 1133 | — | O | $C_2H_5$ | (6-)$CF_3$ | O | cyclopropyl | $C_3H_7$ | |
| 1134 | — | O | $C_3H_7$ | (6-)$CF_3$ | O | cyclopropyl | $C_3H_7$ | |
| 1135 | — | O | $C_3H_7$-i | (6-)$CF_3$ | O | cyclopropyl | $C_3H_7$ | |
| 1136 | — | O | $C_2H_5$ | (6-)$CF_3$ | O | cyclopropyl | $C_3H_7$-i | |
| 1137 | — | O | $C_3H_7$ | (6-)$CF_3$ | O | cyclopropyl | $C_3H_7$-i | |

TABLE 1A-continued

Examples of the compounds of the formula (IA)

(IA)

| Ex. No. | A | Q | R¹ | (Position-)R² | Q¹ | R⁴ | R⁵ | Melting point °C. |
|---|---|---|---|---|---|---|---|---|
| 1138 | — | O | $C_3H_7$-i | (6-)$CF_3$ | O | c-$C_3H_5$ | $C_3H_7$-i | |
| 1139 | — | O | $C_2H_5$ | (6-)$CF_3$ | O | $C_2H_5$ | $C_2H_5$ | |
| 1140 | — | O | $C_3H_7$ | (6-)$CF_3$ | O | $C_2H_5$ | $C_2H_5$ | |
| 1141 | — | O | $C_3H_7$-i | (6-)$CF_3$ | O | $C_2H_5$ | $C_2H_5$ | |
| 1142 | — | O | $C_2H_5$ | (6-)$CF_3$ | O | $C_3H_7$ | $C_2H_5$ | |
| 1143 | — | O | $C_3H_7$ | (6-)$CF_3$ | O | $C_3H_7$ | $C_2H_5$ | |
| 1144 | — | O | $C_3H_7$-i | (6-)$CF_3$ | O | $C_3H_7$ | $C_2H_5$ | |
| 1145 | — | S | $C_2H_5$ | (6-)$CF_3$ | O | c-$C_3H_5$ | $OC_3H_7$-i | |
| 1146 | — | S | $C_3H_7$ | (6-)$CF_3$ | O | c-$C_3H_5$ | $OC_3H_7$-i | |
| 1147 | — | S | $C_3H_7$-i | (6-)$CF_3$ | O | c-$C_3H_5$ | $OC_3H_7$-i | |
| 1148 | — | S | $C_2H_5$ | (6-)$CF_3$ | O | $CH_3$ | $OCH_2CF_3$ | |
| 1149 | — | S | $C_3H_7$ | (6-)$CF_3$ | O | $CH_3$ | $OCH_2CF_3$ | |
| 1150 | — | S | $C_3H_7$-i | (6-)$CF_3$ | O | $CH_3$ | $OCH_2CF_3$ | |
| 1151 | — | S | $C_2H_5$ | (6-)$CF_3$ | O | $CH_3$ | $OC_3H_7$ | |
| 1152 | — | S | $C_3H_7$ | (6-)$CF_3$ | O | $CH_3$ | $OC_3H_7$ | |
| 1153 | — | S | $C_3H_7$-i | (6-)$CF_3$ | O | $CH_3$ | $OC_3H_7$ | |
| 1154 | — | S | $C_2H_5$ | (6-)$CF_3$ | O | c-$C_3H_5$ | c-$C_3H_5$ | |
| 1155 | — | S | $C_3H_7$ | (6-)$CF_3$ | O | c-$C_3H_5$ | c-$C_3H_5$ | |
| 1156 | — | S | $C_3H_7$-i | (6-)$CF_3$ | O | c-$C_3H_5$ | c-$C_3H_5$ | |
| 1157 | — | S | $C_2H_5$ | (6-)$CF_3$ | O | c-$C_3H_5$ | $OCH_3$ | |
| 1158 | — | S | $C_3H_7$ | (6-)$CF_3$ | O | c-$C_3H_5$ | $OCH_3$ | |
| 1159 | — | S | $C_3H_7$-i | (6-)$CF_3$ | O | c-$C_3H_5$ | $OCH_3$ | |
| 1160 | — | S | $C_2H_5$ | (6-)$CF_3$ | O | c-$C_3H_5$ | $OCH_2CF_3$ | |
| 1161 | — | S | $C_3H_7$ | (6-)$CF_3$ | O | c-$C_3H_5$ | $OCH_2CF_3$ | |
| 1162 | — | S | $C_3H_7$-i | (6-)$CF_3$ | O | c-$C_3H_5$ | $OCH_2CF_3$ | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1163 | — | O | $C_2H_5$ | (6-)$CF_3$ | O | $C_3H_7$-i | $C_3H_7$ | |
| 1164 | — | O | $C_3H_7$ | (6-)$CF_3$ | O | $C_3H_7$-i | $C_3H_7$ | |
| 1165 | — | O | $C_3H_7$-i | (6-)$CF_3$ | O | $C_3H_7$-i | $C_3H_7$ | |
| 1166 | — | O | $C_2H_5$ | (6-)$CF_3$ | O | $C_2H_5$ | $C_3H_7$-i | |
| 1167 | — | O | $C_3H_7$ | (6-)$CF_3$ | O | $C_2H_5$ | $C_3H_7$-i | |
| 1168 | — | O | $C_3H_7$-i | (6-)$CF_3$ | O | $C_2H_5$ | $C_3H_7$-i | |
| 1169 | — | O | $C_2H_5$ | (6-)$CF_3$ | O | $C_3H_7$ | $C_3H_7$-i | |
| 1170 | — | O | $C_3H_7$ | (6-)$CF_3$ | O | $C_3H_7$ | $C_3H_7$-i | |
| 1171 | — | O | $C_3H_7$-i | (6-)$CF_3$ | O | $C_3H_7$ | $C_3H_7$-i | |
| 1172 | — | O | $C_2H_5$ | (6-)$CF_3$ | O | $C_3H_7$-i | $C_3H_7$-i | |
| 1173 | — | O | $C_3H_7$ | (6-)$CF_3$ | O | $C_3H_7$-i | $C_3H_7$-i | |
| 1174 | — | O | $C_3H_7$-i | (6-)$CF_3$ | O | $C_3H_7$-i | $C_3H_7$-i | |
| 1175 | — | O | $C_2H_5$ | (6-)$CF_3$ | O | $C_3H_7$-i | $C_2H_5$ | |
| 1176 | — | O | $C_3H_7$ | (6-)$CF_3$ | O | $C_3H_7$-i | $C_2H_5$ | |
| 1177 | — | O | $C_3H_7$-i | (6-)$CF_3$ | O | $C_3H_7$-i | $C_2H_5$ | |
| 1178 | — | O | $C_2H_5$ | (6-)$CF_3$ | O | $C_2H_5$ | $C_3H_7$ | |
| 1179 | — | O | $C_3H_7$ | (6-)$CF_3$ | O | $C_2H_5$ | $C_3H_7$ | |
| 1180 | — | O | $C_3H_7$-i | (6-)$CF_3$ | O | $C_2H_5$ | $C_3H_7$ | |
| 1181 | — | O | $C_2H_5$ | (6-)$CF_3$ | O | $C_3H_7$ | $C_3H_7$ | |
| 1182 | — | O | $C_3H_7$ | (6-)$CF_3$ | O | $C_3H_7$ | $C_3H_7$ | |
| 1183 | — | O | $C_3H_7$-i | (6-)$CF_3$ | O | $C_3H_7$ | $C_3H_7$ | |
| 1184 | — | O | $C_2H_5$ | (6-)$CF_3$ | O | $CH_3$ | $C_4H_9$-t | |
| 1185 | — | O | $C_3H_7$ | (6-)$CF_3$ | O | $CH_3$ | $C_4H_9$-t | |
| 1186 | — | O | $C_3H_7$-i | (6-)$CF_3$ | O | $CH_3$ | $C_4H_9$-t | |
| 1187 | — | O | $C_2H_5$ | (6-)$CF_3$ | O |  | $C_4H_9$-t | |
| 1188 | — | O | $C_3H_7$ | (6-)$CF_3$ | O |  | $C_4H_9$-t | |
| 1189 | — | O | $C_2H_5$ | (6-)$CF_3$ | O | $C_2H_5$ |  | |
| 1190 | — | O | $C_3H_7$ | (6-)$CF_3$ | O | $C_2H_5$ |  | |
| 1191 | — | O | $C_3H_7$-i | (6-)$CF_3$ | O | $C_2H_5$ |  | |
| 1192 | — | O | $C_3H_7$-i | (6-)$CF_3$ | O | $CH_3$ | $OC_6H_{11}$ | |
| 1193 | — | S | $C_3H_7$ | (6-)$CH_3$ | O | $CH_3$ | $OCH_2CF_3$ | |
| 1194 | — | S | $C_3H_7$-i | (6-)$CH_3$ | O | $CH_3$ | $OCH_2CF_3$ | |
| 1195 | — | S | $C_3H_7$ | (6-)$CH_3$ | O |  | $OCH_2CF_3$ | |
| 1196 | — | S | $C_3H_7$-i | (6-)$CH_3$ | O |  | $OCH_2CF_3$ | |
| 1197 | — | S | $C_3H_7$-i | (6-)$CH_3$ | O | $CH_3$ | $C_2H_5$ | |
| 1198 | — | S | $CH_3$ | (6-)$CF_3$ | O | $CH_3$ | $C_2H_5$ | |
| 1199 | — | S | $C_2H_5$ | (6-)$CF_3$ | O | $CH_3$ | $C_2H_5$ | |
| 1200 | — | S | $C_3H_7$ | (6-)$CF_3$ | O | $CH_3$ | $C_2H_5$ | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1201 | — | O | C₂H₅ | (6-)CF₃ | O |  | H | |
| 1202 | — | O | CH₃ | (6-)CF₃ | O |  | H | |
| 1203 | — | O | C₃H₇ | (6-)CF₃ | O |  | H | |
| 1204 | — | O | C₃H₇-i | (6-)CF₃ | O |  | H | |
| 1205 | — | O | C₂H₅ | (6-)CF₃ | O |  | OCH₃ | |
| 1206 | — | O | C₃H₇ | (6-)CF₃ | O |  | OCH₃ | |
| 1207 | — | O | C₃H₇-i | (6-)CF₃ | O |  | OCH₃ | |
| 1208 | — | O | CH₃ | (6-)CF₃ | O | CH₂CH=CH₂ | OC₃H₇ | |
| 1209 | — | O | C₂H₅ | (6-)CF₃ | O | CH₂CH=CH₂ | OC₃H₇ | |
| 1210 | — | O | CH₃ | (6-)CF₃ | O | CH₃ | OCH₂C₄H₉-t | |
| 1211 | — | O | C₂H₅ | (6-)CF₃ | O | CH₃ | OCH₂C₄H₉-t | |
| 1212 | — | O | C₃H₇ | (6-)CF₃ | O | CH₃ | OCH₂C₄H₉-t | |
| 1213 | — | O | C₃H₇-i | (6-)CF₃ | O | CH₃ | OCH₂C₄H₉-t | |
| 1214 | — | O | CH₃ | (6-)CF₃ | O | CH₃ | OCH₂CCl₃ | |
| 1215 | — | O | C₂H₅ | (6-)CF₃ | O | CH₃ | OCH₂CCl₃ | |
| 1216 | — | O | C₃H₇ | (6-)CF₃ | O | CH₃ | OCH₂CCl₃ | |
| 1217 | — | O | C₃H₇-i | (6-)CF₃ | O | CH₃ | OCH₂CCl₃ | |
| 1218 | — | O | CH₃ | (6-)CF₃ | O |  | CH=CHCH₃ | |
| 1219 | — | O | C₂H₅ | (6-)CF₃ | O |  | CH=CHCH₃ | |
| 1220 | — | O | CH₃ | (4-)CH₃ | O | CH₃ | SCH₃ | |
| 1221 | — | O | CH₃ | (4-)CH₃ | O | CH₃ | OC₂H₅ | |
| 1222 | — | O | CH₃ | (4-)CH₃ | O |  | OC₂H₅ | |
| 1223 | — | O | CH₃ | (4-)CH₃ | O |  | OC₃H₇ | |
| 1224 | — | O | CH₃ | (4-)CH₃ | O | CH₃ | OC₃H₇ | |
| 1225 | — | O | CH₃ | (4-)CH₃ | O |  | OCH₃ | |
| 1226 | — | O | CH₃ | (6-)CF₃ | O | CH₃ | OCH₂C₆H₅ | |

TABLE 1A-continued

Examples of the compounds of the formula (IA)

(IA)

| Ex. No. | A | Q | R¹ | (Position-) R² | Q¹ | R⁴ | R⁵ | Melting point °C. |
|---|---|---|---|---|---|---|---|---|
| 1227 | — | O | CH₃ | (6-)CF₃ | O | ▷ | CH=CHCH₃ | |
| 1228 | — | O | CH₃ | (6-)CF₃ | O | CH₃ | CH₂CH₂OCH₃ | |
| 1229 | — | O | C₂H₅ | (6-)CF₃ | O | CH₃ | CH₂CH₂OCH₃ | |
| 1230 | — | O | C₂H₅ | (6-)CF₃ | O | ▷ | CH=CHCH₃ | |
| 1231 | — | O | C₃H₇ | (6-)CF₃ | O | ▷ | CH=CHCH₃ | |
| 1232 | — | O | C₃H₇-i | (6-)CF₃ | O | CH₃ | CH₂CH₂OCH₃ | |
| 1233 | — | O | C₃H₇-i | (6-)CF₃ | O | ▷ | CH=CHCH₃ | |
| 1234 | — | S | CH₃ | (6-)CH₃ | O | ▷ | OC₃H₇-i | |
| 1235 | — | S | CH₃ | (6-)CH₃ | O | CH₃ | OCH₂CF₃ | |
| 1236 | — | S | CH₃ | (6-)CH₃ | O | CH₃ | OC₃H₇ | |
| 1237 | — | S | CH₃ | (6-)CH₃ | O | ▷ | OCH₃ | |
| 1238 | — | S | C₂H₅ | (6-)CH₃ | O | ▷ | OC₃H₇-i | |
| 1239 | — | S | C₂H₅ | (6-)CH₃ | O | CH₃ | OCH₂CF₃ | |
| 1240 | — | S | C₂H₅ | (6-)CH₃ | O | CH₃ | OC₃H₇ | |
| 1241 | — | S | C₂H₅ | (6-)CH₃ | O | ▷ | OCH₃ | |
| 1242 | — | S | C₂H₅ | (6-)CH₃ | O | ▷ | OCH₂CF₃ | |
| 1243 | — | S | CH₃ | (6-)CH₃ | O | ▷ | ▷ | |
| 1244 | — | S | C₂H₅ | (6-)CH₃ | O | ▷ | ▷ | |
| 1245 | — | S | C₃H₇ | (6-)CH₃ | O | ▷ | ▷ | |
| 1246 | — | S | C₃H₇-i | (6-)CH₃ | O | ▷ | ▷ | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1247 | — | O | CH₃ | (6-)CF₃ | O | △ | OCH₃ | |
| 1248 | — | O | CH₂CH₂F | (6-)CF₃ | O | CH₃ | OCH₃ | |
| 1249 | — | O | CH₂CH₂F | (6-)CF₃ | O | CH₃ | OC₂H₅ | |
| 1250 | — | O | CH₂CH₂F | (6-)CF₃ | O | △ | OC₂H₅ | |
| 1251 | — | O | CH₂CH₂F | (6-)CF₃ | O | CH₃ | OC₃H₇ | |
| 1252 | — | O | CH₂CH₂F | (6-)CF₃ | O | CH₃ | OC₃H₇-i | |
| 1253 | — | O | CH₂CH₂F | (6-)CF₃ | O | △ | OC₃H₇ | |
| 1254 | — | O | CH₂CH₂F | (6-)CF₃ | O | △ | OC₃H₇-i | |
| 1255 | — | O | CH₂CH₂F | (6-)CF₃ | O | △ | △ | |
| 1256 | — | O | CH₃ | (6-)C₂H₅ | O | CH₃ | CH₂OCH₃ | 124 |
| 1257 | — | O | CH₃ | (6-)C₂H₅ | O | CH₃ | OCH₂CF₃ | 156 |
| 1258 | — | O | CH₃ | (6-)C₂H₅ | O | CH₃ | SC≡CH | 147 |
| 1259 | — | O | CH₃ | (6-)C₂H₅ | O | CH₃ | CH(CH₃)₂ | 113 |
| 1260 | — | O | CH₃ | (6-)C₂H₅ | O | CH₃ | CH(CH₃)₂ | 125 |
| 1261 | — | O | CH₃ | (6-)C₂H₅ | O | △ | Br | 154 |
| 1262 | — | O | CH₃ | (6-)C₂H₅ | O | C₂H₅ | OC₂H₅ | >250 |
| 1263 | — | O | CH₃ | (6-)C₂H₅ | O | CH₃ | OC₃H₇ | 200 |
| 1264 | — | O | CH₃ | (6-)C₂H₅ | O | △ | OC₂H₅ | 178 |
| 1265 | — | O | CH₃ | (6-)Br | O | CH₃ | OC₂H₅ | 228 |
| 1266 | — | O | C₂H₅ | (6-)C₂H₅ | O | C₂H₅ | OC₂H₅ | |
| 1267 | — | O | C₂H₅ | (6-)C₂H₅ | O | CH₃ | OC₃H₇ | |
| 1268 | — | O | CH(CH₃)₂ | (6-)C₂H₅ | O | C₂H₅ | OC₂H₅ | |
| 1269 | — | O | CH(CH₃)₂ | (6-)C₂H₅ | O | CH₃ | OC₃H₇ | |
| 1270 | — | O | C₂H₅ | (6-)C₂H₅ | O | CH₃ | CH₂OCH₃ | |
| 1271 | — | O | C₂H₅ | (6-)C₂H₅ | O | CH₃ | OCH₂CF₃ | |
| 1272 | — | O | CH(CH₃)₂ | (6-)C₂H₅ | O | CH₃ | CH₂OCH₃ | |
| 1273 | — | O | CH(CH₃)₂ | (6-)C₂H₅ | O | CH₃ | OCH₂CF₃ | |
| 1274 | — | O | CF₃ | (6-)Br | O | CH₃ | OC₂H₅ | |
| 1275 | — | O | C₂H₅ | (6-)C₂H₅ | O | CH₃ | OCH(CH₃)₂ | |
| 1276 | — | O | C₂H₅ | (6-)C₂H₅ | O | △ | OC₂H₅ | |
| 1277 | — | O | C₂H₅ | (6-)C₂H₅ | O | △ | CH₂OCH₃ | |
| 1278 | — | O | CH(CH₃)₂ | (6-)C₂H₅ | O | CH₃ | OCH(CH₃)₂ | |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1279 | — | O | CH(CH₃)₂ | (6-)C₂H₅ | O |  | OC₂H₅ | |
| 1280 | — | O | CH(CH₃)₂ | (6-)C₂H₅ | O |  | CH₂OCH₃ | |
| 1281 | — | O | C₃H₇ | (6-)Br | O | CH₃ | OC₂H₅ | |
| 1282 | — | O | C₂H₅ | (6-)C₂H₅ | O | CH₃ | OCH₃ | |
| 1283 | — | O | C₂H₅ | (6-)F | O | CH₃ | OC₂H₅ | 165 |
| 1284 | — | O | CH₃ | (6-)F | O | CH₃ | OC₂H₅ | 211 |
| 1285 | — | O | CH₃ | (6-)CN | O | CH₃ | OC₂H₅ | 255 |
| 1286 | — | O | CH₃ | (6-)CN | O | CH₃ | OC₂H₅ | |
| 1287 | — | O | CH₃ | (6-)CN | O | CH₃ | C₂H₅ | 162 |
| 1288 | — | O | CH₃ | (6-)CN | O | CH₃ | SCH₃ | 268 |
| 1289 | — | O | CH₃ | (6-)CN | O | CH₃ | OCH₃ | 242 |
| 1290 | — | O | CH₃ | (6-)CH(CH₃)₂ | O | CH₃ | OCH₃ | 183 |
| 1291 | — | O | C₂H₅ | (6-)CH(CH₃)₂ | O | CH₃ | CH₃ | 283 |
| 1292 | — | O | C₂H₅ | (6-)CH(CH₃)₂ | O | CH₃ | OCH₃ | 227 |
| 1293 | — | O | CH₃ | (6-)F | O | CH₃ | OC₂H₅ | |
| 1294 | — | O | CH₃ | (6-)F | O | CH₃ | C₂H₅ | 156 |
| 1295 | — | O | CH₃ | (6-)F | O | CH₃ | SCH₃ | 179 |
| 1296 | — | O | CH₃ | (6-)F | O | CH₃ | CH₃ | 217 |
| 1297 | — | O | CH₃ | (6-)F | O |  | OCH(CH₃)₂ | 147 |
| 1298 | — | O | CH(CH₃)₂ | (6-)F | O | CH₃ | OC₂H₅ | 165 |
| 1299 | — | O | CH(CH₃)₂ | (6-)F | O | CH₃ | C₂H₅ | 113 |
| 1300 | — | O | CH(CH₃)₂ | (6-)F | O | CH₃ | OCH₃ | 149 |
| 1301 | — | O | CH(CH₃)₂ | (6-)F | O |  | CH₃ | 147 |
| 1302 | — | O | CH(CH₃)₂ | (6-)F | O |  | OCH(CH₃)₂ | 127 |
| 1303 | — | O | C₃H₇ | (6-)F | O | CH₃ | OC₂H₅ | 139 |
| 1304 | — | O | C₃H₇ | (6-)F | O | CH₃ | C₂H₅ | 116 |
| 1305 | — | O | C₃H₇ | (6-)F | O | CH₃ | OCH₃ | 129 |
| 1306 | — | O | C₃H₇ | (6-)F | O |  | CH₃ | 120 |
| 1307 | — | O | C₃H₇ | (6-)F | O | CH₃ | OC₂H₅ | >160 |
| 1308 | — | O | C₂H₅ | (6-)CH₃ | O | CH₃ | OC₄H₉ | 114 |
| 1309 | — | O | C₂H₅ | (6-)CH₃ | O | | OC₄H₉ | 126 |
| 1310 | — | O | C₂H₅ | (6-)CH₃ | O | CH₃ | OCH₂CH(CH₃)₂ | 144 |
| 1311 | — | O | C₂H₅ | (6-)CH₃ | O |  | OCH₂CH(CH₃)₂ | 145 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1312 | — | O | C₂H₅ | (6-)CH₃ | O | cyclopropyl | OCH₂CF₃ | 133 |
| 1313 | — | O | C₂H₅ | (6-)CH₃ | O | cyclopropyl | OCH₃ | 181 |
| 1314 | — | O | C₂H₅ | (6-)CH(CH₃)₂ | O | CH₃ | OC₄H₉ | 170 |
| 1315 | — | O | C₂H₅ | (6-)CH(CH₃)₂ | O | cyclopropyl | OC₄H₉ | 129 |
| 1316 | — | O | CH₃ | (6-)CH₃ | O | CH₃ | OCH₂CH(CH₃)₂ | 137 |
| 1317 | — | O | CH₃ | (6-)CH₃ | O | cyclopropyl | OCH₂CH(CH₃)₂ | 165 |
| 1318 | — | O | CH₃ | (6-)CH₃ | O | CH₃ | cyclopropyl | 150 |
| 1319 | — | O | CH₃ | (6-)CH₃ | O | cyclopropyl | cyclopropyl | 186 |
| 1320 | — | O | C₂H₅ | (6-)CH(CH₃)₂ | O | CH₃ | OCH₂CH(CH₃)₂ | 163 |
| 1321 | — | O | C₂H₅ | (6-)CH(CH₃)₂ | O | CH₃ | cyclopropyl | 134 |
| 1322 | — | O | C₂H₅ | (6-)CH(CH₃)₂ | O | cyclopropyl | cyclopropyl | 187 |
| 1323 | — | O | C₂H₅ | (6-)CH(CH₃)₂ | O | cyclopropyl | CH₃ | 158 |
| 1324 | — | O | C₂H₅ | (6-)CH(CH₃)₂ | O | cyclopropyl | C₂H₅ | 172 |
| 1325 | — | O | C₂H₅ | (6-)CH(CH₃)₂ | O | cyclopropyl | C₃H₇ | 142 |
| 1326 | — | O | C₂H₅ | (6-)CH(CH₃)₂ | O | cyclopropyl | OCH₂CF₃ | 150 |
| 1327 | — | O | C₂H₅ | (6-)CH(CH₃)₂ | O | cyclopropyl | OCH₃ | 137 |
| 1328 | — | O | C₂H₅ | (6-)CH(CH₃)₂ | O | cyclopropyl | CH(C₂H₃)₂ | 168 |
| 1329 | — | O | C₂H₅ | (6-)CH₃ | O | cyclopropyl | SCH₃ | 167 |

TABLE 1A-continued

Examples of the compounds of the formula (IA)

(IA)

| Ex. No. | A | Q | R¹ | (Position-) R² | Q¹ | R⁴ | R⁵ | Melting point °C. |
|---|---|---|---|---|---|---|---|---|
| 1330 | — | O | CH(CH₃)₂ | (6-)CH₃ | O |  | SCH₃ | 167 |
| 1331 | — | O | C₂H₅ | (6-)CH₃ | O |  | SC₂H₅ | 150 |
| 1332 | — | O | CH(CH₃)₂ | (6-)CH₃ | O |  | SC₂H₅ | 150 |
| 1333 | — | O | C₃H₇ | (6-)CH₃ | O |  | SC₂H₅ | 140 |
| 1334 | — | O | C₂H₅ | (6-)F | O | CH₃ | SCH₃ | 165 |
| 1335 | — | O | C₂H₅ | (6-)F | O | CH₃ | C₂H₅ | 135 |
| 1336 | — | O | C₂H₅ | (6-)F | O | CH₃ | OCH₃ | 168 |
| 1337 | — | O | C₂H₅ | (6-)F | O | CH₃ | CH₃ | 140 |
| 1338 | — | O | C₂H₅ | (6-)F | O |  | OCH₃ | 138 |
| 1339 | — | O | C₃H₇ | (6-)OC₃H₇ | O | CH₃ | OC₂H₅ | |
| 1340 | — | O | C₃H₇ | (6-)OC₃H₇ | O | CH₃ | OC₂H₅ | |
| 1341 | — | O | C₃H₇ | (6-)OCH₃ | O | CH₃ | OC₂H₅ | |
| 1342 | — | O | CH(CH₃)₂ | (6-)OCH(CH₃)₂ | O | CH₃ | OC₂H₅ | |
| 1343 | — | O | C₂H₅ | (6-)OC₂H₅ | O | CH₃ | OC₂H₅ | |
| 1344 | — | O | C₄H₉ | (6-)OC₄H₉ | O | CH₃ | OC₂H₅ | |
| 1345 | — | O | CH(CH₃)C₂H₅ | (6-)OCH₃ | O | CH₃ | CH₃ | 157 |
| 1346 | — | O | CH(CH₃)C₂H₅ | (6-)OCH₃ | O | CH₃ | C₃H₇ | 86 |
| 1347 | — | O | CH₂CH(CH₃)₂ | (6-)OC₂H₅ | O | CH₃ | Br | 108 |
| 1348 | — | O | CH₂CH(CH₃)₂ | (6-)OC₂H₅ | O | CH₃ | CH₃ | 82 |
| 1349 | — | O | CH₂CH(CH₃)₂ | (6-)OC₂H₅ | O |  | Br | 120 |
| 1350 | — | O | C₃H₇ | (6-)OCH₃ | O |  | OCH(CH₃)₂ | 141 |
| 1351 | — | O | C₃H₇ | (6-)OCH₃ | O |  | OC₃H₇ | 102 |
| 1352 | — | O | C₂H₅ | (6-)OC₂H₅ | O |  | OCH(CH₃)₂ | 110 |
| 1353 | — | O | C₂H₅ | (6-)OC₂H₅ | O |  | OC₃H₇ | 132 |
| 1354 | — | O | C₂H₅ | (6-)OC₂H₅ | O |  | OCH₂CF₃ | 114 |
| 1355 | — | O | CH(CH₃)₂ | (6-)OCH₃ | O |  | OCH(CH₃)₂ | 172 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1356 | — | O | CH(CH₃)₂ | (6-)OCH₃ | O |  | OC₃H₇ | 156 |
| 1357 | — | O | C₃H₇ | (6-)OC₃H₇ | O |  | OCH(CH₃)₂ | 141 |
| 1358 | — | O | C₂H₅ | (6-)OCH₃ | O |  | OC₃H₇ | 134 |
| 1359 | — | O | C₂H₅ | (6-)OC₃H₇ | O |  | OCH(CH₃)₂ | 132 |
| 1360 | — | O | CH(CH₃)₂ | (6-)OC₂H₅ | O |  | OCH(CH₃)₂ | 147 |
| 1361 | — | O | (CH₂)₂OC₃H₇ | (6-)OCH₃ | O |  | OCH₂CF₃ | 134 |
| 1362 | — | O | CH₂CH(CH₃)₂ | (6-)OC₂H₅ | O |  | OCH(CH₃)₂ | 96 |
| 1363 | — | O | C₃H₇ | (6-)OC₂H₅ | O |  | OCH₃ | 120 |
| 1364 | — | O | CH(CH₃)₂ | (6-)OC₂H₅ | O |  | OCH₃ | 108 |
| 1365 | — | O | CH(CH₃)₂ | (6-)OC₂H₅ | O |  | OC₃H₇ | 127 |
| 1366 | — | O | C₄H₉ | (6-)OC₄H₉ | O |  | OCH₃ | 118 |
| 1367 | — | O | CH(CH₃)₂ | (6-)OCH(CH₃)₂ | O |  |  | 154 |
| 1368 | — | O | C₃H₇ | (6-)OCH₃ | O |  | CH₃ | 122 |
| 1369 | — | O | CH(CH₃)₂ | (6-)OCH(CH₃)₂ | O |  | CH₃ | 134 |
| 1370 | — | O | CH(CH₃)₂ | (6-)OCH(CH₃)₂ | O | CH₃ | CH(CH₃)C₂H₅ | 97 |
| 1371 | — | O | C₃H₇ | (6-)OCH₃ | O | CH₃ | CH(CH₃)₂ | 76 |
| 1372 | — | O | C₃H₇ | (6-)OCH₃ | O | CH₃ | SC₂H₅ | 91 |
| 1373 | — | O | C₂H₅ | (6-)OC₂H₅ | O |  | | 102 |
| 1374 | — | O | C₂H₅ | (6-)OC₂H₅ | O |  | CH₃ | 125 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1375 | — | O | $C_2H_5$ | (6-)$OC_2H_5$ | O | —$CH_2$— | $C_2H_5$ | 112 |
| 1376 | — | O | $C_2H_5$ | (6-)$OC_2H_5$ | O | —$CH_2$— | $C_3H_7$ | 113 |
| 1377 | — | O | $C_2H_5$ | (6-)$OC_2H_5$ | O | $CH_3$ | $CH(CH_3)C_2H_5$ | 100 |
| 1378 | — | O | $C_2H_5$ | (6-)$OC_2H_5$ | O | $CH_3$ | $CH(CH_3)_2$ | 118 |
| 1379 | — | O | $C_2H_5$ | (6-)$OC_2H_5$ | O | $CH_3$ | $C_4H_9$ | 81 |
| 1380 | — | O | $C_2H_5$ | (6-)$OC_2H_5$ | O | $CH_3$ | $CH_2CH(CH_3)_2$ | 93 |
| 1381 | — | O | $C_3H_7$ | (6-)$OCH_3$ | O | $CH_3$ | $CH(CH_3)C_2H_5$ | 79 |
| 1382 | — | O | $C_3H_7$ | (6-)$OCH_3$ | O | $CH_3$ | $CH_2CH(CH_3)_2$ | 83 |
| 1383 | — | O | $C_2H_5$ | (6-)$OC_2H_5$ | O | —$CH_2$— | $OC_2H_5$ | 67 |
| 1384 | — | O | $C_2H_5$ | (6-)$OC_2H_5$ | O |  | $C_3H_7$ | 105 |
| 1385 | — | O | $C_2H_5$ | (6-)$OC_2H_5$ | O | —$CH_2$— | $OCH(CH_3)_2$ | 97 |
| 1386 | — | O | $C_3H_7$ | (6-)$OCH_3$ | O | —$CH_2$— | $OCH(CH_3)_2$ | 82 |
| 1387 | — | O | $C_2H_5$ | (6-)$OC_2H_5$ | O |  | $CH_2CH(CH_3)_2$ | 103 |
| 1388 | — | O | $C_3H_7$ | (6-)$OCH_3$ | O |  | $CH_2CH(CH_3)_2$ | 116 |
| 1389 | — | O | $C_2H_5$ | (6-)$OC_2H_5$ | O | —$CH_2$— | $OCH_3$ | 104 |
| 1390 | — | O | $CH(CH_3)_2$ | (6-)$OCH(CH_3)_2$ | O | —$CH_2$— | $OCH_3$ | 127 |
| 1391 | — | O | $C_3H_7$ | (6-)$OCH_3$ | O | —$CH_2$— | $OCH_3$ | 93 |
| 1392 | — | O | $C_2H_5$ | (6-)$OC_2H_5$ | O | —$CH_2$— | $OC_3H_7$ | 107 |
| 1393 | — | O | $CH(CH_3)_2$ | (6-)$OCH(CH_3)_2$ | O | —$CH_2$— | $OC_3H_7$ | 130 |
| 1394 | — | O | $C_3H_7$ | (6-)$OCH_3$ | O | —$CH_2$— | $OC_3H_7$ | 80 |
| 1395 | — | O | $C_2H_5$ | (6-)$OC_2H_5$ | O |  | $C_4H_9$ | 77 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1396 | — | O | $C_3H_7$ | (6-)$CH_3$ | O | cyclopropyl | $C_4H_9$ | 107 |
| 1397 | — | O | $C_2H_5$ | (6-)$OC_2H_5$ | O | $-CH_2-$cyclopropyl | $O-CH_2-$cyclopropyl | 107 |
| 1398 | — | O | $C_3H_7$ | (6-)$OCH_3$ | O | $-CH_2-$cyclopropyl | $O-CH_2-$cyclopropyl | 85 |
| 1399 | — | O | $CH(CH_3)_2$ | (6-)$OCH(CH_3)_2$ | O | cyclopropyl | $C_4H_9$ | 89 |
| 1400 | — | O | $CH(CH_3)_2$ | (6-)$OCH(CH_3)_2$ | O | $-CH_2-$cyclopropyl | $O-CH_2-$cyclopropyl | 100 |
| 1401 | — | O | $CH(CH_3)_2$ | (6-)$OCH(CH_3)_2$ | O | $CH_3$ | $CH(CH_3)_2$ | 118 |
| 1402 | — | O | $CH(CH_3)_2$ | (6-)$OCH(CH_3)_2$ | O | $CH_3$ | $C_4H_9$ | 82 |
| 1403 | — | O | $C_3H_7$ | (6-)$OCH_3$ | O | $CH_3$ | $C_4H_9$ | 75 |
| 1404 | — | O | $CH(CH_3)_2$ | (6-)$OCH(CH_3)_2$ | O | cyclopropyl | $CH_2CH(CH_3)_2$ | 95 |
| 1405 | — | O | $C_2H_5$ | (6-)$OC_2H_5$ | O | $CH_3$ | $C(CH_3)=CH_2$ | 118 |
| 1406 | — | O | $CH(CH_3)_2$ | (6-)$OCH(CH_3)_2$ | O | $CH_3$ | $C(CH_3)=CH_2$ | 103 |
| 1407 | — | O | $C_3H_7$ | (6-)$OCH_3$ | O | $CH_3$ | $C(CH_3)=CH_2$ | 92 |
| 1408 | — | O | $C_3H_7$ | (6-)OH | O | $CH_3$ | $OC_2H_5$ | 152 |
| 1409 | — | O | $C_3H_7$ | (6-)OH | O | $CH_3$ | $OCH_3$ | 137 |
| 1410 | — | O | $C_3H_7$ | (6-)OH | O | $CH_3$ | $OC_3H_7$ | 88 |
| 1411 | — | O | $C_3H_7$ | (6-)OH | O | $CH_3$ | $OCH(CH_3)_2$ | 125 |
| 1412 | — | O | $CH_3$ | (6-)OH | O | $CH_3$ | $OCH_3$ | 148 |
| 1413 | — | O | $CH_3$ | (6-)OH | O | $CH_3$ | $OC_2H_5$ | 144 |
| 1414 | — | O | $CH_3$ | (6-)OH | O | $CH_3$ | $OC_3H_7$ | 128 |
| 1415 | — | O | $CH_3$ | (6-)OH | O | $CH_3$ | $OCH(CH_3)_2$ | 158 |
| 1416 | — | O | $CH_3$ | (6-)OH | O | cyclopropyl | $OCH(CH_3)_2$ | 137 |
| 1417 | — | O | $CH_3$ | (6-)OH | O | cyclopropyl | $OC_2H_5$ | 125 |
| 1418 | — | O | $CH_3$ | (6-)OH | O | $C_2H_5$ | $OCH_3$ | 137 |
| 1419 | — | O | $CH_3$ | (6-)OH | O | $CH_3$ | $SCH_3$ | 130 |
| 1420 | — | O | $CH_3$ | (6-)OH | O | $CH_3$ | $C_2H_5$ | 40 |
| 1421 | — | O | $C_3H_7$ | (6-)$OCHF_2$ | O | $CH_3$ | $OC_2H_5$ | 230 |
| 1422 | — | O | $CH_3$ | (6-)$OCHF_2$ | O | $CH_3$ | $OC_2H_5$ | 202 |
| 1423 | — | O | $CH_3$ | (6-)$OCHF_2$ | O | $CH_3$ | $SCH_3$ | 202 |
| 1424 | — | O | $CH_3$ | (6-)$OCHF_2$ | O | $CH_3$ | $C_2H_5$ | 98 |
| 1425 | — | S | $C_3H_7$ | (6-)$OCHF_2$ | O | $CH_3$ | $OC_3H_7$ | 198 |
| 1426 | — | O | $C_3H_7$ | (6-)$OCHF_2$ | O | cyclopropyl | $OC_2H_5$ | 124 |
| 1427 | — | O | $CHF_2$ | (6-)$OCHF_2$ | O | $CH_3$ | $OCH_3$ | 145 |
| 1428 | — | O | $CHF_2$ | (6-)$OCHF_2$ | O | $CH_3$ | $OC_2H_5$ | 177 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1429 | — | O | CHF₂ | (6-)OCHF₂ | O | CH₃ | OC₂H₅ | >220 |
| 1430 | — | O | CHF₂ | (6-)OCHF₂ | O |  | OC₂H₅ | 148 |
| 1431 | — | O | CHF₂ | (6-)OCHF₂ | O | CH₃ | C₂H₅ | 123 |
| 1432 | — | O | CHF₂ | (6-)OCHF₂ | O | CH₃ | SCH₃ | 133 |
| 1433 | — | O | CHF₂ | (6-)OCHF₂ | O |  | CH(CH₃)₂ | 130 |
| 1434 | — | O | C₃H₇ | (6-)OCHF₂ | O | CH₃ | OCH(CH₃)₂ | |
| 1435 | — | O | CH₂CH=CH₂ | (6-)OC₂H₅ | O |  | OC₂H₅ | 84 |
| 1436 | — | O | CH₂CH=CH₂ | (6-)OC₂H₅ | O | 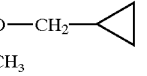 | OCH₃ | 120 |
| 1437 | — | O | CH₂CH=CH₂ | (6-)OC₂H₅ | O | CH₃ | OCH(CH₃)₂ | 133 |
| 1438 | — | O | CH₂CH=CH₂ | (6-)OC₂H₅ | O | CH₃ | C₂H₅ | 137 |
| 1439 | — | O | CH₂CH=CH₂ | (6-)OC₂H₅ | O | CH₃ | OC₂H₅ | 100 |
| 1440 | — | O | CH₂CH=CH₂ | (6-)OC₂H₅ | O | CH₃ | OCH₃ | 94 |
| 1441 | — | O | CH₃ | (6-)OCH₃ | O | CH₃ | N(CH₃)₂ | 168 |
| 1442 | — | O | CH₃ | (6-)C₂H₅ | O | CH₃ | N(CH₃)₂ | 172 |
| 1443 | — | O | CF₃ | (6-)C₂H₅ | O | CH₃ | N(CH₃)₂ | 128 |
| 1444 | — | O | CF₃ | (6-)CH₃ | O | CH₃ | OC₂H₅ | 224 |
| 1445 | — | O | CH₃ | (6-)OCH₃ | O | OCH₃ | SCH₃ | 157 |
| 1446 | — | O | CH₃ | (6-)OCH₃ | O | OCH₃ | SC₂H₅ | 149 |
| 1447 | — | O | CH₃ | (6-)OCH₃ | O | OC₂H₅ | SCH₃ | 147 |
| 1448 | — | O | CH₃ | (6-)OCH₃ | O | OC₂H₅ | SC₂H₅ | 124 |
| 1449 | — | O | CH₃ | (6-)C₂H₅ | O | NH₂ | CH₃ | 204 |
| 1450 | — | O | C₂H₅ | (6-)OC₂H₅ | O | OCH₃ | SCH₃ | 130 |
| 1451 | — | O | C₂H₅ | (6-)OC₂H₅ | O | OCH₃ | SC₂H₅ | 112 |
| 1452 | — | O | C₂H₅ | (6-)OC₂H₅ | O | OC₂H₅ | SCH₃ | 113 |
| 1453 | — | O | OC₂H₅ | (6-)OC₂H₅ | O | OC₂H₅ | SC₂H₅ | 157 |
| 1454 | — | O | CF₂CF₂H | (6-)CH₃ | O | CH₃ | OCH₃ | 127 |
| 1455 | — | O | CF₂CF₂H | (6-)CH₃ | O | CH₃ | OC₂H₅ | 156 |
| 1456 | — | O | CF₂CF₂H | (6-)CH₃ | O | CH₃ | OC₃H₇ | 132 |
| 1457 | — | O | CF₂CF₂H | (6-)CH₃ | O | CH₃ | OCH(CH₃)₂ | 172 |
| 1458 | — | O | CF₂CF₂H | (6-)CH₃ | O | CH₃ | C₃H₇ | 90 |
| 1459 | — | O | CF₃ | (6-)C₂H₅ | O | CH₃ | OC₃H₇ | 185 |
| 1460 | — | O | CF₃ | (6-)C₂H₅ | O | CH₃ | OCH(CH₃)₂ | 192 |
| 1461 | — | O | CF₃ | (6-)C₂H₅ | O | CH₃ | OCH₂CF₃ | 159 |
| 1462 | — | O | CF₃ | (6-)C₂H₅ | O | CH₃ | O—CH₂— | 192 |
| 1463 | — | O | CF₃ | (6-)C₂H₅ | O | CH₃ | CH₃ | >270 |
| 1464 | — | O | CF₃ | (6-)C₂H₅ | O | CH₃ | C₂H₅ | 259 |
| 1465 | — | O | CF₃ | (6-)C₂H₅ | O | CH₃ | C₃H₇ | 241 |
| 1466 | — | O | CF₃ | (6-)C₂H₅ | O | CH₃ | SCH₃ | 174 |
| 1467 | — | O | CF₃ | (6-)C₂H₅ | O |  | OCH₃ | 165 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1468 | — | O | CF₃ | (6-)C₂H₅ | O |  | OC₂H₅ | 145 |
| 1469 | — | O | CF₃ | (6-)C₂H₅ | O |  | OC₃H₇ | 196 |
| 1470 | — | O | CF₃ | (6-)C₂H₅ | O |  | OCH(CH₃)₂ | 170 |
| 1471 | — | O | CF₃ | (6-)C₂H₅ | O |  | OCH₂CF₃ | 183 |
| 1472 | — | O | CF₃ | (6-)C₂H₅ | O |  | O—CH₂— | 154 |
| 1473 | — | O | CF₃ | (6-)C₂H₅ | O | CH₃ |  | 188 |
| 1474 | — | O | CF₃ | (6-)C₂H₅ | O |  | C₂H₅ | 163 |
| 1475 | — | O | CF₃ | (6-)C₂H₅ | O |  | C₃H₇ | 190 |
| 1476 | — | O | CF₃ | (6-)C₂H₅ | O |  | SCH₃ | 159 |
| 1477 | — | O | CF₃ | (6-)C₂H₅ | O |  | CH₃ | 151 |
| 1478 | — | O | CF₃ | (6-)C₂H₅ | O |  | C₃H₇ | 163 |
| 1479 | — | O | CF₃ | (6-)C₂H₅ | O |  | CH=CH(CH₃) | 176 |
| 1480 | — | O | CF₃ | (6-)C₂H₅ | O |  |  | 156 |
| 1481 | — | O | CF₃ | (6-)C₂H₅ | O |  | CH₂OCH₃ | 146 |
| 1482 | — | O | CH₃ | (6-)C₂H₅ | O | OCH₃ | SCH₃ | 149 |
| 1483 | — | O | CH₃ | (6-)C₂H₅ | O | OCH₃ | SC₂H₅ | 137 |
| 1484 | — | O | CH₃ | (6-)C₂H₅ | O | OC₂H₅ | SCH₃ | 115 |
| 1485 | — | O | CH₃ | (6-)C₂H₅ | O | OC₂H₅ | SC₂H₅ | 99 |
| 1486 | — | O | CH(CH₃)₂ | (6-)CH₃ | O |  | CH(CH₃)₂ | 132 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1487 | — | O | $CF_3$ | (6-)$C_2H_5$ | O |  | $CH(CH_3)_2$ | 108 |
| 1488 | — | O | $CH_3$ | (6-)$C_2H_5$ | O |  | $CH(CH_3)_2$ | 151 |
| 1489 | — | O | $CH_3$ | (6-)$OCH_3$ | O |  | $CH(CH_3)_2$ | 163 |
| 1490 | — | O | $C_2H_5$ | (6-)$OC_2H_5$ | O |  | $CH(CH_3)_2$ | 111 |
| 1491 | — | O | $CH_3$ | (6-)$C_2H_5$ | O | $CH_3$ |  | 118 |
| 1492 | — | O | $CH_3$ | (6-)$C_2H_5$ | O |  |  | 147 |
| 1493 | — | O | $CF_3CF_3H$ | (6-)$CH_3$ | O |  | $OCH_3$ | 160 |
| 1494 | — | O | $CF_3CF_3H$ | (6-)$CH_3$ | O | 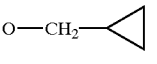 | $OC_2H_5$ | 155 |
| 1495 | — | O | $CF_3CF_3H$ | (6-)$CH_3$ | O |  | $OCH(CH_3)_2$ | 166 |
| 1496 | — | O | $CH_2CF_3$ | (6-)$CH_3$ | O | $CH_3$ | $OCH_3$ | 149 |
| 1497 | — | O | $CH_2CF_3$ | (6-)$CH_3$ | O | $CH_3$ | $OC_2H_5$ | 230 |
| 1498 | — | O | $CH_2CF_3$ | (6-)$CH_3$ | O | $CH_3$ | $OC_3H_7$ | 238 |
| 1499 | — | O | $CH_2CF_3$ | (6-)$CH_3$ | O | $CH_3$ | $OCH(CH_3)_2$ | 89 |
| 1500 | — | O | $CH_2CF_3$ | (6-)$CH_3$ | O | $CH_3$ |  | 134 |
| 1501 | — | O | $CH_2CF_3$ | (6-)$CH_3$ | O |  | $OCH_3$ | 189 |
| 1502 | — | O | $CH_2CF_3$ | (6-)$CH_3$ | O |  | $OC_2H_5$ | 129 |
| 1503 | — | O | $CH_2CF_3$ | (6-)$CH_3$ | O | 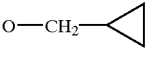 | $OC_3H_7$ | 126 |
| 1504 | — | O | $CH_2CF_3$ | (6-)$CH_3$ | O |  | $OCH(CH_3)_2$ | 161 |
| 1505 | — | O | $CH_2CF_3$ | (6-)$CH_3$ | O | | | 128 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1506 | — | O | CH₂CF₃ | (6-)CH₃ | O | CH₃ | C₃H₇ | 148 |
| 1507 | — | O | CH₃ | (6-)C₂H₅ | O | CH₃ |  | 144 |
| 1508 | — | O | CH₃ | (6-)C₂H₅ | O | CH₃ | CH=CH(CH₃) | 138 |
| 1509 | — | O | CH₃ | (6-)C₂H₅ | O | CH₃ |  | 160 |
| 1510 | — | O | CH₃ | (6-)C₂H₅ | O |  | CH₃ | 168 |
| 1511 | — | O | CH₃ | (6-)C₂H₅ | O |  | C₂H₅ | 143 |
| 1512 | — | O | CH₃ | (6-)C₂H₅ | O |  | C₃H₇ | 140 |
| 1513 | — | O | CH₃ | (6-)C₂H₅ | O |  |  | 170 |
| 1514 | — | O | CH₃ | (6-)C₂H₅ | O |  | CH=CH(CH₃) | 127 |
| 1515 | — | O | CH₃ | (6-)C₂H₅ | O |  | N(CH₃)₂ | 214 |
| 1516 | — | O | CH₃ | (6-)C₂H₅ | O |  | SCH₃ | 167 |
| 1517 | — | O | CH₃ | (6-)C₂H₅ | O |  | SC₂H₅ | 137 |
| 1518 | — | O | CH₃ | (6-)C₂H₅ | O |  | OCH₃ | 165 |
| 1519 | — | O | CH₃ | (6-)C₂H₅ | O |  | OCH₂CF₃ | 163 |
| 1520 | — | O | CH₃ | (6-)C₂H₅ | O |  | OC₃H₇ | 125 |
| 1521 | — | O | CH₃ | (6-)C₂H₅ | O |  | 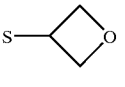 | 133 |
| 1522 | — | O | CH₃ | (6-)C₂H₅ | O | CH₃ | (S-oxetane) | 136 |
| 1523 | — | O | CF₂H | (6-)C₂H₅ | O | CH₃ | OCH₃ | 121 |
| 1524 | — | O | CF₂H | (6-)C₂H₅ | O | CH₃ | OC₂H₅ | 150 |

TABLE 1A-continued

Examples of the compounds of the formula (IA)

(IA)

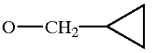

| Ex. No. | A | Q | R¹ | (Position-) R² | Q¹ | R⁴ | R⁵ | Melting point ° C. |
|---|---|---|---|---|---|---|---|---|
| 1525 | — | O | CF₂H | (6-)C₂H₅ | O | CH₃ | OC₃H₇ | 119 |
| 1526 | — | O | CF₂H | (6-)C₂H₅ | O | CH₃ | OCH(CH₃)₂ | 122 |
| 1527 | — | O | CF₂H | (6-)C₂H₅ | O | CH₃ |  | 146 |
| 1528 | — | O | CF₂H | (6-)C₂H₅ | O |  | OCH₃ | 163 |
| 1529 | — | O | CF₂H | (6-)C₂H₅ | O |  | OC₂H₅ | 140 |
| 1530 | — | O | CF₂H | (6-)C₂H₅ | O |  | OC₃H₇ | 129 |
| 1531 | — | O | CF₂H | (6-)C₂H₅ | O |  | OCH(CH₃)₂ | 118 |
| 1532 | — | O | CF₂H | (6-)C₂H₅ | O | 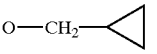 | 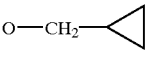 | 133 |
| 1533 | — | O | CH₂CH₂F | (6-)C₂H₅ | O | CH₃ | CH₃ | 290 |
| 1534 | — | O | CH₂CH₂F | (6-)C₂H₅ | O | CH₃ | C₃H₇ | 274 |
| 1535 | — | O | CH₂CH₂F | (6-)C₂H₅ | O | OC₂H₅ | C₂H₅ | 118 |
| 1536 | — | O | CH₂CH₂F | (6-)C₂H₅ | O | CH₃ | N(CH₃)₂ | 170 |
| 1537 | — | O | CH₂CH₂F | (6-)C₂H₅ | O | CH₃ | SCH₃ | 168 |
| 1538 | — | O | CH₂CH₂F | (6-)C₂H₅ | O | CH₃ | OCH₃ | 166 |
| 1539 | — | O | CH₂CH₂F | (6-)C₂H₅ | O | CH₃ | OC₂H₅ | 140 |
| 1540 | — | O | CH₂CH₂F | (6-)C₂H₅ | O | CH₃ | OC₃H₇ | 138 |
| 1541 | — | O | CH₂CH₂F | (6-)C₂H₅ | O | CH₃ | OCH(CH₃)₂ | 136 |
| 1542 | — | O | CH₂CH₂F | (6-)C₂H₅ | O | CH₃ |  | 139 |
| 1543 | — | O | CH₂CH₂F | (6-)C₂H₅ | O |  | OCH₃ | 156 |
| 1544 | — | O | CH₂CH₂F | (6-)C₂H₅ | O |  | OC₂H₅ | 138 |
| 1545 | — | O | CH₂CH₂F | (6-)C₂H₅ | O |  | OC₃H₇ | 125 |
| 1546 | — | O | CH₂CH₂F | (6-)C₂H₅ | O |  | OCH(CH₃)₂ | 140 |
| 1547 | — | O | CH₂CH₂F | (6-)C₂H₅ | O | 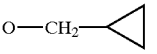 |  | 158 |
| 1548 | — | O | CH₃ | (6-)C₂H₅ | O | | C₅H₉ | 149 |
| 1549 | — | O | CH₃ | (6-)C₂H₅ | O | CH₃ | C₅H₉ | 118 |

TABLE 1A-continued

Examples of the compounds of the formula (IA)

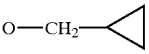

(IA)

| Ex. No. | A | Q | R¹ | (Position-)R² | Q¹ | R⁴ | R⁵ | Melting point °C. |
|---|---|---|---|---|---|---|---|---|
| 1550 | — | O | CF₃ | (6-)C₃H₇ | O | CH₃ | OCH₃ | 94 |
| 1551 | — | O | CF₃ | (6-)C₃H₇ | O | CH₃ | OC₂H₅ | 175 |
| 1552 | — | O | CF₃ | (6-)C₃H₇ | O | CH₃ | OC₃H₇ | 166 |
| 1553 | — | O | CF₃ | (6-)C₃H₇ | O | CH₃ | OCH(CH₃)₂ | 164 |
| 1554 | — | O | CF₃ | (6-)C₃H₇ | O | CH₃ | OCH₂CF₃ | 221 |
| 1555 | — | O | CF₃ | (6-)C₃H₇ | O | CH₃ | O—CH₂— | 189 |
| 1556 | — | O | CF₃ | (6-)C₃H₇ | O |  | OCH₃ | 182 |
| 1557 | — | O | CF₃ | (6-)C₃H₇ | O |  | OCH₂CH₃ | 134 |
| 1558 | — | O | CF₃ | (6-)C₃H₇ | O |  | OC₃H₇ | 207 |
| 1559 | — | O | CF₃ | (6-)C₃H₇ | O |  | OCH(CH₃)₂ | 148 |
| 1560 | — | O | CF₃ | (6-)C₃H₇ | O |  | OCH₂CF₃ | 204 |
| 1561 | — | O | CF₃ | (6-)C₃H₇ | O | 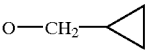 | O—CH₂— | 186 |
| 1562 | — | O | CH₃ | (6-)C₂H₅ | O | CH₂CH₂OCH₂ | | 163 |
| 1563 | — | O | CH₃ | (6-)C₂H₅ | O | CH₂CH₂CH₂OCH₂ | | 191 |
| 1564 | — | O | CF₃ | (6-)CH₃ | O |  | OCH₃ | 197 |
| 1565 | — | O | CH₂CF₂H | (6-)CH₃ | O | CH₃ | OCH₃ | 231 |
| 1566 | — | O | CH₂CF₂H | (6-)C₂H₅ | O | CH₃ | OCH₃ | 174 |
| 1567 | — | O | CH₂CF₂H | (6-)C₂H₅ | O |  | OCH₃ | 160 |
| 1568 | — | O | CH₂CF₂H | (6-)C₂H₅ | O | 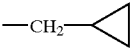 | OCH(CH₃)₂ | 162 |
| 1569 | — | O | CH₂CF₂H | (6-)C₂H₅ | O | CH₃ | CH₃ | >250 |
| 1570 | — | O | CH₂CF₂H | (6-)CH₃ | O | CH₃ | OCH₂CF₃ | 117 |
| 1571 | — | O | CH₂CF₂H | (6-)CH₃ | O | CH₃ | O—CH₂— | 128 |
| 1572 | — | O | CH₂CF₂H | (6-)CH₃ | O | 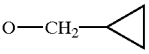 | O—CH₂— | 124 |
| 1573 | — | O | CH₂CF₂H | (6-)CH₃ | O | CH₃ | C₂H₅ | 137 |
| 1574 | — | O | CH₂CF₂H | (6-)CH₃ | O | CH₃ | C₃H₇ | 139 |

TABLE 1A-continued

Examples of the compounds of the formula (IA)

(IA)

| Ex. No. | A | Q | R¹ | (Position-) R² | Q¹ | R⁴ | R⁵ | Melting point ° C. |
|---|---|---|---|---|---|---|---|---|
| 1575 | — | O | CH₂CF₂H | (6-)CH₃ | O | CH₃ | ▷ | 150 |
| 1576 | — | O | CH₂CF₂H | (6-)CH₃ | O | CH₃ | CH₂OCH₃ | 114 |
| 1577 | — | O | CH₂CF₂H | (6-)CH₃ | O | CH₃ | SCH₃ | 155 |
| 1578 | — | O | CH₂CF₂H | (6-)C₃H₇ | O | CH₃ | CH₃ | 290 |
| 1579 | — | O | CH₂CF₂H | (6-)CH₃ | O | CH₃ | N(CH₃)₂ | 116 |
| 1580 | — | O | CH₂CF₂H | (6-)CH₃ | O | OC₂H₅ | C₂H₅ | 125 |
| 1581 | — | O | CH₂CF₂H | (6-)CH₃ | O | ▷ | CH₃ | 137 |
| 1582 | — | O | CH₂CF₂H | (6-)CH₃ | O | ▷ | OC₂H₅ | 99 |
| 1583 | — | O | CH₂CF₂H | (6-)CH₃ | O | ▷ | OC₃H₇ | 130 |
| 1584 | — | O | CH₂CF₂H | (6-)C₂H₅ | O | CH₃ | OC₂H₅ | 147 |
| 1585 | — | O | CH₂CF₂H | (6-)C₂H₅ | O | CH₃ | OCH(CH₃)₂ | 151 |
| 1586 | — | O | CH₃ | (6-)C₂H₅ | O | CH₃ | N(CH₃)₂ | 199 |
| 1587 | — | O | CF₃ | (6-)C₂H₅ | O | CH₃ | CH=CH(CH₃) | 128 |
| 1588 | — | O | CF₃ | (6-)C₂H₅ | O | CH₃ | CH₂OCH₃ | 101 |
| 1589 | — | O | CF₃ | (6-)C₂H₅ | O | ▷ | N(CH₃)₂ | 154 |
| 1590 | — | O | CF₃ | (6-)C₂H₅ | O | ▷ | SC₂H₅ | 143 |
| 1591 | — | O | CF₃ | (6-)C₂H₅ | O | CH₃ | SC₂H₅ | 113 |
| 1592 | — | O | CF₃ | (6-)C₂H₅ | O | OC₂H₅ | C₂H₅ | 122 |
| 1593 | — | O | CF₃ | (6-)C₂H₅ | O | OC₂H₅ | SC₂H₅ | 133 |
| 1594 | — | O | CF₃ | (6-)C₂H₅ | O | CH₃ | OC₆H₅ | 193 |
| 1595 | — | O | CH₂CH₂F | (6-)CH₃ | O | CH₃ | C₂H₅ | 109 |
| 1596 | — | O | CH₂CH₂F | (6-)CH₃ | O | CH₃ | ▷ | 157 |
| 1597 | — | O | CH₂CH₂F | (6-)CH₃ | O | CH₃ | CH₂OCH₃ | 106 |
| 1598 | — | O | CH₂CH₂F | (6-)CH₃ | O | CH₃ | SCH₃ | 135 |
| 1599 | — | O | CH₂CH₂F | (6-)CH₃ | O | CH₃ | N(CH₃)₂ | 141 |
| 1600 | — | O | CH₂CH₂F | (6-)CH₃ | O | OC₂H₅ | C₂H₅ | 129 |
| 1601 | — | O | CH₂CH₂F | (6-)CH₃ | O | ▷ | CH₃ | 169 |
| 1602 | — | O | CH₂CH₂F | (6-)CH₃ | O | ▷ | OC₂H₅ | 125 |
| 1603 | — | O | CH₂CH₂F | (6-)CH₃ | O | ▷ | OC₃H₇ | 117 |

TABLE 1A-continued

Examples of the compounds of the formula (IA)

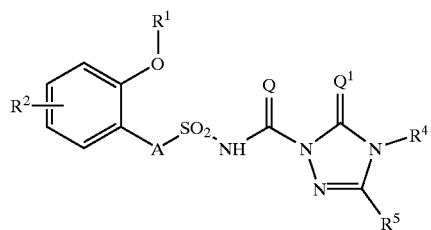

(IA)

| Ex. No. | A | Q | R¹ | (Position-) R² | Q¹ | R⁴ | R⁵ | Melting point ° C. |
|---|---|---|---|---|---|---|---|---|
| 1604 | — | O | CH₂CH₂F | (6-)CH₃ | O | CH₃ | O—CH₂—▷ | 145 |
| 1605 | — | O | CH₂CH₂F | (6-)CH₃ | O | ▷ | O—CH₂—▷ | 118 |
| 1606 | — | O | CH₂CH₂CH₂F | (6-)C₃H₇ | O | CH₃ | OCH₃ | 127 |
| 1607 | — | O | CH₂CH₂CH₂F | (6-)C₃H₇ | O | CH₃ | OCH(CH₃)₂ | 155 |
| 1608 | — | O | CH₂CH₂CH₂F | (6-)C₃H₇ | O | ▷ | OCH₃ | 106 |
| 1609 | — | O | CH₂CH₂CH₂F | (6-)C₃H₇ | O | ▷ | OCH(CH₃)₂ | 138 |
| 1610 | — | O | CH₂CH₂F | (6-)C₂H₅ | O | CH₃ | ▷ | 157 |
| 1611 | — | O | CH₂CH₂F | (6-)C₂H₅ | O | CH₃ | CH₂OCH₃ | 101 |
| 1612 | — | O | CH₂CH₂F | (6-)C₂H₅ | O | ▷ | CH₃ | 147 |
| 1613 | — | O | CH₂CH₂F | (6-)CH₃ | O | CH₃ | C₃H₇ | 280 |
| 1614 | — | O | CH₂CH₂CH₂F | (6-)C₃H₇ | O | CH₃ | CH₃ | 302 |
| 1615 | — | O | CH₂CH₂CH₂F | (6-)C₃H₇ | O | CH₃ | C₃H₇ | 261 |
| 1616 | — | O | CH₂CH₂F | (6-)C₃H₇ | O | CH₃ | C₃H₇ | 108 |
| 1617 | — | O | CH₂CH₂F | (6-)C₃H₇ | O | CH₃ | OCH₃ | 158 |
| 1618 | — | O | CH₂CH₂F | (6-)C₃H₇ | O | CH₃ | OC₂H₅ | 152 |
| 1619 | — | O | CH₂CH₂F | (6-)C₃H₇ | O | CH₃ | OCH(CH₃)₂ | 164 |
| 1620 | — | O | CH₂CH₂F | (6-)C₃H₇ | O | ▷ | OCH₃ | 137 |
| 1621 | — | O | CH₂CH₂F | (6-)C₃H₇ | O | ▷ | OC₂H₅ | 117 |
| 1622 | — | O | CH₂CH₂F | (6-)C₃H₇ | O | ▷ | OCH(CH₃)₂ | 158 |
| 1623 | — | O | CH₂CH₂F | (6-)C₃H₇ | O | CH₃ | N(CH₃)₂ | 147 |
| 1624 | — | O | CH₂CH₂F | (6-)C₃H₇ | O | OC₂H₅ | C₂H₅ | 237 |
| 1625 | — | O | CH₂CH₂F | (6-)C₃H₇ | O | CH₃ | SCH₃ | 130 |
| 1626 | — | O | CHF₂ | (6-)Br | O | CH₃ | OCH₃ | 160 |
| 1627 | — | O | CHF₂ | (6-)Br | O | CH₃ | CH₃ | 146 |
| 1628 | — | O | CHF₂ | (6-)Br | O | CH₃ | C₃H₇ | 127 |
| 1629 | — | O | CHF₂ | (6-)Br | O | CH₃ | OC₂H₅ | 168 |
| 1630 | — | O | CHF₂ | (6-)Br | O | CH₃ | OCH(CH₃)₂ | 126 |

TABLE 1A-continued

Examples of the compounds of the formula (IA)

(IA)

| Ex. No. | A | Q | R$^1$ | (Position-) R$^2$ | Q$^1$ | R$^4$ | R$^5$ | Melting point °C. |
|---|---|---|---|---|---|---|---|---|
| 1631 | — | O | CHF$_2$ | (6-)Br | O |  | OCH$_3$ | 145 |
| 1632 | — | O | CHF$_2$ | (6-)Br | O |  | OC$_2$H$_5$ | 125 |
| 1633 | — | O | CHF$_2$ | (6-)Br | O |  | OCH(CH$_3$)$_2$ | 148 |
| 1634 | — | O | CHF$_2$ | (6-)Br | O | CH$_3$ | N(CH$_3$)$_2$ | 173 |
| 1635 | — | O | CF$_3$ | (6-)F | O | CH$_3$ | SCH$_3$ | |
| 1636 | — | O | CF$_3$ | (6-)F | O | CH$_3$ | C$_2$H$_5$ | |
| 1637 | — | O | CF$_3$ | (6-)F | O | CH$_3$ | OC$_2$H$_5$ | |

The compound listed in Table 1 as Example 9 can be prepared, for example, as follows:

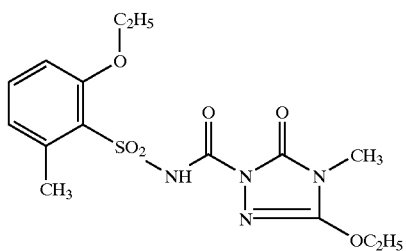

(9)

(Process (b))

1.4 g (0.01 mol) of 5-ethoxy-4-methyl-2,4-dihydro-3H-1,2,4-triazol-3-one and 2.4 g (0.01 mol) of 2-ethoxy-6-methyl-phenylsulphonyl isocyanate are stirred at 20° C. for 15 hours in 50 ml of acetonitrile. The solvent is distilled off, the residue is stirred with diethyl ether and the precipitate is filtered off with suction.

3.3 g (85% of theory) of 5-ethoxy-4-methyl-2-(2-ethoxy-6-methyl-phenylsulphonylaminocarbonyl)-2,4-dihydro-3H-1,2,4-triazol-3-one are obtained of melting point 160° C.

Starting Materials of the Formula (II) or (IIa):

Example (II-1)

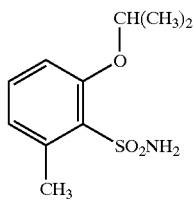

64.6 g (0.26 mol) of 2-isopropoxy-6-methyl-benzenesulphochloride are stirred at 20° C. for 12 hours in 350 ml of 25% strength aqueous ammonia solution. The crystalline product is subsequently isolated by filtration with suction.

54 g (90% of theory) of 2-isopropoxy-6-methyl-benzenesulphonamide are obtained of melting point 78° C.

Example (II-2)

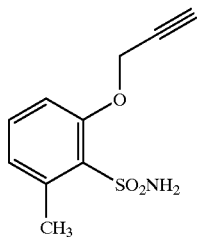

A mixture of 1.9 g (10 mmol) of 2-hydroxy-6-methyl-benzenesulphonamide, 1.2 g (10 mmol) of propargyl bromide (in the form of an 80% strength solution in toluene) and 1.4 g (10 mmol) of potassium carbonate is heated under reflux for 2 hours. The mixture is then filtered, the filtrate is concentrated under a water pump vacuum, the residue is digested with petroleum ether and the crystalline product obtained from this digestion is isolated by filtration with suction.

2.1 g (93% of theory) of 6-methyl-2-propargyloxy-benzenesulphonamide are obtained of melting point 129° C.

Example (II-3)

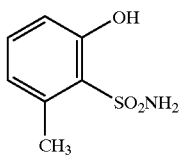

188 ml of a 1-molar solution of boron(III) bromide in methylene chloride are added dropwise at 20° C. with stirring to a solution of 32.3 g (0.15 mol) of 2-ethoxy-6-methylbenzenesulphonamide in 300 ml of methylene chloride, and the reaction mixture is stirred at 20° C. for 30 minutes. Then 300 ml of methanol are added dropwise at from 0° C. to 5° C. (ice cooling). After heating to 20° C., the reaction mixture is concentrated under a water pump vacuum and the residue is stirred with ethyl acetate. The solution obtained is washed with water, dried over sodium sulphate and filtered. The filtrate is concentrated under a water pump vacuum, the residue is crystallized by stirring with petroleum ether, and the crystalline product is isolated by filtration with suction.

20.3 g (72% of theory) of 2-hydroxy-6-methyl-benzenesulphonamide are obtained of melting point 126° C.

In analogy to Examples (II-1) to (II-3) and in accordance with the general description of the preparation process according to the invention, it is also possible, for example, to prepare the compounds of the formula (II) or (IIa) listed in Table 2 below.

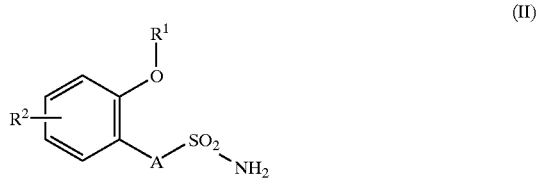

(II)

TABLE 2

Examples of the compounds of the formula (II)

| Ex. No. | A | $R^1$ | (position-) $R^2$ | Melting point (° C.) |
|---|---|---|---|---|
| II-4 | — | $C_2H_5$ | (6-)$CH_3$ | 104 |
| II-5 | — | $n$-$C_3H_7$ | (6-)$CH_3$ | 63 |
| II-6 | — | —$CH_2CH_2Cl$ | (6-)$CH_3$ | 102 |
| II-7 | — | $CH_3$ | (6-)$CH_3$ | 132 |
| II-8 | — | —$CH_2C_6H_5$ | (6-)$CH_3$ | 131 |
| II-9 | — | —$CH_2COOCH_3$ | (6-)$CH_3$ | 90 |
| II-10 | — | $CH_3$ | (6-)$C_3H_7$-n | 108 |
| II-11 | — | $C_2H_5$ | (6-)$C_3H_7$-n | 80 |
| II-12 | — | $C_2H_5$ | (5-)$CH_3$ | 131 |
| II-13 | — | $CH_3$ | (6-)Cl | 166 |
| II-14 | — | $C_2H_5$ | (6-)Cl | 121 |
| II-15 | — | H | (6-)Cl | 118 |
| II-16 | — | i-$C_3H_7$ | (6-)Cl | 85 |
| II-17 | — | —$CH_2CH$=$CH_2$ | (6-)Cl | 106 |
| II-18 | — | —$CH_2C$≡$CH$ | (6-)Cl | 181 |
| II-19 | — | $CF_3$ | (5-)Cl | |
| II-20 | — | $CHF_2$ | (5-)$CH_3$ | 127 |
| II-21 | — | $CHF_2$ | (6-)$CH_3$ | 89 |
| II-22 | — | $CH_3$ | (5-)$C(CH_3)_3$ | 160 |
| II-23 | — | $CH_3$ | (5-)Cl | |
| II-24 | — | $CHF_2$ | (4-)$CH_3$ | 153 |
| II-25 | — | —$CF_2CHFCl$ | (6-)$CH_3$ | 85 |
| II-26 | — | $C_2H_5$ | (6-)$CH_2Cl$ | |

Starting Materials of the Formula (IV):

Example (IV-1)

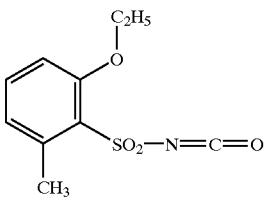

21.5 g (0.1 mol) of 2-ethoxy-6-methyl-benzenesulphonamide and 10 g (0.1 mol) of n-butyl isocyanate are heated to boiling in 100 ml of chlorobenzene. At reflux temperature, phosgene is passed in for 4 hours. The clear solution is concentrated under reduced pressure and the residue is subjected to precision distillation. At a pressure of 0.8 mbar and an overhead temperature of 135–140° C., 2-ethoxy-6-methyl-phenylsulphonyl isocyanate goes over and solidifies in the receiver.

7.9 g of 2-ethoxy-6-methyl-phenylsulphonyl isocyanate are obtained as a colourless product of melting point 40° C.

Starting Materials of the Formula (VI) or (VIa):

Example (VI-1)

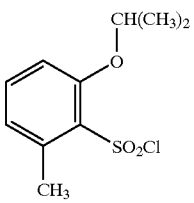

47.8 g (0.29 mol) of 2-isopropoxy-6-methyl-aniline are dissolved in a mixture of 87 ml of 1N hydrochloric acid and 145 ml of conc. hydrochloric acid, and the solution is cooled to −5° C. At −5° C. to 0° C., a solution of 22 g (0.32 mol). of sodium nitrite in 87 ml of water is then added dropwise with stirring and the mixture is stirred at about 0° C. for a further hour. After removal of the nitrite excess with amidosulphonic acid, the diazonium salt solution obtained is added dropwise at −5° C. to 0° C. to a saturated solution of sulphur dioxide in 175 ml of 1,2-dichloro-ethane. After about 30 minutes, 1.7 g of copper(I) chloride and 1.7 g of dodecyl-trimethylammonium bromide are added, and the reaction mixture is allowed to rise to room temperature over the course of about 60 minutes, heated to about 40° C. over a further hour, and stirred at this temperature for about 12 hours. At about 20° C., 14.2 g of a 35% strength hydrogen peroxide solution are then added and the mixture is stirred for about 30 minutes. It is subsequently stirred with 300 ml of methylene chloride, and the organic phase is separated off, washed with water, dried over sodium sulphate and filtered. The solvent is carefully removed from the filtrate by distillation under a water pump vacuum.

65.9 g (90% of theory) of 2-isopropoxy-6-methyl-benzenesulphochloride are obtained as a brownish oily residue.

$^1$H-NMR (CDCl$_3$, TMS, δ ppm): 1.47 (d, J=6.1 Hz, 2x$CH_3$); 2.68 (s, $CH_3$); 4.79 (sept., J=6.1 Hz, 1H); 6.83 (d, J=7.5 Hz, 1H); 6.95 (d, J=8.4 Hz, 1H); 7.45 (pseudo t, J=8.3 Hz, 1H).

In analogy to Example (VI-I) it is also possible, for example, to prepare the compounds of the formula (VI) or (VIa) listed in Table 3 below.

TABLE 3

(VI)

Examples of the compounds of the formula (VI)

| Ex. No. | A | R$^1$ | (position-) R$^2$ | Physical data |
|---|---|---|---|---|
| VI-2 | — | CH$_3$ | (6-)CH$_3$ | Fp.: 52° C. |
| VI-3 | — | C$_2$H$_5$ | (6-)CH$_3$ | $^1$H-NMR(CDCl$_3$, TMS, δ, ppm): 1,55 (t, J=6,97 Hz, CH$_3$), 2,69(s, CH$_3$), 4,24(q, J=6,97 Hz, CH$_2$), 6,87(d, J=7,68 Hz, 1H), 6,95(d, J=8,34 Hz, 1H), 7,46(pseudo t, J=8,1 Hz, 1H) |
| VI-4 | — | n-C$_3$H$_7$ | (6-)CH$_3$ | $^1$H-NMR(CDCl$_3$, TMS, δ, ppm): 1,33 (t, J=7,38 Hz, CH$_3$), 1,95(m, CH$_2$), 2,69(s, CH$_3$), 4,12(t, J=6,3 Hz, CH$_2$), 6,86(d, J=7,69 Hz, 1H), 6,94 (d, J=8,37 Hz, 1H), 7,46(pseudo t, J=7,8 Hz, 1H) |
| VI-5 | — | —CH$_2$CH$_2$Cl | (6-)CH$_3$ | $^1$H-NMR(CDCl$_3$, TMS, δ, ppm): 2,71 (s, CH$_3$), 3,94(t, J=6,1 Hz, CH$_2$), 4,41(t, J=6, 1 Hz, CH$_2$), 6,96(t, J=7, 1 Hz, 2H), 7,5(t, J=7,8 Hz, 1H) |
| VI-6 | — | —CH$_2$CH$_2$OC$_2$H$_5$ | (6-)CH$_3$ | $^1$H-NMR(CDCl$_3$, TMS, δ, ppm): 1,23 (t, J=7 Hz, CH$_3$), 2,69(s, CH$_3$), 3,65 (q, J=7 Hz, CH$_2$), 3,91(t, J=5,16 Hz CH$_2$), 4,30(t, J=5,16 Hz, CH$_2$), 6,89 (d, J=7,7 Hz, 1H), 7,0(d, J=8,3 Hz 1H), 7,47(pseudo t, J=8,1 Hz, 1H) |
| VI-7 | — | C$_2$H$_5$ | (5-)CH$_3$ | $^1$H-NMR(CDCl$_3$, TMS, δ, ppm): 1,53 (t, J=7 Hz, CH$_3$), 2,36(s, CH$_3$), 4,25 (q, J=7 Hz, CH$_2$), 7,0(d, J=8,53 Hz, 1H), 7,45(d, J1=8,53 Hz, J2=2,15 Hz, 1H), 7,75(d, J=2,15 Hz, 1H) |
| VI-8 | — | n-C$_3$H$_7$ | (5-)CH$_3$ | $^1$H-NMR(CDCl$_3$, TMS, δ, ppm): 1,08 (t, J=7,38 Hz, CH$_3$), 1,85(m, CH$_2$), 2,23(s, CH$_3$), 3,99(t, J=6,5 Hz), 6,74 (d, J=8,2 Hz, 1H), 6,92(m, 1H), 7,34 (d, J=1,65 Hz, 1H) |
| VI-9 | — | i-C$_3$H$_7$ | (5-)CH$_3$ | $^1$H-NMR(CDCl$_3$, TMS, δ, ppm): 1,45 (d, J=6,06, 2xCH$_3$), 2,35(s,CH$_3$), 4,77(sept., J=6,06 Hz, 1H), 6,99(d, J=8,57 Hz, 1H), 7,43(dd, J1=8,56 Hz, 1H, J2=2,1 Hz, 1H), 7,74(d, J=2,1 Hz, 1H) |
| VI-10 | — | C$_2$H$_5$ | (6-)CH$_2$Cl | (Oil) |
| VI-11 | — | —CF$_2$CHFCl | (6-)CH$_3$ | $^1$H-NMR(CDCl$_3$, TMS, δ, ppm): 2,78 (s, CH$_3$), 6,46(td, CHFCl), 7,2–7,6 (Ar—H) |
| VI-12 | — | CHF$_2$ | (6-)CH$_3$ | $^1$H-NMR(CDCl$_3$, TMS, δ, ppm): 2,76 (s, CH$_3$), 6,61(t, CHF$_2$), 7,27–7,59 (Ar—H) |
| VI-13 | — | CH$_3$ | (5-)C(CH$_3$)$_3$ | Fp.: 62° C. |
| VI-14 | — | CHF$_2$ | (4-)CH$_3$ | $^1$H-NMR(CDCl$_3$, TMS, δ, ppm): 2,50 (s, CH$_3$), 6,68(t, CHF$_2$), 7,05–7,92 (Ar—H) |
| VI-15 | — | CHF$_2$ | (5-)CH$_3$ | $^1$H-NMR(CDCl$_3$, TMS, δ, ppm): 2,45 (s, CH$_3$), 6,64(t, CHF$_2$), 7,35–7,86 (AR—H) |
| VI-16 | — | —CH$_2$CH$_2$Cl | (6-)CH$_3$ | |
| VI-17 | — | —CH$_2$CH=CH$_2$ | (6-)CH$_3$ | |
| VI-18 | — | —CH$_2$C≡CH | (6-)CH$_3$ | |
| VI-19 | — | —CH$_2$C$_6$H$_5$ | (6-)CH$_3$ | |

Starting Materials of the Formula (X)

Example (X-1)

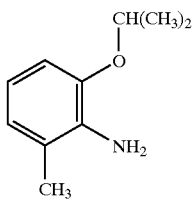

Step 1: Preparation of 2-Isopropoxy-6-methyl-nitrobenzene

A mixture of 153 g (1.0 mol) of 3-methyl-2-nitro-phenol, 172.5 g (1.25 mol) of potassium carbonate, 170 g (1.0 mol) of 2-iodo-propane and 400 ml of acetone is heated under reflux for 12 hours. It is subsequently concentrated under a water pump vacuum, the residue is stirred with 400 ml of methylene chloride, the mixture is filtered and the filter product is washed with methylene chloride. The solvent is removed carefully from the filtrate by distillation under a water pump vacuum.

183.4 g of 2-isopropoxy-6-methyl-nitrobenzene are obtained as a yellow oily residue.

$^1$H-NMR (CDCl$_3$, TMS, δ, ppm): 1.33 (d, J=6.1 Hz, 2xCH$_3$), 2.28 (s, CH$_3$), 4.6 (sept., J=6.1 Hz, 1H), 6.8 (d, J=7.7 Hz, 1H), 6.87 (d, J=8.4 Hz, 1H), 7.26 (pseudo t, J=8.1 Hz, 1H).

Step 2: Preparation of 2-Isopropoxy-6-methyl-aniline 183.3 g (0.94 mol) of 2-isopropoxy-6-methyl-nitrobenzene are hydrogenated in 1 litre of ethyl acetate in the presence of 9.5 g of Raney nickel under a hydrogen pressure of from 40 to 60 bar for 5 hours. The mixture is then filtered and the solvent is carefully removed from the filtrate by distillation under a water pump vacuum.

139.4 g (90% of theory) of 2-isopropoxy-6-methyl-aniline are obtained as an orange-coloured oily residue.

$^1$H-NMR (CDCl$_3$, TMS, δ, ppm): 1.36 (d, J=6.1 Hz, 2xCH$_3$), 2.16 (s, CH$_3$), 3.72 (s, NH$_2$), 4.51 (sept., J=6.1 Hz, 1H), 6.65–6.70 (m, 3H).

Use Examples

In the Use Examples, the compounds specified below are used as comparison substances:

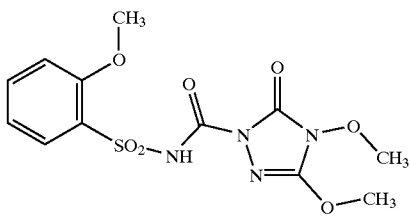

(A)

4,5-Dimethoxy-2-(2-methoxy-phenylsulphonylamino-carbonyl)-2,4-dihydro-3H-1,2,4-triazol-3-one (known from EP 534266);

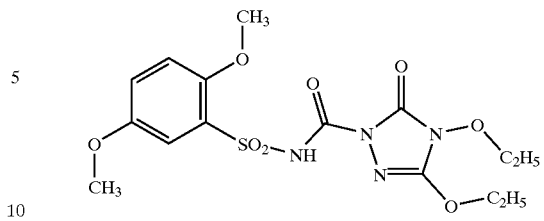

(B)

4,5-Diethoxy-2-(2,5-dimethoxy-phenylsulphonylamino-carbonyl)-2,4dihydro-3H-1,2,4-triazol-3-one (known from EP 534266).

Example A

Pre-emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil, and, after 24 hours, the soil is watered with the preparation of the active compound. It is expedient to keep constant the amount of water per unit area. The concentration of the active compound in the preparation is of no importance, only the amount of active compound applied per unit area being decisive.

After three weeks, the degree of damage to the plants is rated in % damage in comparison to the development of the untreated control. The figures denote:

0%=no action (like untreated control) 100%=total destruction

In this test, the compounds according to Preparation Examples 1, 7–21, 23–41, 46–49, 51, 54, 55, 57, 60, 62, 65, 68, 72–74, 76, 78, 79, 88, 89, 199, 207, 209, 222 and 901 for example, exhibit a very strong action against broad-leaved weeds.

Example B

Post-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control. The figures denote:

0%=no action (like untreated control) 100%=total destruction

In this test, the compounds according to Preparation Examples 1, 7–10, 12, 13, 15, 16, 17, 25, 30, 31, 38, 40, 41, 46 and 47, for example, exhibit a very strong action against broad-leaved weeds.

What is claimed is:

1. A compound of the formula (II), (IV) or (VI):

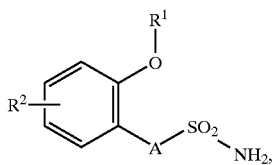
(II)

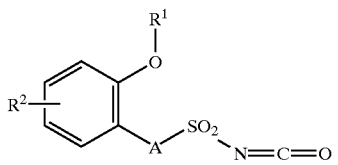
(IV)

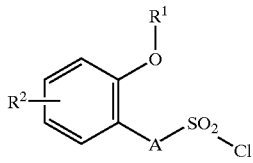
(VI)

wherein

A represents a single bond;

$R^1$ represents ethyl substituted by fluoro, chloro, bromo, methoxy or ethoxy, or represents n- or i-propyl, n-, s- or i-butyl, propenyl, butenyl, propinyl or butinyl, each of which is optionally substituted by fluoro, chloro, bromo, methoxy or ethoxy;

$R^2$ represents cyano, fluoro, chloro or bromo, or represents methyl substituted by fluoro, or represents ethyl, n- or i-propyl, n- or i-propoxy, n- or s-butoxy, each of which is optionally substituted by fluoro, chloro, bromo, methoxy or ethoxy;

and $R^2$ is in position 6.

2. A compound of the formula (II), (IV) or (VI):

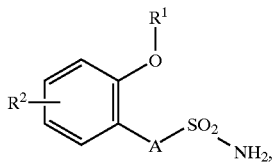
(II)

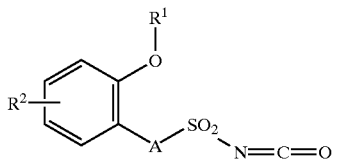
(IV)

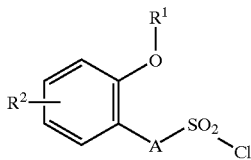
(VI)

wherein

A represents a single bond;

$R^2$ is in position 6;

and the substituents $R^1$ and $R^2$ are selected according to the following combinations:

| Combination No. | $R^1$ | $R^2$ |
|---|---|---|
| 1 | Allyl | O—C$_2$H5 |
| 2 | CHF$_2$ | Br |
| 3 | CHF$_2$ | O—C$_3$H$_7$-n |
| 4 | CHF$_2$ | CHF$_2$ |
| 5 | CF$_3$ | Br |
| 6 | CH$_2$CH$_2$—O—C$_2$H$_5$ | CH$_3$ |
| 7 | CH$_3$ | C$_3$H$_7$-i |
| 8 | CH$_3$ | C$_3$H$_7$-n |
| 9 | CH$_3$ | O—C$_3$H$_7$-n |
| 10 | CH$_3$ | O—C$_4$H$_9$-n |
| 11 | CH$_3$ | O—C$_4$H$_9$-s |
| 12 | CH$_3$ | CN |
| 13 | C$_2$H$_5$ | Cl |
| 14 | C$_2$H$_5$ | F |
| 15 | C$_2$H$_5$ | C$_2$H$_5$ |
| 16 | C$_2$H$_5$ | O—C$_2$H$_5$ |
| 17 | C$_2$H$_5$ | C$_3$H$_7$-n |
| 18 | C$_2$H$_5$ | O—C$_3$H$_7$-i |
| 19 | C$_2$H$_5$ | O—C$_3$H$_7$-n |
| 20 | C$_2$H$_5$ | O-C$_4$H$_9$-n |
| 21 | H | CF$_3$ |
| 22 | C$_3$H$_7$-n | Cl |
| 23 | C$_3$H$_7$-n | F |
| 24 | C$_3$H$_7$-n | CF$_3$ |
| 25 | C$_3$H$_7$-n | Br |
| 26 | C$_3$H$_7$-n | C$_3$H$_7$-n |
| 27 | C$_3$H$_7$-n | O—CH$_2$F$_2$ |
| 28 | C$_3$H$_7$-i | Cl |
| 29 | C$_3$H$_7$-i | CH$_3$ |
| 30 | C$_3$H$_7$-i | F |
| 31 | C$_3$H$_7$-i | CF$_3$ |
| 32 | C$_3$H$_7$-i | C$_2$H$_5$ |
| 33 | C$_3$H$_7$-i | C$_3$H$_7$-i |
| 34 | C$_3$H$_7$-i | O—C$_3$H$_7$-i |
| 35 | cyclopentyl | O—CH$_3$ |
| 36 | CH$_2$CH$_2$—Cl | CH$_3$ |
| 37 | CH$_2$CHFCl | CH$_3$ |
| 38 | C$_4$H$_9$-n | CH$_3$ |
| 39 | C$_4$H$_9$-i | O—CH$_3$ |
| 40 | C$_4$H$_9$-i | O—C$_2$H$_5$ |
| 41 | CF$_2$Cl | CH$_3$ |
| 42 | CH$_2$CH$_2$F | CH$_3$ |
| 43 | CH$_2$CH$_2$F | CF$_3$ |
| 44 | CH$_2$CH$_2$F | C$_2$H$_5$ |
| 45 | C$_4$H$_9$-s | C$_4$H$_9$-s |
| 46 | CH$_2$CHF$_2$ | CH$_3$ |
| 47 | CH$_2$CHF$_2$ | C$_2$H$_5$ |
| 48 | CH$_2$CHF$_2$ | C$_3$H$_7$-n |
| 49 | CH$_2$CH$_2$O—C$_3$H$_7$-n | O—CH$_3$ |
| 50 | CH$_2$CH$_2$CH$_2$F | C$_3$H$_7$-n |
| 51 | C$_4$H$_9$-i | CH$_3$ |

* * * * *